(12) United States Patent
Zdzalik et al.

(10) Patent No.: US 9,776,988 B2
(45) Date of Patent: Oct. 3, 2017

(54) PYRAZOLYLBENZO[D]IMIDAZOLE DERIVATIVES

(71) Applicant: CELON PHARMA S.A., Kielpin/Lomianki (PL)

(72) Inventors: Daria Zdzalik, Zwolen (PL); Joanna Lipner, Rzeszow (PL); Maciej Wieczorek, Kielpin/Lomianki (PL); Karolina Dzwonek, Warsaw (PL); Abdellah Yamani, Stare Grochale (PL); Krzysztof Dubiel, Warsaw (PL); Monika Lamparska-Przybysz, Warsaw (PL); Paulina Grygielewicz, Minsk Mazowiecki (PL); Aleksandra Stanczak, Warsaw (PL)

(73) Assignee: Celon Pharma S.A., Kielpin/Lomianki (PL)

( * ) Notice: Subject to any disclaimer, the term of this patent is extended or adjusted under 35 U.S.C. 154(b) by 0 days.

(21) Appl. No.: 14/775,240

(22) PCT Filed: Mar. 7, 2014

(86) PCT No.: PCT/IB2014/059515
§ 371 (c)(1),
(2) Date: Sep. 11, 2015

(87) PCT Pub. No.: WO2014/141015
PCT Pub. Date: Sep. 18, 2014

(65) Prior Publication Data
US 2016/0039794 A1    Feb. 11, 2016

(30) Foreign Application Priority Data
Mar. 14, 2013   (PL) .......................... 403149

(51) Int. Cl.
*C07D 403/04*  (2006.01)
*C07D 401/14*  (2006.01)
(Continued)

(52) U.S. Cl.
CPC ......... *C07D 403/04* (2013.01); *C07D 401/14* (2013.01); *C07D 403/14* (2013.01); *C07D 409/14* (2013.01)

(58) Field of Classification Search
CPC .. C07D 403/04; C07D 403/14; C07D 401/14; C07D 409/14
See application file for complete search history.

(56) References Cited

U.S. PATENT DOCUMENTS

2008/0125418 A1* 5/2008 Babin .................. C07D 231/12
                                                                514/227.8

OTHER PUBLICATIONS

Voskoglou-Nomikos et al., Clinical Cancer Research, vol. 9, 4227-4239.*
(Continued)

*Primary Examiner* — Rebecca Anderson
(74) *Attorney, Agent, or Firm* — Gary J. Gershik; Cooper & Dunham LLP

(57) ABSTRACT

A compound represented by the general Formula (I), wherein hydrogen atoms shown as attached to pyrazole and benzimidazole rings are attached to one of nitrogen atoms of the pyrazole or benzimidazole ring, respectively; $R^1$ represents —X-Q-P, wherein X is absent or represents —$CH_2$—, —C(O)—, or —C(O)NH—$(CH_2)_k$—, wherein k is 0, 1 or 2; Q is selected from the group consisting of Q1, Q2, Q3, Q4 and Q5; P is absent or represents straight- or branched-chain C1-C3 alkyl, —$(CH_2)_l$—$NR^2R^3$, or —$(CH_2)_m$—C(O)—$NR^2R^3$, wherein l and m independently of each other represent 0, 1 or 2, with the proviso that when B in Q1 represents oxygen atom, then P is absent; and $R^2$ and $R^3$ independently represent C1 or C2 alkyl, or $R^2$ and $R^3$ (Continued)

together with nitrogen atom to which they are both attached form a 6-membered saturated heterocyclic ring, wherein one of carbon atoms can be replaced with oxygen, —NH— or —N(C1-C2)alkyl-; and acid addition salts thereof. The compound can be useful in the treatment of cancer diseases.

(I)

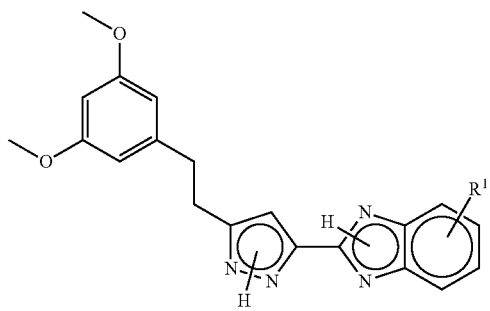

32 Claims, 1 Drawing Sheet

(51) Int. Cl.
C07D 409/14 (2006.01)
C07D 403/14 (2006.01)

(56) References Cited

OTHER PUBLICATIONS ptcl.chem.ox.ac.uk/MSDS structure activity relationship; Jaworska, 1-8, 2004.*

Cancer and Metastasis Reviews (1998), 17(1), 91-106.*

Science (1999), vol. 286, 531-537.*

International Search Report issued by the International Searching Authority (ISA/O.E.P.M.) on May 21, 2014 in connection with International Application No. PCT/IB2014/059515.

* cited by examiner

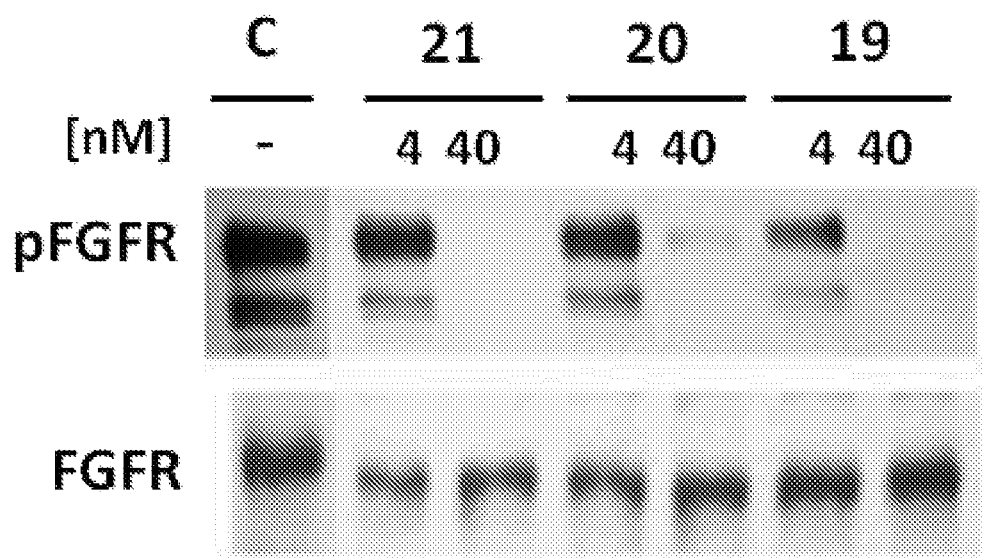

PYRAZOLYLBENZO[D]IMIDAZOLE DERIVATIVES

This application is a §371 national stage of PCT International Application No. PCT International Application No. PCT/IB2014/059515, filed Mar. 7, 2014, designating the United States, and claiming priority of Polish Patent Application No. P.403149, filed Mar. 14, 2013.

The invention relates to pyrazolylbenzo[d]imidazole derivatives, pharmaceutical compositions containing them, and their use as medicaments, in particular for treating cancer diseases.

One of potential target in the treatment of cancer diseases is blockade of the signalization pathway of the Fibroblast Growth Factor (FGF) by inhibition of FGF receptor (FGFR) with small-molecule tyrosine kinase FGFR inhibitors.

FGF receptor family consists of five members, four of which (FGF(1-4)) are tyrosine kinase receptors. Fibroblast Growth Factor and its receptors play a key role in cell development and human physiology. Besides their normal physiological roles, and as a result of dysregulation of FGFR signalization pathway, FGF and FGFR can act as oncogenes that drive proliferation of many human cancers and can also mediate resistance to cytotoxic agents and targeted therapies. Dysregulation of FGF/FGFR signalization pathway and overexpression of FGFR was found in many types of cancers.

There are known non-selective FGFR kinase inhibitors of mixed-type (multi-target) that besides FGFR kinases act on many other tyrosine kinases, as well as inhibitors that act selectively on FGFR kinases. Inhibition of many tyrosine kinases may contribute to the enhanced spectrum of side effects of a medicament. This in turn limits possibilities of administration of a dose effective for target indication and is not always balanced by its efficacy that can be potentially enhanced by broader spectrum of activity. The activity of mixed inhibitors with respect to FGFR kinase is usually low. Recently, second generation compounds which are potent FGFR inhibitors with a greater selectivity margin towards FGFR kinase comparing to other tyrosine kinases are also reported.

WO2006/070195 discloses pyrazolylbenzo[d]imidazole compounds substituted at the position 4 of the pyrazole ring with urea or amide moiety. The compounds are described as having anti-cancer activity via interaction on multitarget-type kinases.

U.S. Pat. No. 8,288,425 discloses kinase inhibitors of the mixed-type of the following formula

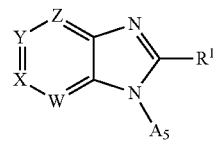

that encompasses amongst others benzimidazole derivatives wherein $R^1$ can be substituted with pyrazole. There is no disclosure of any specific group of compounds wherein pyrazolyl is substituted at the position 5 with 3,5-dimethoxyphenethyl. The compounds are described as inhibitors of many kinases (multi-target), including protein kinase SYK (Spleen Tyrosine Kinase), VEGFR2 (also known as KDR or FLK-1) (Vascular Endothelial Growth Factor), ITK (IL2-inducible T-cells kinase), of the potential activity as angiogenesis inhibiting agents and thus applicable in the treatment of solid cancers. Although FGFR kinase is mentioned, no compounds are identified that would have the activity of modulation of FGFR kinases, especially selective inhibition of FGFR kinases.

A need still exists of novel small-molecule compounds which are FGFR kinase inhibitors selective over other kinases, especially over VEGFR2 kinase (KDR).

A need still exists of novel small-molecule compounds that are selective FGFR kinase inhibitors with high potency and that can find use in the treatment of cancer diseases.

BRIEF DESCRIPTION OF THE FIGURES

FIG. 1. Results of the test of FGFR2 phosphorylation in SNU-16 cells treated with selected compounds of invention at 4 and 40 nM for 1 hour.

Present invention relates to novel compounds of the general Formula (I)

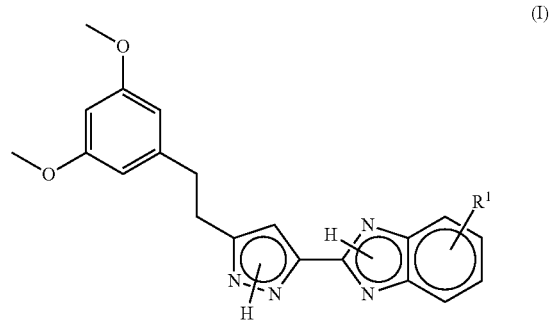

wherein
hydrogen atoms shown as attached to pyrazole and benzimidazole rings are attached to one of nitrogen atoms of the pyrazole or benzimidazole ring, respectively;
$R^1$ represents —X-Q-P, wherein
X is absent or represents —CH$_2$—, —C(O)—, or —C(O)NH—(CH$_2$)$_k$—, wherein k is 0, 1 or 2;
Q is selected from the group consisting of Q1, Q2, Q3, Q4 and Q5, wherein
Q1 is

wherein A represents —CH— or nitrogen atom, and B represents —CH—, oxygen atom O or nitrogen atom, and when Q1 represents piperazinylene, it can be optionally additionally substituted with two methyl groups at the positions 3,5;
Q2 is

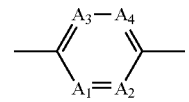

wherein one of A1, A2, A3, A4, and A5 represents nitrogen atom, and the others represent C;

Q3 is

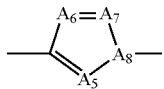

wherein one of A5, A6, A7 and A8 represents nitrogen atom, and the others represent C, especially Q3 is presented by Q31, Q31 is

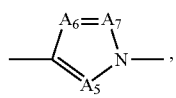

wherein one of A5, A6 and A7 represents nitrogen atom, and the others represent C;

Q4 is

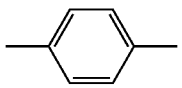

and Q5 is

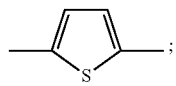

P is absent or represents straight- or branched-chain C1-C3 alkyl, —(CH$_2$)$_l$—NR$^2$R$^3$, or —(CH$_2$)$_m$—C(O)—NR$^2$R$^3$, wherein l and m independently of each other represent 0, 1 or 2, with the proviso that when B in Q1 represents oxygen atom, then P is absent; and R$^2$ and R$^3$ independently represent C1 or C2 alkyl, or R$^2$ and R$^3$ together with nitrogen atom to which they are both attached form a 6-membered saturated heterocyclic ring wherein one of carbon atoms of said heterocyclic ring can be optionally replaced with —O—, —NH— or —N(C1-C2) alkyl;

and acid addition salts thereof.

The compounds of Formula (I) exhibit tautomerism phenomen which involves migration of hydrogen between nitrogen atoms in the pyrazole and benzimidazole rings. Two tautomeric forms, wherein hydrogen atom is attached to one of the two nitrogen atoms, are possible for both pyrazole ring and benzimidazole rings. Tautomeric forms are in equilibrium with each other.

Therefore, in the compounds of the invention 4 tautomeric forms are possible in total, represented by the following equivalent formulas (IA), (IB), (IC), and (ID).

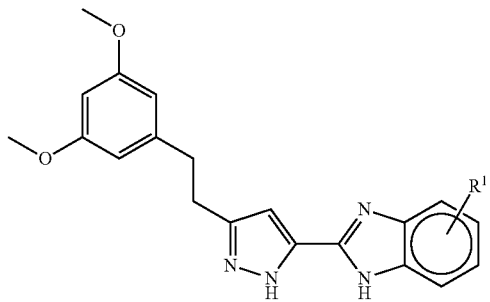

(IA)

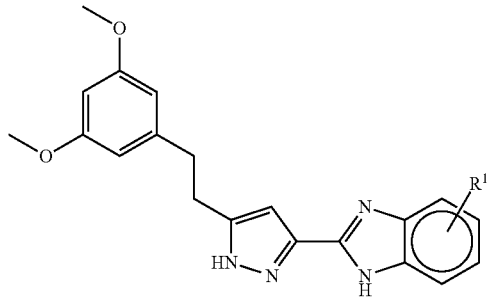

(IB)

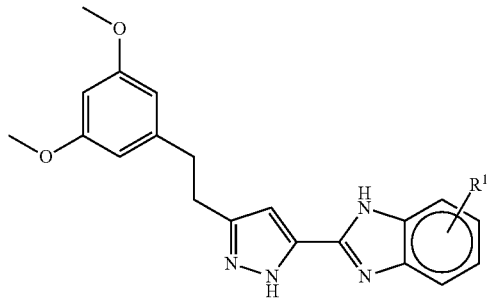

(IC)

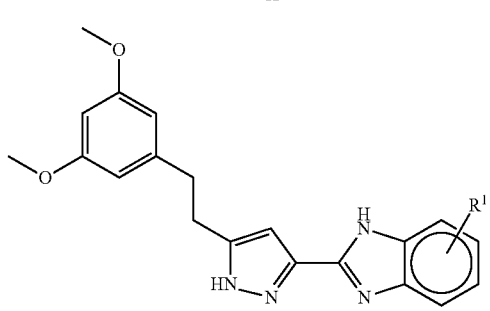

(ID)

All above structures (IA), (IB), (IC) and (ID) are equivalent and represent the same chemical compound.

The compounds of the invention exhibit the activity of inhibition of tyrosine kinase of the Fibroblast Growth Factor Receptor and therefore can be useful in the treatment of cancer diseases.

Therefore, the object of the invention are the compounds of Formula (I) as defined above for use as a medicament.

The object of the invention are also the compounds of Formula (I) as defined above for use in a method of treating cancer diseases.

The object of the invention is also a pharmaceutical composition which comprises the compound of Formula (I) as defined above and pharmaceutically acceptable excipients.

The object of the invention is also the use of the compound of Formula (I) as defined above for the preparation of a medicament for the treatment of cancer diseases.

The object of the invention is also a method of treating cancer diseases, which comprises administration to a patient in need thereof of a therapeutically effective amount of the compound of Formula (I) as defined above.

As it is shown in Formula (I), $R^1$ is attached at the benzene ring of the benzimidazole moiety.

Preferably, $R^1$ is attached at the position 4(7) or 5(6) of the benzimidazole moiety.

One embodiment of the invention is the compound of Formula (I) wherein $R^1$ is attached at the position 4(7) of benzimidazole moiety.

Another embodiment of the invention is the compound of Formula (I) wherein $R^1$ is attached at the position 5(6) of benzimidazole moiety.

In one group of the compounds of the invention of Formula (I) X is absent.

In a second group of the compounds of the invention of Formula (I) X represents —C(O)—.

In another group of the compounds of the invention of Formula (I) X represents —CH$_2$—.

In yet another group of the compounds of the invention of Formula (I) X represents —C(O)NH—(CH$_2$)$_k$—, wherein k is 0, 1 or 2. In a particular case k is 0. In another particular case k is 0 or 1, 0 or 2, or 1 or 2.

Another group of the compounds of the invention are the compounds of Formula (I), wherein P represents straight or branched chain C1-C3 alkyl.

Yet another group of the compounds of the invention are the compounds of Formula (I), wherein P is absent.

Yet another group of the compounds of the invention are the compounds of Formula (I), wherein P represents —(CH$_2$)$_l$—NR$^2$R$^3$, or —(CH$_2$)$_m$—C(O)—NR$^2$R$^3$, wherein l and m independently are 0, 1 or 2, and $R^2$ and $R^3$ represent alkyl C1 or C2, or $R^2$ and $R^3$ together with nitrogen atom to which they are both attached form a 6-membered saturated heterocyclic ring wherein one of carbon atoms of said heterocyclic ring can be optionally replaced with —O—, —NH— or —N(C1-C2)alkyl.

One subgroup of this group are the compounds of Formula (I), wherein P represents —(CH$_2$)$_l$—NR$^2$R$^3$.

Another subgroup of this group are the compounds of Formula (I), wherein P represents —(CH$_2$)$_m$—C(O)—NR$^2$R$^3$.

A subgroup of this group are the compounds wherein $R^2$ and $R^3$ together with nitrogen atom to which they are both attached form a 6-membered saturated heterocyclic ring wherein one of carbon atoms of said heterocyclic ring can be optionally replaced with —O—, —NH— or —N(C1-C2)alkyl.

Another sub-group of this group are the compounds wherein $R^2$ and $R^3$ represent C1 or C2 alkyl.

Another group are the compounds wherein Q is selected from the group consisting of Q1, Q2, Q3, especially Q31, and Q5.

Another group are the compounds wherein Q is selected from the group consisting of Q1, Q2, and Q3, especially Q31.

Another group are the compounds wherein Q is Q1.

Another group are the compounds wherein $R^1$ is attached at the position 4(7), X is absent, and Q is selected from the group consisting of Q1, Q2, Q3, especially Q31.

A subgroup of this group are the compounds wherein P is absent.

Another subgroup of this group are the compounds wherein P is selected from the group consisting of straight or branched chain alkyl C1-C3, —(CH$_2$)$_l$—NR$^2$R$^3$ and —(CH$_2$)$_m$—C(O)—NR$^2$R$^3$, wherein l and m independently of each other represent 0, 1 or 2, and $R^2$ and $R^3$ represent alkyl C1 or C2, or $R^2$ and $R^3$ together with nitrogen atom to which they are both attached form a 6-membered saturated heterocyclic ring wherein one of carbon atoms of said heterocyclic ring can be optionally replaced with —O—, —NH— or —N(C1-C2)alkyl.

Further group are the compounds wherein $R^1$ is attached at the position 5(6), X is absent and Q is Q1. Preferred in this group are the compounds wherein P is absent.

Another subgroup of this group are the compounds wherein P is selected from the group consisting of straight or branched chain alkyl C1-C3, —(CH$_2$)—NR$^2$R$^3$ and —(CH$_2$)$_m$—C(O)—NR$^2$R$^3$, wherein l and m independently of each other represent 0, 1 or 2, and $R^2$ and $R^3$ represent alkyl C1 or C2, or $R^2$ and $R^3$ together with nitrogen atom to which they are both attached form a 6-membered saturated heterocyclic ring wherein one of carbon atoms of said heterocyclic ring can be optionally replaced with —O—, —NH— or —N(C1-C2)alkyl-.

Further group are the compounds wherein $R^1$ is substituted at the position 5(6), X is selected from the group consisting of —CH$_2$—, —C(O)— and —C(O)NH—(CH$_2$)$_k$—, wherein k is 0, 1 or 2, and Q is Q1.

A subgroup of this group are the compounds wherein P is absent.

Another subgroup of this are the compounds wherein P is selected from the group consisting of straight or branched chain alkyl C1-C3, —(CH$_2$)$_l$—NR$^2$R$^3$ and —(CH$_2$)$_m$—C(O)—NR$^2$R$^3$, wherein l and m independently of each other represent 0, 1 or 2, and $R^2$ and $R^3$ represent alkyl C1 or C2, or $R^2$ and $R^3$ together with nitrogen atom to which they are both attached form a 6-membered saturated heterocyclic ring wherein one of carbon atoms of said heterocyclic ring can be optionally replaced with —O—, —NH— or —N(C1-C2)alkyl.

When in any one of the above groups, subgroups or embodiments said 6-membered saturated heterocyclic ring formed by $R^2$ and $R^3$ together with nitrogen atom to which they are both attached wherein one of carbon atoms of said heterocyclic ring can be optionally replaced with —O—, —NH— or —N(C1-C2)alkyl form can be in particular piperidine, piperazine, 4-methyl or 4-methyl piperazine, or morpholine.

As discussed above, due to tautomerism in pyrazole and benzimidazole rings of the compounds of Formula (I) of the invention there is migration of hydrogen atoms between nitrogen atoms of the rings and compounds of Formula (I) are equilibrium mixtures of 4 tautomeric forms. Depending on the nitrogen atom of the ring at which hydrogen atom is attached, numbering of the positions according to the IUPAC rules will differ. Therefore, in the present specification names of the compounds next to the numbers indicating the positions of pyrazole and benzimidazole rings include the position corresponding to the form wherein hydrogen atom is at another nitrogen atom. That is, pyrazolyl as a substituent of benzimidazole in Formula (I) can be designated as pyrazol-3(5)-yl, the position in pyrazole substituted with 3,5-dimethoxyphenethyl can be designated as 5(3), and substituted positions of benzimidazole moiety can be designated as 5(6) and 4(7). However, for the sake of simplicity, structural formulae of the compounds of the invention are presented as a single tautomeric form, which corresponds to 5-(3,5-dimethoxyphenethyl)pyrazol-3(5)-yl-substituted benzimidazole moiety substituted with R¹ at the position 4 or 5.

Specific compounds of Formula (I) of the invention are selected from the following group:
1. 4-((2-(5(3)-(3,5-dimethoxyphenethyl)-1H-pyrazol-3(5)-yl)-1H-benzo[d]-imidazol-5(6)-yl)methyl)morpholine;
2. (2-(5(3)-(3,5-Dimethoxyphenethyl)-1H-pyrazol-3(5)-yl)-1H-benzo[d]imidazol-5(6)-yl)(morpholino)methanone;
3. 2-(5(3)-(3,5-Dimethoxyphenethyl)-1H-pyrazol-3(5)-yl)-N-(tetrahydro-2H-pyran-4-yl)-1H-benzo[d]imidazole-5(6)-carboxyamide;
4. 2-(5(3)-(3,5-Dimethoxyphenethyl)-1H-pyrazol-3(5)-yl)-N-(3-morpholinopropyl)-1H-benzo[d]imidazole-5(6)-carboxyamide;
5. 2-(5(3)-(3,5-Dimethoxyphenethyl)-1H-pyrazol-3(5)-yl)-5(6)-((4-ethylpiperazin-1-yl)methyl)-1H-benzo[d]imidazole;
6. (2. (5(3)-(3,5-Dimethoxyphenethyl)-1H-pyrazol-3(5)-yl)-1H-benzo[d]imidazol-5(6)-yl)(4-ethylpiperazin-1-yl)methanone;
7. 2-(5(3)-(3,5-Dimethoxyphenethyl)-1H-pyrazol-3(5)-yl)-5(6)-((4-methyl-piperazin-1-yl)methyl)-1H-benzo[d]imidazole;
8. (2-(5(3)-(3,5-Dimethoxyphenethyl)-1H-pyrazol-3(5)-yl)-1H-benzo[d]imidazo-5(6)-yl)(4-methylpiperazin-1-yl)methanone;
9. 2-(5(3)-(3,5-Dimethoxyphenethyl)-1H-pyrazol-3(5)-yl)-5(6)-(((3R,5S)-3,5-dimethylpiperazin-1-yl)methyl)-1H-benzo[d]imidazole;
10. (2-(5(3)-(3,5-Dimethoxyphenethyl)-1H-pyrazol-3(5)-yl)-1H-benzo[d]imidazol-5-yl)((3R,5S)-3,5-dimethylpiperazin-1-yl)methanone;
11. 2-(5(3)-(3,5-Dimethoxyphenethyl)-1H-pyrazol-3(5)-yl)-5(6)-(piperidin-1-ylmethyl)-1H-benzo[d]imidazole;
12. 2-(5(3)-(3,5-Dimethoxyphenethyl)-1H-pyrazol-3(5)-yl)-5(6)-((4-(4-methyl-piperazin-1-yl)piperidin-1-yl)methyl)-1H-benzo[d]imidazole;
13. 5(6)-([1,4'-Bipiperidin]-1'-ylmethyl)-2-(5(3)-(3,5-dimethoxyphenethyl)-1H-pyrazol-3(5)-yl)-1H-benzo[d]imidazole;
14. 4-(2-(4-((2-(5(3)-(3,5-Dimethoxyphenethyl)-1H-pyrazol-3(5)-yl)-1H-benzo[d]-imidazol-5(6)-yl)methyl)piperazin-1-yl)ethyl)morpholine;
15. 2-(4-((2-(5(3)-(3,5-Dimethoxyphenethyl)-1H-pyrazol-3(5)-yl)-1H-benzo[d]-imidazol-5(6)-yl)methyl)piperazin-1-yl)-N,N-dimethylacetamide;
16. 4-(2-(5(3)-(3,5-Dimethoxyphenethyl)-1H-pyrazol-3(5)-yl)-1H-benzo[d]imidazol-5(6)-yl)morpholine;
17. 2-(5(3)-(3,5-Dimethoxyphenethyl)-1H-pyrazol-3(5)-yl)-5(6)-(4-methyl-piperazin-1-yl)-1H-benzo[d]imidazole;
18. 2-(5(3)-(3,5-Dimethoxyphenethyl)-1H-pyrazol-3(5)-yl)-5(6)-(4-ethylpiperazin-1-yl)-1H-benzo[d]imidazole;
19. 2-(5(3)-(3,5-Dimethoxyphenethyl)-1H-pyrazol-3(5)-yl)-5(6)-((3R,5S)-3,5-dimethylpiperazin-1-yl)-1H-benzo[d]imidazole
20. 2-(4-(2-(5(3)-(3,5-Dimethoxyphenethyl)-1H-pyrazol-3(5)-yl)-1H-benzo[d]-imidazol-5(6)-yl)piperazin-1-yl)-N,N-diethylethanamine;
21. 2-(4-(2-(5(3)-(3,5-Dimethoxyphenethyl)-1H-pyrazol-3(5)-yl)-1H-benzo[d]-imidazol-5(6)-yl)piperazin-1-yl)-1-morpholinoethanone;
22. 4-(2-(5(3)-(3,5-Dimethoxyphenethyl)-1H-pyrazol-3(5)-yl)-1H-benzo[d]-imidazol-4(7)-yl)morpholine;
23. 2-(5(3)-(3,5-Dimethoxyphenethyl)-1H-pyrazol-3(5)-yl)-4(7)-((3R,5S)-3,5-dimethylpiperazin-1-yl)-1H-benz[d]imidazole;
24. 2-(5(3)-(3,5-Dimethoxyphenethyl)-1H-pyrazol-3(5)-yl)-4(7)-(4-isopropylpiperazin-1-yl)-1H-benzo[d]imidazole;
25. 4(7)-([1,4'-bipiperidin]-1'-yl)-2-(5(3)-(3,5-dimethoxyphenethyl)-1H-pyrazol-3(5)-yl)-1H-benzo[d]imidazole;
26. 4-(2-(4-(2-(5(3)-(3,5-Dimethoxyphenethyl)-1H-pyrazol-3(5)-yl)-1H-benzo[d]-imidazol-4(7)-yl)piperazin-1-yl)ethyl)morpholine;
27. 4-(2-(3-(2-(5(3)-(3,5-Dimethoxyphenethyl)-1H-pyrazol-3(5)-yl)-1H-benzo[d]-imidazol-5(6)-yl)-1H-pyrazol-1-yl)ethyl)morpholine;
28. 4-((5(3)-(2-(5(3)-(3,5-Dimethoxyphenethyl)-1H-pyrazol-3(5)-yl)-1H-benzo[d]-imidazol-5(6)-yl)thiophen-2-yl)methyl)morpholine;
29. 4-(3-(2-(5(3)-(3,5-Dimethoxyphenethyl)-1H-pyrazol-3(5)-yl)-1H-benzo[d]-imidazol-5(6)-yl)benzyl)morpholine
30. (4-(2-(5(3)3-(3,5-Dimethoxyphenethyl)-1H-pyrazol-3(5)-yl)-1H-benzo[d]-imidazol-5(6)-yl)phenyl)(morpholino)methanone;
31. (4-(2-(5(3)-(3,5-Dimethoxyphenethyl)-1H-pyrazol-3(5)-yl)-1H-benzo[d]-imidazol-5(6)-yl)phenyl)(morpholino)methanone;
32. 4-(4-(2-(3-(3,5-Dimethoxyphenethyl)-1H-pyrazol-3(5)-yl)-1H-benzo[d]-imidazol-5(6)-yl)phenyl)morpholine; and
33. 4-(5(3)-(2-(3-(3,5-Dimethoxyphenethyl)-1H-pyrazol-3(5)-yl)-1H-benzo[d]-imidazol-5(6)-yl)pyridin-2-yl)morpholine;

and acid addition salts thereof.

The compounds of the invention represented by the general formula (I) can be obtained by reacting corresponding 1H-pyrazolecarbonyl compound of the general formula (II)

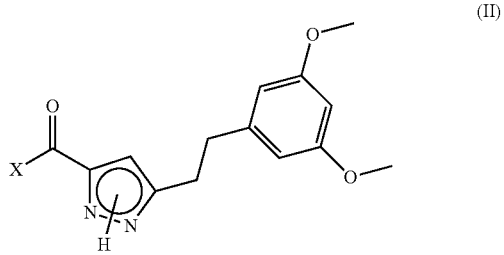

(II)

wherein X represents OR, wherein R is hydrogen atom, methyl or ethyl, with corresponding benzeneamine derivative of the general formula (III)

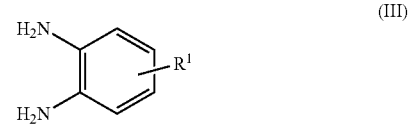

(III)

wherein R¹ has the same meaning as defined above for Formula (I).

This reaction is shown on the scheme 1 below.

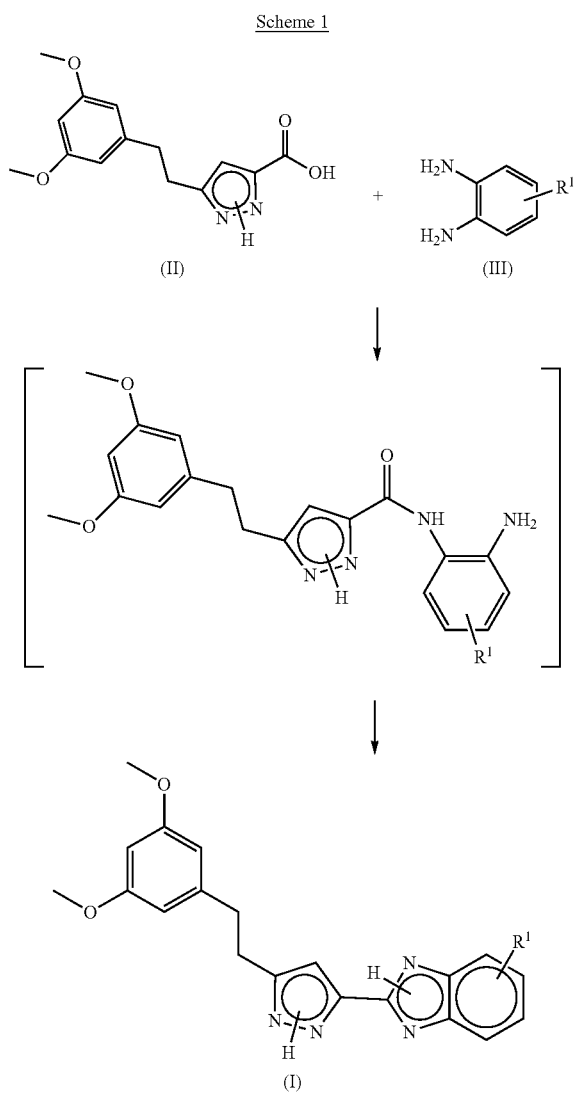

The reaction of the compound of Formula (I) with the compound of Formula (II) can be carried out in accordance with known techniques of carrying such reactions as described in the literature, adapting those techniques appropriately to given starting compounds.

The reaction of preparation of the compound of the general Formula (I) can be carried out in an inert solvent or mixture of solvents, in the presence of a base, at ambient temperature or under reflux, with the addition of a catalyst or oxidant, for example oxygen (J. J. V. Eynde et al., *Bulletin des Societes Chimiques Belges*, 102, No. 5, 1993, 357-364), or iodine (K. Osowska et. al., *Journal of the American Chemical Society*, 133, 4, 2011, 724-727). Suitable solvents are DMSO, DMF, N,N-dimethylacetamide, acetonitrile, tetrahydrofurane, 1,4-dioxan, toluene, methanol, ethanol, n-butanol, chloroform, dichloromethane, 1,2-dichloroethane, ethylene glycol, and water. Sodium hydride, sodium ethanolate or potassium tert-butanolate, DBU, pyridine, piperidine, or triethylamine can be used as bases. As a catalyst [bis(acethoxy)iodo]benzene ((Du Li-Hua, *Synthesis*, No. 5, 2007, 675-678), yterbium(III) triflate (S. Ming-Gui, *Journal of Fluorine Chemistry*, 128, 3, 2007, 232-235), or cerium amonium(IV) nitrate (M. Kidwai et al., Journal of Chemical Sciences, 122, 4, 2010, 607-612) can be used.

The reaction of the compound of the Formula (II) wherein R is hydrogen atom with the compound of the Formula (III) can be carried out in an inert solvent or mixture of solvents, in the presence of an acid, at ambient temperature or under reflux, with the addition of a catalyst, using microwaves. Suitable solvents are dichloromethane, 1,2-dichloroethane, toluene, xylene, DMF, and pyridine. Sulphuric, polyphosphoric, or acetic acid can be used as the acid. Preferred are acetic or polyphosphoric acid (R. Dubey, S. H. Narayana, Chemical and Pharmaceutical Bulletin, 55, 1, 2007, 115-117). As a catalyst for the reaction vanadium(IV) oxide acethylacetate can be used (Ch. K. Lee, et al., *Heterocycles*, 78, 2, 2009, 425-433; M. Dey, et al., *Chinese Chemical Letters*, 22, 3, 2011, 296-299) lub silphox ($POCl_3$-n($SiO_2$)n) (A. Hasaninejad, et al., *Phosphorus, Sulfur and Silicon and the Related Elements;* 184, 1, 2009, 147-155).

The reaction of the compound of the Formula (II) wherein R is methyl or ethyl with the compound of the Formula (III) can be carried out in an inert solvent or mixture of solvents, in the presence of an acid or base, at ambient temperature or under reflux, with the addition of a catalyst. Suitable solvents are DMSO, acetonitrile, toluene, xylene or DMF. Preferably, toluene or acetonitrile is used. Sulphuric acid, polyphosphoric acid, acetic acid, and Lewis acids and their ether complexes can be used as the acid. Preferred is the use of acetic and polyphosphoric acids (Hein et al., *Journal of the American Chemical Society*, 1957, 79, 427) or diethylaluminium chloride. As the base, sodium or potassium hydroxide can be used. As the catalyst of the reaction potassium fluoride of copper(I) chloride can be used.

Formation of the compounds of the general formula (I) is an equilibrium process, therefore it is advantageous to remove water or alcohol formed in the reaction as side products. For removal of side products absorbing agents/adsorbents can be used, such as for example molecular sieves 3 Å or 4 Å, anhydrous salts or oxides, for example anhydrous magnesium sulphate, phosphorus pentoxide, or physical processes involving formation of azeotropic mixtures.

Advantageously, the reaction of the compound of the Formula (II) wherein R is hydrogen atom, with the compound of the Formula (III) is carried out in a solvent that forms azeotropic mixture with water, and water formed in the reaction is removed under reflux as an azeotropic mixture using suitable devices, such as for example Dean-Stark apparatus.

Starting compound of the Formula (II), wherein X is OR, can be obtained from 3,5-dimethoxybenzaldehyde of the Formula (IV)

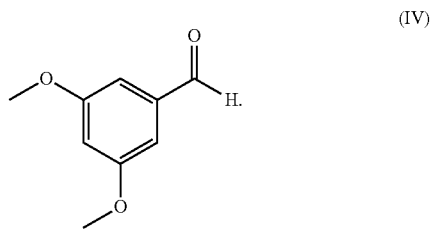

(IV)

The compound of the above Formula (IV) is reacted in the condensation reaction with acetone to obtain intermediate compound ((3E)-4-(3,5-dimethoxyphenyl)but-3-en-2-one) of the Formula (V)

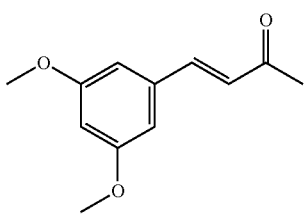

(V)

Condensation is carried out in an inert solvent, such as acetone, at the temperature in the range 0 to 60° C., preferably 0° C. to ambient temperature.

Alternative way of the preparation of the compound of the Formula (V) is the reaction of the compound of the Formula (IV) with α-trimethylsilylacetate in the presence of a catalyst carried out in an inert solvent, i.e. for example in tetrahydrofuran at ambient temperature (K. Wadhawa, J. G. Verkade, *J. Org. Chem.*, 2009, 76, 4697-4702), or known reaction of the preparation of cinnamic acid derivatives from arylaldehydes and monoethylmalonate in the Doebner-Knoevenagel condensation (J. Lu, P. H. Toy, *Synlett,* 2011, 1723-1726), or known Wittig and Wadsworth-Emmons reactions of the preparation of α,β-unsaturated carbonyl compounds using corresponding phosphorous derivatives (T. D. W. Claridge et al., *Org. Lett.,* 2008, 10, 5437-5440; A. El-Batta et al., *J. Org. Chem.,* 2007, 72, 5244-5259; F. Orsini et al., *Synlett.,* 2006, 1717-1718).

Subsequently, the compound of the above Formula (V) is reduced with hydrogen in the presence of a catalyst to obtain intermediate compound (4-(3,5-dimethoxy-phenyl)butan-2-one) of the Formula (VI)

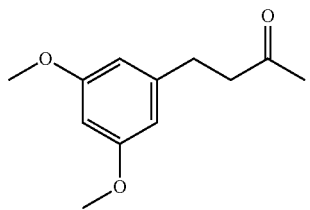

(VI)

Reduction can be carried out in an inert solvent, such as ethanol, ethyl acetate or toluene, at the temperature in the range 0 to 80° C., preferably 20° C. to 60° C. Noble metals can be used as a catalyst, i.e. palladium, platinum, their oxides or salts deposited on a support such as active carbon, silica or polystyrene, or nickel and its salts, for example nickel(II) chloride (F. Alonso et. al., *Synlett,* 2006, 3017-3020), or a mixture of catalysts from the group of organic tin hydrides, for example tributyttin (IV) hydride, with silicon hydrides, for example phenylsilicon (IV) hydride (D. S. Hays et al., *J. Org. Chem.,* 1996, 61, 6751-6752)

An alternative way of preparation of the compound of the Formula (VI) can be substitution of ethyl acethylacetate or its derivatives with appropriate halide, well described in the literature (W. A. Benjamin: *House Modern Synthetic Reactions,* 2nd ed., New York, 1972, 492-570, 586-595; X. W. Fenget et al., *Green Chemistry,* 2009 11, 12, 1933-1936), wherein desired 4-aryl-3-buten-2-one derivatives are obtained as a result of simultaneous hydrolysis of ester group under acidic or basic conditions and subsequent decarboxylation (Meier et al., *Tetrahedron Lett.,* 1989, 30, 5253).

Subsequently, the compound of the Formula (VI) is reacted in the condensation reaction with diethyl or dimethyl oxalate to obtain intermediate ethyl or methyl ester of 6-(3,5-dimethoxyphenyl)-2,4-dioxohexanoic) acid of the Formula (VII), wherein R is methyl or ethyl.

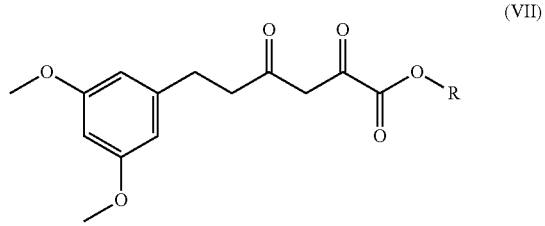

(VII)

Sodium ethanolate, tert-butanolate, hydride or amide can be used as a base. Preferably, the base is sodium ethanolate and the solvent is ethanol. Condensation reaction is accelerated and its yield significantly improved in the presence of crown ethers.

The compound of the above Formula (VII) is then reacted in the condensation reaction with hydrazine $NH_2$—$NH_2$, to form an ester of the Formula (VIII), wherein R is ethyl or methyl.

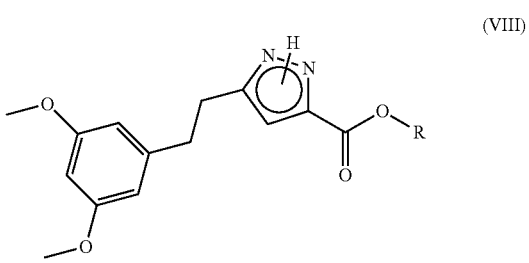

(VIII)

The reaction of the compound of the Formula (VII) with hydrazine is carried out in a solvent, at a temperature in the range 20° C. to reflux temperature, preferably at ambient temperature. Hydrazine can be used in the cyclisation reaction as an aqueous hydrazine solution 20 to 65%, hydrate or inorganic salt, for example hydrochloride. The solvent can be an alcohol (methanol, ethanol), ether (tetrahydrofuran, dioxan) or solvent mixtures ethanol and acetic acid, or ethanol and THF and water; acetic acid alone can be used as well (S. T. Heller et al., *Org. Lett.,* 2006, 8, 2675-2678).

In the reaction with hydrazine there is obtained a mixture of tautomers of the compound of the Formula (VIII), differing with the place of attachment of hydrogen atom at one of the two nitrogen atoms in the ring and the arrangement of unsaturated bonds in the pyrazole ring, i.e. VIIA and VIIB. The mixture can be separated into isomers by column chromatography, for example on silica gel.

The ester of the above Formula (VIII) is then hydrolysed to the carboxylic acid of the Formula (IX)

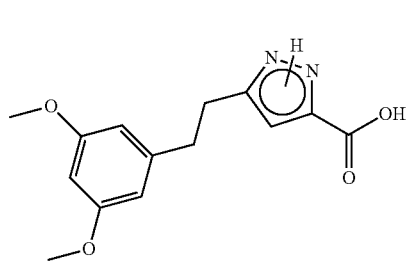

Hydrolysis to the carboxylic acid of the Formula (IX) is carried out using a base (sodium, potassium or lithium hydroxide). As a solvent dioxan, methanol, ethanol, tetrahydrofuran or N,N-dimethylformamide can be used. Temperature of the reaction is in the range from ambient temperature (preferred) to reflux temperature.

The preparation of the compound of the Formula (II), wherein R is H or ethyl is illustrated in the Scheme 2 below.

Starting compounds of the Formula (III)

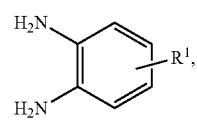

depending on the place of attachment of substituent $R^1$, and in consequence reagents used for their preparation, can be divided into two groups represented y below general Formulas (IIIA) and (IIIB).

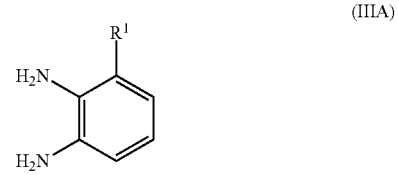

Scheme 2

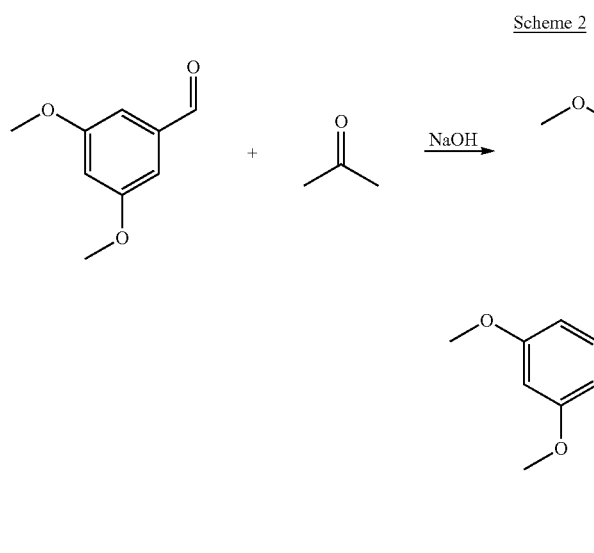

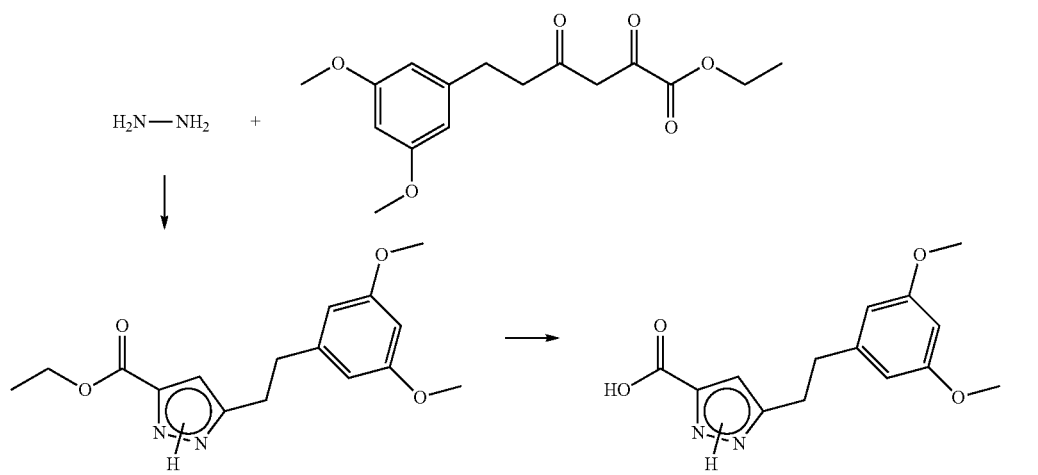

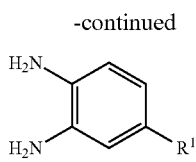
(IIIB)

In the case when X is absent, and Q in R1 represents Q1, wherein A is nitrogen atom, i.e. cyclic amine, for example morpholine, piperazine, substituted piperazine or piperidine, the compound of the Formula (IIIA) is obtained from 3-chloro-2-nitroaniline, and the compound of the Formula (IIIB) from 5-chloro-2-nitroaniline by reaction with appropriate alkylamine HR$^1$ in the reaction of aromatic nucleophilic substitution (D. P. Self, *Journal of the Chemical Society, Chemical Communications*, 1980, 281-282; V. A. Kuznetsov et al., *Journal of Organic Chemistry USSR (English Translation)*, 1986, 22, 403-404; B. Sreedhar, *Synthesis*, 2009, 15, 2517-2522; Ortho-McNeil Pharmaceutical, Inc. U.S. Pat. No. 6,358,946 B1, 2002), and then reduction of nitro groups to amino groups, for example using hydrogen in the presence of palladium on active carbon.

In the case when X is absent, and Q in R1 represents Q2, Q3, Q4 or Q5, the compound of the Formula (IIIA) is obtained from 3-chloro-2-nitroaniline and the compound of the Formula (IIIB) from 5-chloro-2-nitroaniline by the reaction with corresponding boronic acids R$^1$—B(OH)$_2$ or its pinacol esters in the known Suzuki reaction, and then reduction of nitro groups to amino groups, for example using hydrogen in the presence of palladium on active carbon In the case when X represents —C(O)—, the compound of the Formula (IIIB) is obtained from 3,4-dinitrobenzoic acid, which is converted to acid chloride, subsequently acid chloride is substituted with appropriate amine HR$^1$, and then reduction of nitro groups to amino groups is carried out, for example using hydrogen in the presence of palladium on active carbon.

In the case when X represents —CH$_2$—, the compound of the Formula (IIIB) is obtained from 3,4-dinitrobenzoic acid, which is converted to acid chloride, subsequently acid chloride is substituted with appropriate amine H-Q-P, —C(O)— group is reduced to —CH$_2$— group, and then nitro groups are reduced to amino groups, for example using hydrogen in the presence of palladium on active carbon.

When X in R$^1$ represents —CH$_2$—, the compound of the Formula (IIIB) is obtained from 3,4-dinitrobenzoic acid, which is converted to (3,4-dinitrophenyl)methanol with borate-THF complex, which is treated with methanosulphonic acid chloride to obtain 3,4-dinitrobenzylmethyl methanesulphonate, and then methanesulphonate is substituted with appropriate amine of the Formula H-Q-P, and nitro groups are reduced to amino groups, for example using hydrogen in the presence of palladium on active carbon.

When X in R$^1$ represents —C(O)NH—(CH$_2$)$_k$—, wherein k is 0, 1 or 2, the compound of the Formula (IIIB) is obtained from 3,4-dinitrobenzoic acid, which is converted to acid chloride, acid chloride is subjected to the reaction of substitution with appropriate amine of the Formula H—R$^1$, and then nitro groups are reduced to amino groups, for example using hydrogen in the presence of palladium on active carbon.

In the treatment of diseases mentioned above the compounds of the Formula (I) of the invention can be administered as a chemical compound, however typically will be used in the form of pharmaceutical compositions comprising the compound of the invention or its pharmaceutically acceptable salt as defined above as an active substance, and pharmaceutically acceptable carriers and auxiliary substances.

In the treatment of diseases mentioned above, the compositions of the invention will be administered by any route, preferably by oral or parenteral route and will have the form of a preparation destined for use in medicine, depending on the intended route of administration.

Compositions for oral administration can have the form of solid or liquid preparations. Solid preparations can have, for example, the form of a tablet or capsule produced in a conventional manner from pharmaceutically acceptable inactive excipients such as binders (for example, pregelatinised corn starch, polyvinylpyrrolidone or hydroxypropylmethylcellulose); fillers (for example lactose, saccharose or calcium hydrogenphosphate), lubricants (for example magnesium stearate, talc or silica), wetting agents (for example sodium laurylsulphate). Tablets can be coated with coatings well known in the art, such as simple coatings, delayed/controlled-release coatings or enteric coatings. Liquid preparations for oral administration can be in a form of, for example, solutions, syrups or suspensions, or can have the form of dry solid product for reconstitution in water or other suitable vehiculum before use. Such liquid preparations can be prepared using conventional means from pharmaceutically acceptable excipients, such as suspending agents (for example sorbitol syrup, cellulose derivatives or hydrogenated edible oils), emulsifiers (for example lecithine or acacia gum), nonaqueous vehicles (for example mandelic oil, oil esters, ethyl alcohol or fractionated vegetable oils), and preservatives (for example methyl or propyl p-hydroxybenzoate or sorbic acid). Preparations can also include suitable buffering agents, flavoring agents and sweeteners.

Preparations for oral administration can be formulated so as to obtain controlled release of the active compound using methods known for a person skilled in the art.

Parenteral route of administration includes administration by intramuscular and intravenous injections, as well as intravenous infusions. Compositions for parenteral administration can, for example, have the form of a unit dosage form, such as ampoules, or multidosage containers, with the addition of a preservative. Compositions can have the form such as suspension, solution or emulsion in an oily or aqueous vehiculum, and can include excipients such as suspending agents, stabilizers, and/or dispersing agents. Alternatively, the active ingredient can be formulated as a powder for reconstitution before use in a suitable carrier, for example sterile, pyrogen-free water.

The method of treatment with the use of the compounds of the present invention will comprise administration of a therapeutically effective amount of the compound of the invention, preferably in the form of a pharmaceutical composition, to the subject in need of such treatment.

Proposed dosage of the compounds of the invention is from 0.1 to about 1000 mg per day, in a single dose or in divided doses. It will be apparent for a person skilled in the art that selection of a dosage required for obtaining desirable biological effect will depend on many factors, for example specific compound, the indication, the manner of administration, the age and condition of a patient and that exact dosage will be ultimately determined by a responsible physician.

Preparation of the compounds of the invention is illustrated in the Examples enclosed below. Syntheses described in the Examples were not optimized with respect to the yield, the amounts of reagents and final form of obtained compounds. All organic solutions were dried over anhydrous sodium sulphate.

The following analytical procedures were used for obtained compounds.

$^1$H and $^{13}$C NMR spectra were measured on Varian Mercury 500 or Varian Unity Inova 300 spectrometer against tetramethylsilane as an internal standard. The values of chemical shifts δ are given in [ppm]. Coupling constants J are given in [Hz].

Determinations of the mass (m/z) of the compounds were made using Quadrupole LC/MS 6130 from Agilent Technologies mass spectrometer in the ESI technique.

TLC analyses were performed on commercial silicagel plates MERCK 60 F254.

Chromatographic purifications were performed on silicagel 60 MERCK, size 40-63 μm (230-400 mesh ASTM) using chromatograph FP-971 Flash Purification System from Agilent Technologies.

Starting compounds for the syntheses described in the following Examples were obtained in accordance with routine or described in the literature procedures known for skilled persons.

PREPARATION OF STARTING AND INTERMEDIATE COMPOUNDS

Compound P1.
4-(3,5-Dimethoxyphenyl)but-3-en-2-one (method 1)

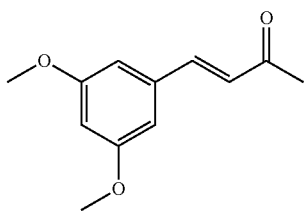

To the solution of 3,5-dimethoxybenzaldehyde (2.0 g, 12.04 mmol) in acetone (25 ml) 24 ml of 1M sodium hydroxide solution were added dropwise during 30 minutes. The reaction was carried out at ambient temperature for three hours. The progress of the reaction was monitored by TLC chromatography (system: heptane/ethyl acetate, 3/1). The product was extracted from the reaction mixture with chloroform (1×100 ml, 2×50 ml). Combined organic layers were dried over anhydrous sodium sulphate. After removal of the solvent a crude product was purified by column chromatography (system: heptane/ethyl acetate, 90/10). 1.39 g of the title product in the form of a yellow solid were obtained (yield 56%).

MS-ESI: (m/z) calculated for $C_{12}H_{14}O_3Na$ [M+Na]$^+$: 229.09, found 229.

$^1$H NMR (300 MHz, CDCl$_3$): δ 7.42 (d, J=16.2 Hz, 1H,) 6.66-6.69 (m, 3H), 6.51 (s, 1H), 3.82 (s, 6H), 2.38 (s, 3H) ppm.

Compound P1.
4-(3,5-Dimethoxyphenyl)but-3-en-2-one (method 2)

To the 2 l flask 3,5-dimethoxybenzaldehyde (16 g, 96 mmol), triphenylphosphine (33.3 g, 105 mmol) and 500 ml of toluene were added. The reaction was carried out for 48 hours at 75° C. and monitored by TLC analysis (system: heptane/ethyl acetate 3/1). The solvent was evaporated, and obtained solid dissolved in ethyl acetate. The majority of triphenylphosphine oxide was crystallized by the addition of heptane. The filtrate was concentrated and purified by chromatography on silicagel (system: heptane/ethyl acetate, 3/1). 18.5 g of the product in the form of a yellow solid were obtained (yield 93%).

Compound P2.
4-(3,5-Dimethoxyphenyl)butan-2-one

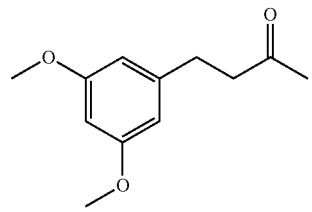

4-(3,5-Dimethoxyphenyl)but-3-en-2-one (Compound P1, 1.39 g, 6.74 mmol) was dissolved in 20 ml of ethanol. To the reaction 0.27 g of the 10% suspension of palladium on active carbon in ethanol were added. The reaction was carried out under hydrogen atmosphere at ambient temperature overnight. The progress of the reaction was monitored by TLC analysis (system: heptane/toluene: 6/4). The reaction mixture was filtered through celite bed and after evaporation of solvents purified by chromatography on silicagel (system: heptane/ethyl acetate: 8/1→5/1). 1.167 g of the product in the form of a colorless oil were obtained (yield 83%).

MS-ESI: (m/z) calculated for $C_{12}H_{17}O_3$ [M+H]$^+$: 209.11, found 209.1.

$^1$H NMR (300 Hz CDCl$_3$): δ 6.34 (d, J=2.1 Hz, 2H), 6.30 (t, J=2.1 Hz, 1H), 3.77 (s, 6H), 2.86-2.81 (m, 2H), 2.77-2.73 (m, 2H), 2.15 (s, 3H) ppm.

Compound P3:
6-(3,5-dimethoxyphenyl)-2,4-dioxohexanoic acid ethyl ester

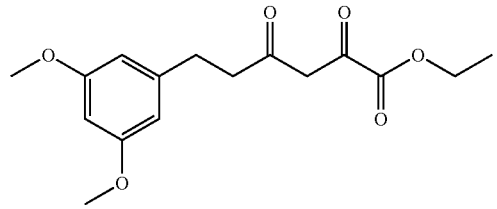 [SMILES: CCOC(=O)C(=O)CC(=O)CCc1cc(OC)cc(OC)c1]

To the flask containing 20 ml of dry ethanol metallic sodium (0.166 g) was added portionwise. The whole system was maintained under argon atmosphere. After dissolution of sodium the flask was cooled in water/ice bath, diethyl oxalate (0.53 g, 7.20 mmol) and then the solution of 4-(3,5-dimethoxyphenyl)butan-2-one (Compound P2, 0.75 g, 3.60 mmol) in ethanol were added. The reaction was carried out at 0-5° C. for two hours, then at ambient temperature for 20 hours. The progress of the reaction was monitored by TLC analysis (system: heptane/ethyl acetate, 4/1). The reaction mixture was diluted with ethyl acetate and neutralized with 1M HCl solution. Organic phase was washed with brine and dried over anhydrous sodium sulphate. The compound was isolated by column chromatography (system: heptane/ethyl acetate, 8/1). 0.665 g of the product in the form of a colorless oil were obtained (yield 60%).

MS-ESI: (m/z) calculated for $C_{16}H_{19}O_6$ [M−H]⁻: 307.11, found 307.1.

¹H NMR (300 MHz, CDCl₃): δ 6.37-6.32 (m, 3H), 4.44-4.32 (m, 3H), 3.78 (s, 6H), 2.95-2.89 (m, 2H), 2.85-2.79 (m, 2H), 1.43-1.37 (m, 3H) ppm.

Compound P4: 5(3)-[2-(3,5-dimethoxyphenyl)ethyl]-1H-pyrazole-3(5)-carboxylic acid ethyl ester

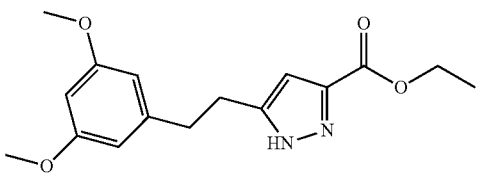 [SMILES: CCOC(=O)c1cc(CCc2cc(OC)cc(OC)c2)[nH]n1]

To the solution of 6-(3,5-dimethoxyphenyl)-2,4-dioxohexanoic acid ethyl ester (Compound P3, 3.6 g, 11.68 mmol) in 70 ml of ethanol hydrazine hydrate (1.9 ml, 23.4 mmol) and acetic acid (1 ml, 17.5 mmol) were added. The reaction was carried out for 5 hours at 80° C. The reaction was monitored by TLC analysis (system: heptane/ethyl acetate, 1/1). Water was added with and the mixture neutralized with 1M NaHCO₃. Aqueous phase was extracted with chloroform (3×50 ml). Combined organic fractions were washed with water and brine and dried over anhydrous magnesium sulphate. After concentration, the reaction mixture was purified by chromatography on silicagel (system: heptane/ethyl acetate, 9/1→1/1). 3.4 g of the title product in the form of a yellow solid were obtained (yield 95.7%).

MS-ESI: (m/z) calculated for $C_{16}H_{20}N_2O_4Na$ [M+Na]⁺: 327.14, found 327.1, for $C_{16}H_{19}N_2O_4$ [M−H]⁻: 303.13, found 303.1.

¹H NMR (300 MHz, CDCl₃) δ 6.63 (s, 1H), 6.32-6.50 (m, 3H), 4.37 (q, J=7.2 Hz, 2H), 3.77 (s, 6H), 3.0-2.88 (m, 4H), 1.38 (t, J=7.2 Hz, 3H) ppm.

Compound P5: 5(3)-[2-(3,5-dimethoxyphenyl)ethyl]-1H-pyrazole-3(5)-carboxylic acid

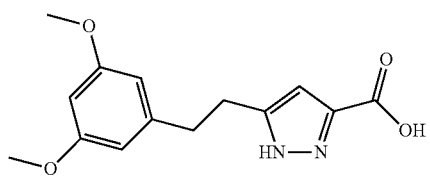 [SMILES: COc1cc(CCc2cc(C(=O)O)n[nH]2)cc(OC)c1]

5(3)-[2-(3,5-Dimethoxyphenyl)ethyl]-1H-pyrazole-3(5)-carboxylic acid ethyl ester (Compound P4, 2.0 g, 6.57 mmol) was dissolved in 25 ml of methanol, then 25 ml of 2M solution of sodium hydroxide were added. The reaction was carried out at ambient temperature for 20 hours. Methanol was evaporated, and then 60 ml of water were added. Obtained aqueous solution was brought to pH=2 with 1M hydrochloric acid. Precipitated solid was filtered, washed with water (20 ml) and toluene (20 ml). 1.385 g of the title compound in the form of a white solid were obtained (yield 76.3%)

MS-ESI: (m/z) calculated for $C_{14}H_{15}N_2O_6$ [M−H]⁻: 275.10, found 275.1.

¹H NMR (300 Hz DMSO-d6): δ 12.57 (bs, 1H), 6.39 (d, J=2.4 Hz, 2H), 6.29 (t, J=2.4 Hz, 1H), 6.16 (s, 1H), 3.70 (s, 6H), 3.46 (bs, 1H), 2.80 (m, 2H), 2.51 (m, 2H) ppm.

Compound P6: (3,4-dinitrophenyl)methanol

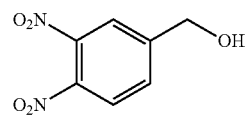 [SMILES: O=[N+]([O-])c1ccc(CO)cc1[N+](=O)[O-]]

To the solution of 3,4-dinitrobenzoic acid (10.0 g, 46.2 mmol) in THF (30 ml) cooled to −78° C. 1M solution of borane-THF complex in THF (92.4 ml) was added dropwise for 45 minutes. The reaction mixture was slowly warmed to 0° C., and then stirred at ambient temperature for 2 hours. The reaction mixture changed its color into dark green. Stirring was continued overnight. To the reaction mixture 4 ml of the acetic acid-water mixture (1:1, v/v) were added dropwise (during addition gas was liberated, the mixture warmed-up, and turned yellow). The mixture was concentrated, and the residue poured onto saturated sodium hydrogencarbonate solution with ice. The whole was extracted with ethyl acetae (3×50 ml). Organic phases were combined, washed with saturated sodium hydrogencarbonate and brine, and dried over solid Na₂SO₄. After evaporation of the solvent a brown oil was obtained that solidified to a dark-yellow solid (quantitative yield). The product was used for further reaction without purification.

MS-ESI: (m/z) calculated for $C_7H_6ClN_2O_5$ [M+Cl]⁻: 232.99, found 233.0.

Compound P7: 3,4-dinitrobenzyl methanesulphonate

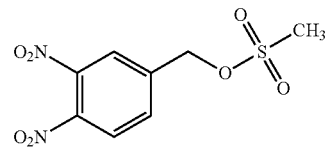 [SMILES: CS(=O)(=O)OCc1ccc([N+](=O)[O-])c([N+](=O)[O-])c1]

To the mixture of 3,4-dinitrophenyl)methanol (Compound P6, 3.0 g, 15.1 mmol) and triethylamine (3.17 ml, 22.7 mmol) in DCM (50 ml) cooled in water/ice bath methanesulphonic acid chloride (1.41 ml, 18.2 mmol) was added dropwise for 10 minutes. The reaction mixture was stirred at 0° C. for 1.5 hours. The progress of the reaction was monitored by TLC analysis (system: heptane/ethyl acetate, 1/2). Saturated ammonium chloride solution (40 ml) was added to the reaction mixture. Yellow solid precipitated. Water was added until dissolution of the solid. The solvent was evaporated and residual aqueous phase was extracted with ethyl acetate (2×100 ml). Organic phases were combined and dried over solid Na₂SO₄. After concentration 4.092 g of the brown oil were obtained (yield 97.9%).

¹H NMR (500 MHz, CDCl₃) δ 7.99 (d, J=8.3 Hz, 1H), 7.97 (d, J=0.8 Hz, 1H), 7.81 (dd, J=8.0 Hz, J=0.8 Hz, 1H), 5.36 (s, 2H), 3.15 (s, 3H) ppm.

$^{13}$C NMR (125 MHz, CDCl$_3$) δ 140.7, 132.2, 125.7, 124.1, 67.2, 38.2 ppm.

Compound P8:
(3,4-Dinitrophenyl)(morpholin-4-yl)methanone

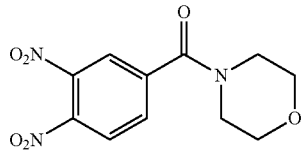 [SMILES: O=C(c1ccc([N+](=O)[O-])c([N+](=O)[O-])c1)N1CCOCC1]

To the solution of 3,4-dinitrobenzoic acid (2.0 g, 9.43 mmol) in 20 ml of THF 100 μl of dry DMF (1.41 mmol), and then thionyl chloride (0.97 ml, 12.4 mmol) were added. The mixture was maintained at reflux for 2.5 hours. Then the reaction mixture was cooled to 0° C. and triethylamine was slowly added dropwise (1.97 ml, 14.1 mmol) at the temperature not exceeding 5° C. Then morpholine (1.44 ml, 16.5 mmol) was added dropwise at 10° C. The progress of the reaction was monitored by TLC (system: heptane/ethyl acetate, 1/1). 30 ml of water was added to precipitate a solid that was filtered and dried. 2.458 g of the title compound were obtained in the form of a beige solid (yield 92.7%).

MS-ESI: (m/z) calculated for C$_{11}$H$_2$N$_3$O$_6$ [M+H]$^+$: 282.07, found 282.

$^1$H NMR (500 Hz CDCl$_3$): δ 8.00-7.98 (m, 2H), 7.80-7.78 (m, 1H), 3.81 (m, 4H), 3.68 (m, 2H), 3.43 (m, 2H) ppm.

Compound P9: 4-(3,4-Dinitrobenzyl)morpholine

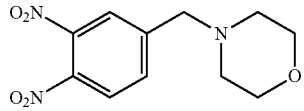 [SMILES: O=[N+]([O-])c1ccc(CN2CCOCC2)cc1[N+](=O)[O-]]

To the solution of sodium borohydride (0.218 g, 5.75 mmol) in 22 ml of dry tetrahydrofuran cooled to 0° C. boron trifluoride etherate (0.816 g, 5.75 mmol) was added. The reaction was carried out under flow of argon. (Caution: egzothermic reaction, evolution of hydrogen.) (3,4-dinitrophenyl)(morpholin-4-yl)methanone (Compound P8, 0.763 g, 2.71 mmol) was added to the mixture. The reaction was carried out at ambient temperature for 3 hours. 5 ml of methanol were added to the reaction mixture and the whole was heated to reflux and maintained at that temperature for further 20 minutes. The progress of the reaction was monitored by TLC (system: heptane/ethyl acetate, 9/1). Product was purified by chromatography on silicagel (system: heptane/ethyl acetate, 2/1+0.5% triethylamine). 0.438 g of the title compound in the form of a yellow oil (yield 60.4%) were obtained.

MS-ESI: calculated for C$_{11}$H$_{12}$N$_3$O$_5$ [M-H]$^-$: 266.07, found 266.0.

$^1$H NMR (500 Hz CDCl$_3$): δ 7.93-7.90 (m, 2H), 7.74-7.72 (m, 1H), 3.74 (t, J=5 Hz, 4H), 3.63 (s, 2H), 2.49 (t, J=5 Hz, 4 Hz) ppm.

Compound P10: 4-(3,4-Diaminobenzyl)morpholine

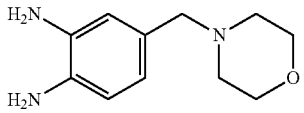

4-(3,4-Dinitrobenzyl)morpholine (Compound P9, 0.149 g, 0.56 mmol) was dissolved in 2.5 ml of ethyl acetate, and then 8 ml of ethanol were added. The suspension of 10% palladium on active carbon (0.40 g) in ethanol was added. The reaction of reduction of nitro groups was carried out overnight under hydrogen atmosphere. The progress of the reaction was monitored by TLC (system: ethyl acetate/methanol, 2/1). The reaction mixture was filtered through celite, and the solvent was evaporated. The title compound obtained in the amount of 0.114 g (yield 98.6%) was used for subsequent reaction without further purification.

$^1$H NMR (500 Hz CDCl$_3$): 6.70 (m, 1H), 6.32 (m, 2H), 3.70 (t, J=3 Hz, 4H), 3.45 (s, 2H), 3.43 (bs, 4H), 2.45-2.38 (m, 4H) ppm.

$^{13}$C NMR (75 Hz CDCl$_3$): 134.6, 133.7, 129.5, 121.1, 117.6, 116.5, 66.9, 63.3, 53.5 ppm.

Compound P11:
(3,4-Diaminophenyl)(morpholin-4-yl)methanone

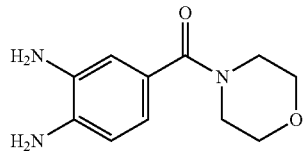 [SMILES: Nc1ccc(C(=O)N2CCOCC2)cc1N]

The compound was obtained by the method analogous to that described for Compound P10. Starting from (3,4-dinitrophenyl)(morpholin-4-yl)methanone (Compound P8, 0.390 g, 1.390 mmol), and using 0.255 g of 10% palladium on active carbon in the solution in 10 ml of ethanol and 8 ml of ethyl acetate 0.261 g of the title product were obtained in the form of a brown solid, which was used for subsequent reaction without purification.

Compound P12:
3,4-Dinitro-N-(tetrahydro-2H-pyran-4-yl)benzamide

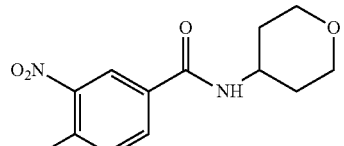

The compound was obtained by the method analogous to that described for Compound P8. Starting from 3,4-dinitrobenzoic acid (1.54 g, 7.11 mmol) and 4-aminotetrahydropyran (1.28 g, 12.40 mmol) 0.700 g of the title product in the form of a yellow solid were obtained (yield 33.4%).

MS-ESI: (m/z) calculated for $C_{12}H_{12}N_3O_6$ [M−H]⁻: 294.07, found 294.0.

¹H NMR (500 MHz, DMSO-d6) δ 8.84 (d, J=7.3 Hz, 1H), 8.62 (m, 1H), 8.38 (d, J=8.4 Hz, 1H), 8.34 (d, J=8.4 Hz, 1H), 4.08-3.98 (m, 1H), 3.89 (d, J=10.4 Hz, 2H), 3.40 (t, J=11.0 Hz, 2H), 1.81-1.79 (m, 2H), 1.62-1.54 (m, 2H) ppm.

Compound P13:
3,4-Diamino-N-(tetrahydro-2H-pyran-4-yl)benzamide

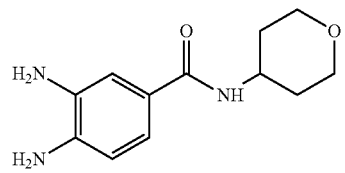

The compound was obtained by the method analogous to that described for Compound P10. Starting from 3,4-dinitro-N-(tetrahydro-2H-pyran-4-yl)benzamide (Compound P12, 0.253 g, 0.857 mmol), and using 0.200 g of 10% palladium on active carbon in the solution in 5 ml ethanol and 8 ml of ethyl acetate, 0.183 g of the solid title product were obtained, and used for subsequent reaction without purification.

Compound P14:
N-[2-(Morpholin-4-yl)ethyl]-3,4-dinitrobenzamide

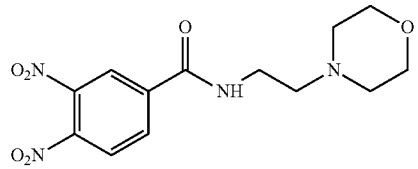 [SMILES: O=C(NCCN1CCOCC1)c1ccc([N+](=O)[O-])c([N+](=O)[O-])c1]

The compound was obtained by the method analogous to that described for Compound P8. Starting from 3,4-dinitrobenzoic acid (1.51 g, 6.98 mmol) and 4-morpholinoethaneamine (1.61 g, 12.1 mmol), 1.060 g of the title product in the form of an orange oil were obtained (yield 46.9%).

MS-ESI: (m/z) calculated $C_{13}H_{15}N_4O_6$ [M−H]⁻: 323.10, found 323.1.

¹H NMR (500 MHz, DMSO-d6) δ 8.95-8.93 (m, 1H), 8.59 (s, 1H), 8.35 (s, 2H), 3.61-3.53 (m, 4H), 3.43 (dd, J=12.7, 6.6 Hz, 2H), 2.50-2.48 (m, 2H), 2.43-2.41 (m, 4H) ppm.

Compound P15:
3,4-Diamino-N-[2-(morpholin-4-yl)ethyl]benzamide

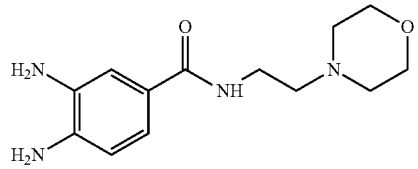

The compound was obtained by the method analogous to that described for Compound P10. Starting from N-[2-(morpholin-4-yl)ethyl]-3,4-dinitrobenzamide (Compound P14, 0.322 g, 0.993 mmol), and using 0.200 g of 10% palladium on active carbon in the solution in 5 ml of ethanol, 0.236 g of a grey solid containing the title product were obtained, and used without purification for subsequent reaction.

Compound P16: (3,4-Dinitrophenyl)(4-ethylpiperazin-1-yl)methanone

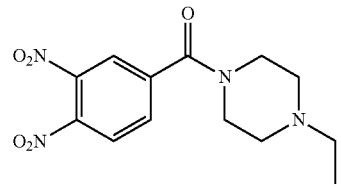 [SMILES: CCN1CCN(C(=O)c2ccc([N+](=O)[O-])c([N+](=O)[O-])c2)CC1]

The compound was obtained by the method analogous to that described for Compound P8. Starting from 3,4-dinitrobenzoic acid (2.00 g, 9.43 mmol) and 1-ethylpiperazine (1.87 g, 16.4 mmol), 2.29 g of the title product were obtained in the form of an orange oil (yield 78.8%).

MS-ESI: (m/z) calculated for $C_{13}H_{16}N_4O_5$ [M−H]⁻: 307.10, found 307.1.

¹H NMR (500 MHz, CDCl₃) δ 7.97 (dd, J=8.3, 4.9 Hz, 2H), 7.78 (dd, J=8.2, 1.6 Hz, 1H), 3.83 (s, 2H), 3.47-3.38 (m, 2H), 2.60-2.46 (m, 3H), 1.11 (t, J=7.2 Hz, 6H) ppm.

Compound P17:
1-(3,4-Dinitrobenzyl)-4-ethylpiperazine

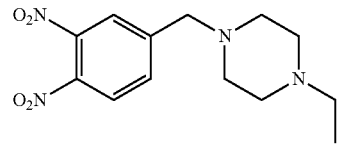 [SMILES: CCN1CCN(Cc2ccc([N+](=O)[O-])c([N+](=O)[O-])c2)CC1]

The compound was obtained by the method analogous to that described for Compound P9. Starting from (3,4-dinitrophenyl)(4-ethylpiperazin-1-yl)methanone (Compound P16, 0.418 g, 1.36 mmol), sodium borohydride (0.111 g, 2.87 mmol) and boron trifluoride etherate (0.408 g, 2.87 mmol) in 10 ml of dry THF, 0.260 g of the title product in the form of an orange oil were obtained (yield 65.2%).

MS-ESI: (m/z) calculated for $C_{13}H_{19}N_4O_4$ [M+H]⁺: 295.14, found 295.1.

¹H NMR (500 MHz, DMSO-d6) δ 8.20 (d, J=8.3 Hz, 1H), 8.10 (m, 1H), 7.88 (d, J=8.3 Hz, 1H), 3.66 (s, 2H), 2.42 (s, 8H), 2.33 (q, J=7.2 Hz, 2H), 0.98 (t, J=7.2 Hz, 3H) ppm.

Compound P18: 4-[(4-Ethylpiperazin-1-yl)methyl]benzene-1,2-diamine

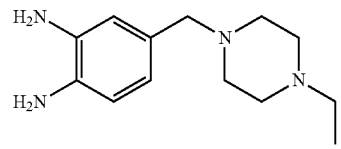

The compound was obtained by the method analogous to that described for Compound P10. Starting from 1-(3,4-dinitrobenzyl)-4-ethylpiperazine (Compound P17, 0.197 g, 0.669 mmol), and using 0.050 g of 10% palladium on active carbon in the solution in 12 ml of ethanol and 3 ml of ethyl acetate, 0.190 g of the solid with the title product were obtained, and used without purification for subsequent reactions.

Compound P19: (3,4-Diaminophenyl)(4-ethylpiperazin-1-yl)methanone

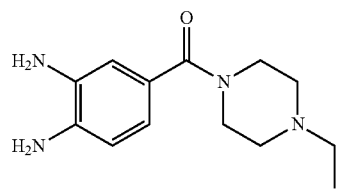

The compound was obtained by the method analogous to that described for Compound P10. Starting from (3,4-dinitrophenyl)(4-ethylpiperazin-1-yl)methanone (Compound P16, 0.300 g, 0.993 mmol), and using 0.080 g of 10% palladium on active carbon in the solution in 4 ml of ethanol and 16 ml of ethyl acetate, 0.154 g of a grey solid containing title product were obtained, and used without purification for subsequent reaction.

Compound P20: (3,4-Dinitrophenyl)(4-methylpiperazin-1-yl)methanone

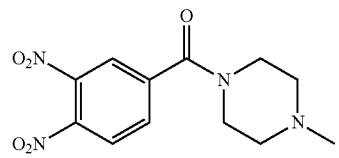 [SMILES: CN1CCN(C(=O)c2ccc([N+](=O)[O-])c([N+](=O)[O-])c2)CC1]

The compound was obtained by the method analogous to that described for Compound P8. Starting from 3,4-dinitrobenzoic acid (1.50 g, 6.93 mmol) and 1-methylpiperazine (1.22 g, 12.1 mmol), 0.734 g of the title product in the form of a yellow solid were obtained (yield 36.0%).

MS-ESI: (m/z) calculated for $C_{12}H_{15}N_4O_5$ $[M+H]^+$: 295.10, found 295.1.

$^1$H NMR 500 MHz, DMSO-d6) δ 8.31-8.28 (d, J=8.3 Hz 1H), 8.27 (d, J=1.6 Hz, 1H), 7.98 (dd, J=8.2, 1.7 Hz, 1H), 3.64 (m, 1H), 3.29 (m, 1H), 2.39 (m, 1H), 2.27 (m, 2H), 2.20 (s, 2H) ppm.

Compound P21: 1-(3,4-Dinitrobenzyl)-4-methylpiperazine

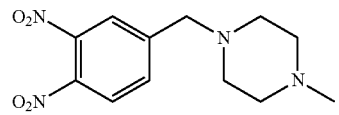

The compound was obtained by the method analogous to that described for Compound P9. Starting from (3,4-dinitrophenyl)(4-methylpiperazin-1-yl)methanone (Compound P20, 0.318 g, 1.08 mmol), sodium borohydride (0.088 g, 2.29 mmol) and boron trifluoride etherate (0.325 g, 2.29 mmol) in 10 ml of dry THF, 0.140 g of the title product in the form of an orange oil were obtained (yield 46.2%).

MS-ESI: (m/z) calculated for $C_{12}H_{17}N_4O_4$ $[M+H]^+$: 281.12, found 281.1.

$^1$H NMR (500 MHz, DMSO-d6) δ 8.20 (d, J=8.3 Hz, 1H), 8.11 (m, 1H), 7.87 (d, J=8.3 Hz, 1H), 3.66 (s, 2H), 2.48-2.26 (m, 8H), 2.19 (s, 3H) ppm.

Compound P22: 4-[(4-Methylpiperazin-1-yl)methyl]benzene-1,2-diamine

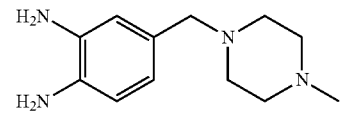 [SMILES: CN1CCN(Cc2ccc([N+](=O)[O-])c([N+](=O)[O-])c2)CC1]

The compound was obtained by the method analogous to that described for Compound P10. Starting from 1-(3,4-dinitrobenzyl)-4-methylpiperazine (Compound P21, 0.127 g, 0.453 mmol), and using 0.040 g of 10% palladium on active carbon in the solution of 8 ml ethanol and 2 ml of ethyl acetate, 0.100 g of the solid with the title product were obtained, and used without purification for subsequent reactions.

Compound P23: (3,4-Diaminophenyl)(4-methylpiperazin-1-yl)methanone

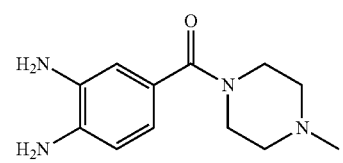

The compound was obtained by the method analogous to that described for Compound P10. Starting from (3,4-dinitrophenyl)(4-methylpiperazin-1-yl)-methanone (Compound P20, 0.275 g, 0.935 mmol), and using 0.200 g of 10% palladium on active carbon in the solution of 5 ml ethanol and 7 ml of ethyl acetate, 0.243 g of a violet solid with the title product were obtained, and used without purification for subsequent reactions.

Compound P24: [(3R,5S)-3,5-dimethylpiperazin-1-yl](3,4-dinitrophenyl)methanone

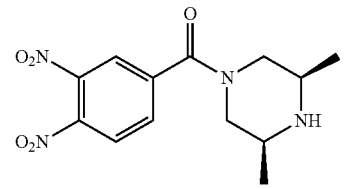 [SMILES: C[C@@H]1CN(C(=O)c2ccc([N+](=O)[O-])c([N+](=O)[O-])c2)C[C@H](C)N1]

The compound was obtained by the method analogous to that described for Compound P8. Starting from 3,4-dinitrobenzoic acid (0.200 g, 0.943 mmol) and cis-2,6-dimethylpiperazine (0.198 g, 1.70 mmol), 0.222 g of the title product in the form of a yellow solid were obtained (yield 76.4%).

MS-ESI: (m/z) calculated for $C_{13}H_{17}N_4O_5$ [M+H]$^+$: 309.12, found 309.1.

$^1$H NMR (500 MHz, CDCl$_3$) δ 7.98 (d, J=8.2 Hz, 1H), 7.95 (d, J=1.6 Hz, 1H), 7.76 (dd, J=8.2, 1.7 Hz, 1H), 4.57 (d, J=11.6 Hz, 1H), 3.36 (d, J=10.0 Hz, 1H), 2.97-2.88 (m, 1H), 2.87-2.73 (m, 2H), 2.44 (t, J=10.8 Hz, 1H), 1.87 (s, 1H), 1.16 (s, 3H), 1.02 (s, 3H) ppm.

Compound P25: (3R,5S)-1-(3,4-Dinitrobenzyl)-3,5-dimethylpiperazine

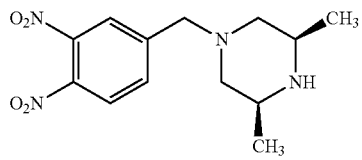

To the solution of 3,4-dinitrobenzyl methanesulphonate (Compound P7, 0.498 g, 1.80 mmol) in DCM (5 ml) at 0° C. triethylamine (0.503 ml, 3.61 mmol) and subsequently cis-2,6-dimethylpiperazine (0.315 g, 2.70 mmol) were added. The reaction mixture was stirred at 0° C. for 2 hours. The progress of the reaction was monitored by TLC (system: chloroform/methanol, 95/5). The reaction mixture was diluted with DCM (50 ml) and washed with water (2×50 ml), aqueous phases were combined and extracted with DCM (2×50 ml). Organic phases were combined, washed with brine and dried over Na$_2$SO$_4$. After evaporation of the solvents a brown oil was obtained that was purified by chromatography on silicagel (system: chloro-form/methanol 5%→10% gradient). 0.283 g of the title compound in the form of a brown oil were obtained (yield 53.3%)

MS-ESI: (m/z) calculated for $C_{13}H_{19}N_4O_4$ [M+H]$^+$: 295.14, found 295.1, for $C_{13}H_{17}N_4O_4$ [M−H]$^-$: 293.12, found 293.1.

Compound P26: 4-{[(3R,5S)-3,5-Dimethylpiperazin-1-yl]methyl}benzene-1,2-diamine

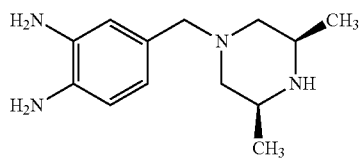 [SMILES: C[C@@H]1CN(Cc2ccc([N+](=O)[O-])c([N+](=O)[O-])c2)C[C@H](C)N1]

The compound was obtained by the method analogous to that described for Compound P10. Starting from (3R,5S)-1-(3,4-dinitrobenzyl)-3,5-dimethylpiperazine (Compound P25, 0.280 g, 0.951 mmol), and using 0.192 g of 10% palladium on active carbon in the solution in 15 ml ethanol, 0.160 g of a solid of the title product were obtained, and used without purification for subsequent reactions.

Compound P27: (3,4-Diaminophenyl)[(3R,5S)-3,5-dimethylpiperazin-1-yl]methanone

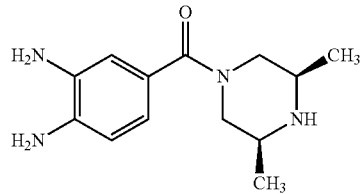 [SMILES: C[C@@H]1CN(C(=O)c2ccc(N)c(N)c2)C[C@H](C)N1]

The compound was obtained by the method analogous to that described for Compound P10. Starting from [(3R,5S)-3,5-dimethylpiperazin-1-yl](3,4-dinitro-phenyl)methanone (Compound P24, 0.350 g, 1.14 mmol), and using 0.130 g of 10% palladium on active carbon in the solution in 40 ml of ethanol and 10 ml of ethyl acetate, 0.231 g of a solid of the title product were obtained, and used without purification for subsequent reactions.

Compound P28: (3,4-Dinitrophenyl)(piperidin-1-yl)methanone

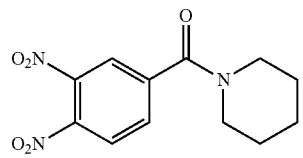 [SMILES: O=C(c1ccc([N+](=O)[O-])c([N+](=O)[O-])c1)N1CCCCC1]

The compound was obtained by the method analogous to that described for Compound P8. Starting from 3,4-dinitrobenzoic acid (0.500 g, 2.36 mmol) and piperidine (0.442 g, 5.19 mmol), 0.130 g of the title product in the form of a yellow solid were obtained (yield 19.7%).

MS-ESI: (m/z) calculated for $C_{12}H_{13}N_3O_5$ [M+H]$^+$: 280.09, found 280.1.

Compound P29: 1-(3,4-Dinitrobenzyl)piperidine

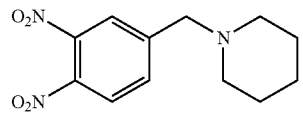 [SMILES: O=[N+]([O-])c1ccc(CN2CCCCC2)cc1[N+](=O)[O-]]

The compound was obtained by the method analogous to that described for Compound P25. Starting from 3,4-dinitrobenzyl methanesulphonate (Compound P7, 0.600 g, 2.17 mmol), triethylamine (0.605 ml, 4.34 mmol) and piperidine (0.462 g, 5.43 mmol) in 5 ml of dry DCM, 0.220 g of the title product in the form of an orange solid were obtained (yield 38.2%).

MS-ESI: (m/z) calculated for $C_{12}H_{16}N_3O_4$ [M+H]$^+$: 266.11, found 266.1.

Compound P30:
4-(Piperidin-1-ylmethyl)benzene-1,2-diamine

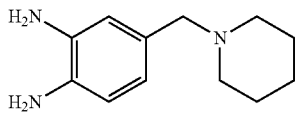

The compound was obtained by the method analogous to that described for Compound P10. Starting from 1-(3,4-dinitrobenzyl)piperidine (Compound P29, 0.170 g, 0.641 mmol), and using 0.120 g of 10% palladium on active carbon in the solution in 10 ml of ethanol, 0.190 g of a solid title product were obtained, and used without purification for subsequent reactions.

Compound P31:
(3,4-Diaminophenyl)(piperidin-1-yl)methanone

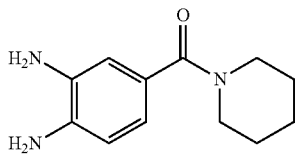

The compound was obtained by the method analogous to that described for Compound P10. Starting from (3,4-dinitrophenyl)(piperidin-1-yl)methanone (Compound P28, 0.110 g, 0.394 mmol), and using 0.040 g of 10% palladium on active carbon in the solution in 16 ml of ethanol and 4 ml of ethyl acetate, 0.080 g of a solid title product were obtained, and used without purification for subsequent reactions.

Compound P32: 1-(1-(3,4-Dinitrobenzyl)piperidin-4-yl)-4-methylpiperazine

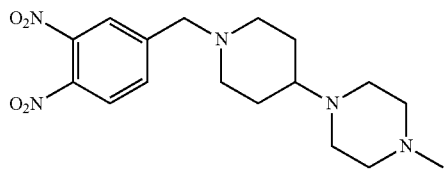

The compound was obtained by the method analogous to that described for Compound P25. Starting from 3,4-dinitrobenzyl methanesulphonate (Compound P7, 0.537 g, 1.94 mmol), triethylamine (0.535 ml, 3.89 mmol) and 1-methyl-4-(piperidin-4-yl)piperazine (0.535 g, 2.92 mmol) in 5 ml of dry DCM, 0.550 g of the title product in the form of a yellow oil were obtained (yield 77.8%).

MS-ESI: (m/z) calculated for $C_7H_{26}N_5O_4$ $[M+H]^+$: 364.19, found 364.2.

Compound P33: 4-((4-(4-Methylpiperazin-1-yl)piperidin-1-yl)methyl)benzene-1,2-diamine

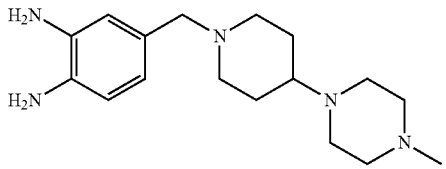 [SMILES: CN1CCN(C2CCN(Cc3ccc([N+](=O)[O-])c([N+](=O)[O-])c3)CC2)CC1]

The compound was obtained by the method analogous to that described for Compound P10. Starting from 1-(1-(3,4-dinitrobenzyl)piperidin-4-yl)-4-methylpiperazine (Compound P32, 0.550 g, 1.51 mmol), and using 0.120 g of 10% palladium on active carbon in the solution in 8 ml of ethanol and 2 ml of ethyl acetate, 0.450 g of a solid containing title product were obtained, and used without purification for subsequent reactions.

Compound P34: 1'-(3,4-Dinitrobenzyl)-1,4'-bipiperidine

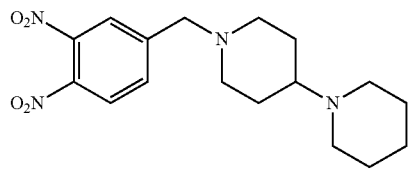 [SMILES: O=[N+]([O-])c1ccc(CN2CCC(N3CCCCC3)CC2)cc1[N+](=O)[O-]]

The compound was obtained by the method analogous to that described for Compound P25. Starting from 3,4-dinitrobenzyl methanesulphonate (Compound P7, 0.506 g, 1.83 mmol), triethylamine (0.511 ml, 3.66 mmol) and 1,4'-bipiperidine (0.472 g, 2.75 mmol) in 5 ml of dry DCM, 0.550 g of the title product in the form of a light-brown oil were obtained (yield 86.2%).

MS-ESI: (m/z) calculated for $C_{17}H_{25}N_4O_4$ $[M+H]^+$: 349.18, found 349.2.

$^1$H NMR (500 MHz, DMSO d-6) δ 8.27 (d, J=2.2 Hz, 1H), 7.98 (dd, J=8.9, 2.2 Hz, 1H), 7.32 (d, J=8.9 Hz, 1H), 4.29 (dd, J=6.0 Hz, 2H), 3.70 (dd, J=6.2 Hz, 2H), 3.40-3.34 (m, 2H), 2.96 (dd, J=11.6 Hz, 2H), 2.46 (s, 4H), 1.87-1.82 (m, 3H), 1.81-1.75 (m, J=11.7 Hz, 2H), 1.54 (dt, J=9.3, 7.5 Hz, 2H), 1.50-1.47 (m, 4H), 1.41-1.35 (m, J=5.2 Hz, 2H) ppm.

Compound P35: 4-(1,4'-Bipiperidin-1'-ylmethyl)benzene-1,2-diamine

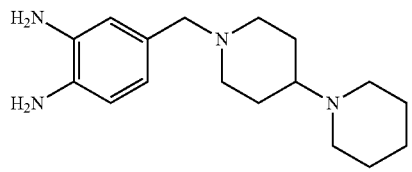

The compound was obtained by the method analogous to that described for Compound P10. Starting from 1'-(3,4-dinitrobenzyl)-1,4'-bipiperidine (Compound P34, 0.100 g, 0.287 mmol), and using 0.105 g of 10% palladium on active carbon in the solution in 8 ml of ethanol and 2 ml of ethyl acetate, 0.130 g of a solid containing title product were obtained, and used without purification for subsequent reactions.

Compound P36: (3,4-Dinitrophenyl)(4-(2-morpholinoethyl)piperazin-1-yl)methanone

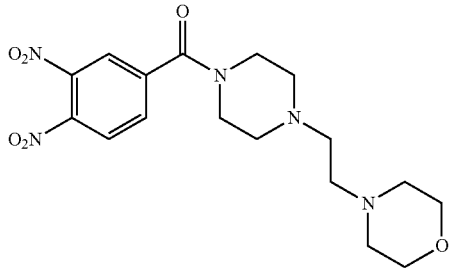 [SMILES: O=C(c1ccc([N+](=O)[O-])c([N+](=O)[O-])c1)N1CCN(CCN2CCOCC2)CC1]

The compound was obtained by the method analogous to that described for Compound P8. Starting from 3,4-dinitrobenzoic acid (1.48 g, 6.84 mmol) and 1-[2-(morpholin-4-yl)ethyl]piperazine (2.45 g, 11.9 mmol), 0.895 g of the title product in the form of a crystallizing yellow oil were obtained (yield 33.3%).

MS-ESI: calculated for $C_{17}H_{24}N_5O_6$ [M+H]: 394.17, found 394.1.

$^1$H NMR (500 MHz, DMSO-d6) δ 8.29 (d, J=8.2 Hz, 1H), 8.26 (m, 1H), 7.97 (d, J=8.2, 1H), 3.62 (s, 2H), 3.58-3.52 (m, 4H), 3.28 (s, 2H), 2.50-2.48 (m, 2H), 2.47-2.45 (m, 2H), 2.43-2.41 (m, 2H), 2.39-2.38 (m, 6H) ppm.

Compound P37: (3,4-Diaminophenyl)(4-(2-morpholinoethyl)piperazin-1-yl)-methanone

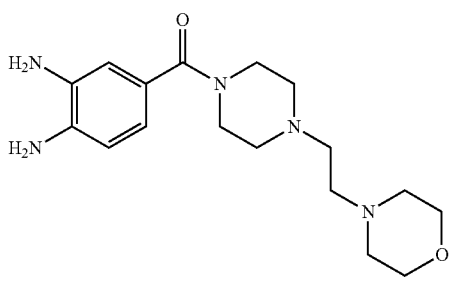

The compound was obtained by the method analogous to that described for Compound P10. Starting from (3,4-dinitrophenyl)(4-(2-morpholinoethyl)piperazin-1-yl)methanone (Compound P36, 0.302 g, 0.768 mmol), and using 0.200 g of 10% palladium on active carbon in the solution in 5 ml of ethanol and 5 ml of ethyl acetate, 0.294 g of a solid title product were obtained, and used without purification for subsequent reactions.

Compound P38: 4-(2-(4-(3,4-Dinitrobenzyl)piperazin-1-yl)ethyl)morpholine

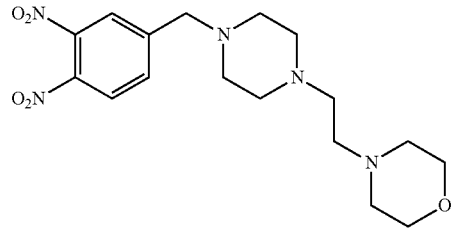

The compound was obtained by the method analogous to that described for Compound P9. Starting from (3,4-dinitrophenyl)(4-(2-morpholinoethyl)piperazin-1-yl)methanone (Compound P36, 0.319 g, 0.811 mmol), sodium borohydride (0.066 g, 1.72 mmol) and boron trifluoride etherate (0.244 g, 1.72 mmol) in 10 ml of dry THF, 0.286 g of the title product in the form of an orange oil were obtained (yield 93.0%).

MS-ESI: calculated for $C_{17}H_{26}N_5O_5$ [M+H]: 380.19, found 380.2.

Compound P39: 4-(2-(4-(3,4-Dinitrobenzyl)piperazin-1-yl)ethyl)morpholine

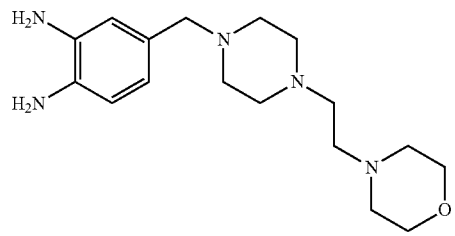 [SMILES: O=[N+]([O-])c1ccc(CN2CCN(CCN3CCOCC3)CC2)cc1[N+](=O)[O-]]

The compound was obtained by the method analogous to that described for Compound P10. Starting from 4-(2-(4-(3,4-dinitrobenzyl)piperazin-1-yl)ethyl)-morpholine (Compound P38, 0.360 g, 1.04 mmol), and using 0.070 g of 10% palladium on active carbon in the solution in 5 ml of ethanol, 0.303 g of a solid title product were obtained, and used without purification for subsequent reactions.

Compound P40: 2-(4-(3,4-Dinitrobenzyl)piperazin-1-yl)-N,N-dimethylacetamide

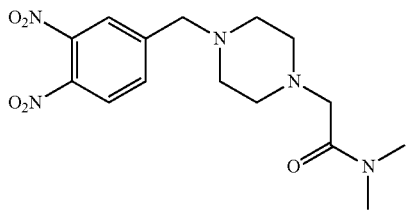 [SMILES: CN(C)C(=O)CN1CCN(Cc2ccc([N+](=O)[O-])c([N+](=O)[O-])c2)CC1]

Starting from 3,4-dinitrobenzyl methanesulphonate (Compound P7, 0.500 g, 1.81 mmol), triethylamine (0.378 ml, 2.72 mmol) and N—N-dimethyl-2-piperazin-1-yl-acetamide (0.489 g, 2.72 mmol) in 10 ml of dry DCM, 0.570 g of the title product in the form of a brown oil were obtained (yield 89.6%).

MS-ESI: (m/z) calculated for $C_{15}H_{22}N_5O_5$ [M+H]$^+$: 352.16, found 352.1.

Compound P41: 2-(4-(3,4-Diaminobenzyl)piperazin-1-yl)-N,N-dimethylacetamide

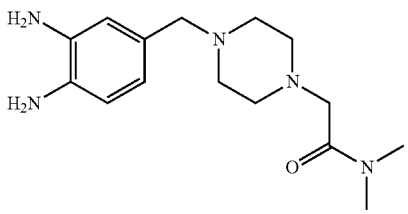

The compound was obtained by the method analogous to that described for Compound P10. Starting from 2-(4-(3,4-dinitrobenzyl)piperazin-1-yl)-N,N-dimethylacetamide (Compound P40, 0.570 g, 1.62 mmol), and using 0.150 g of 10% palladium on active carbon in the solution in 5 ml of ethanol and 10 ml of ethyl acetate, 0.470 g of a solid title product were obtained, and used without purification for subsequent reactions.

Compound P42: 5-(Morpholin-4-yl)-2-nitroaniline

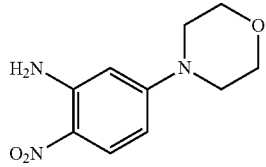

To the flask 2-amino-3-nitro-6-chloropyridine (1.50 g, 8.47 mmol), potassium carbonate (1.30 g, 9.32 mmol) and morpholine (10.5 ml, 119 mmol) were added. The reaction was carried out under argon flow at 130° C. overnight. The progress of the reaction was monitored by TLC (system: heptane/ethyl acetate, 1/1). The mixture was cooled to room temperature and poured into the ice-water. A precipitated yellow solid was filtered and dried. 1.789 g of the title product were obtained (yield 94.2%).

MS-ESI: (m/z) calculated for $C_{10}H_{14}N_3O_3$ [M+H]$^+$: 224.10, found 224.1.

$^1$H NMR (500 MHz, DMSO-d6) δ 7.83 (d, J=9.7 Hz, 1H), 7.27 (s, 2H), 6.39 (dd, J=9.8, 2.7 Hz, 1H), 6.23 (d, J=2.6 Hz, 1H), 3.79-3.64 (m, 4H), 3.28 (dd, J=16.0, 11.0 Hz, 5H) ppm.

$^{13}$C NMR (125 MHz, DMSO-d6) δ 155.18, 148.17, 127.05, 123.21, 105.07, 97.56, 65.65, 46.37 ppm.

Compound P43: 4-(morpholin-4-yl)benzene-1,2-diamine

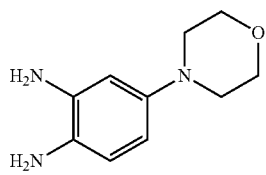

The compound was obtained by the method analogous to that described for Compound P10. Starting from 5-(morpholin-4-yl)-2-nitroaniline (Compound P42, 0.300 g, 1.340 mmol), and using 0.060 g of 10% palladium on active carbon in the solution in 30 ml of ethanol and 30 ml of ethyl acetate, 0.150 g of a dark-brown solid with title product were obtained, and used without purification for subsequent reaction.

Compound P44: 5-(4-Methylpiperazin-1-yl)-2-nitroaniline

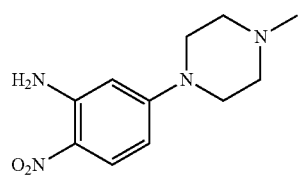 [SMILES: CN1CCN(c2ccc([N+](=O)[O-])c(N)c2)CC1]

The compound was obtained by the method analogous to that described for Compound P42. Starting from 5-chloro-2-nitroaniline (1.50 g, 8.69 mmol), potassium carbonate (1.35 g, 9.74 mmol) and 1-methylpiperazine (2.61 g, 26.1 mmol) in 2 ml of DMF, 2.021 g of the title product in the form of a yellow solid were obtained (yield 98.4%).

MS-ESI: calculated for $C_{11}H_{15}N_4O_2$ [M−H]$^-$: 235.12, found 235.1.

$^1$H NMR (500 MHz, DMSO-d6) δ 7.81 (d, J=9.8 Hz, 1H), 7.27 (s, 2H), 6.39 (dd, J=9.8, 2.7 Hz, 1H), 6.23 (d, J=2.7 Hz, 1H), 3.37 (s, 7H), 3.33-3.28 (m, 4H), 2.52 (tt, J=3.5, 1.8 Hz, 1H), 2.39 (dd, J=12.3, 7.2 Hz, 4H), 2.20 (d, J=11.9 Hz, 3H) ppm.

$^{13}$C NMR (125 MHz, DMSO-d6) δ 154.97, 148.30, 127.13, 122.90, 105.38, 97.50, 54.13, 46.13, 45.60 ppm.

Compound P45: 4-(4-Methylpiperazin-1-yl)benzene-1,2-diamine

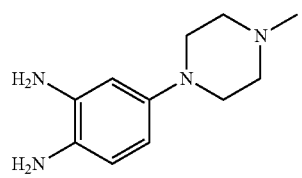

The compound was obtained by the method analogous to that described for Compound P10. Starting from 5-(4-methylpiperazin-1-yl)-2-nitroaniline (Compound P44, 0.389 g, 1.68 mmol) and 0.090 g of 10% palladium on active carbon in the solution in 5 ml of ethanol and 7 ml of ethyl acetate, 0.124 g of a dark-brown solid with title product were obtained, and used without purification for subsequent reaction.

Compound P46:
5-(4-Ethylpiperazin-1-yl)-2-nitroaniline

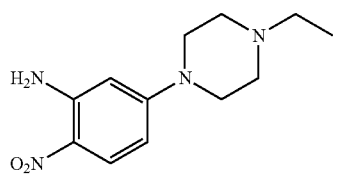

The compound was obtained by the method analogous to that described for Compound P42. Starting from 5-chloro-2-nitroaniline (1.50 g, 8.69 mmol), potassium carbonate (1.32 g, 9.56 mmol) and 1-ethylpiperazine (1.98 g, 17.3 mmol) w 2 ml of DMF, 2.021 g of the title product in the form of a yellow solid were obtained (yield 92.9%).

MS-ESI: (m/z) calculated for $C_{12}H_{19}N_4O_2$ [M+H]$^+$: 251.15, found 251.1.

$^1$H NMR (300 MHz, CDCl$_3$) δ 7.81 (d, J=9.6 Hz, 1H), 6.39 (dd, J=9.6 Hz; 2.1 Hz 1H), 6.22 (d, J=2.1 Hz, 1H), 3.31 (dd, J=4.5 Hz, 4.8 Hz, 4H), 2.44 (dd, J=4.5 Hz, 4.8 Hz, 4H) 2.35 (q, J=7.2 Hz, 2H), 1.02 (t, J=7.2 Hz, 3H) ppm.

Compound P47:
4-(4-Ethylpiperazin-1-yl)benzene-1,2-diamine

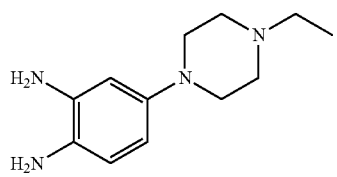 [SMILES: CCN1CCN(c2ccc([N+](=O)[O-])c(N)c2)CC1]

The compound was obtained by the method analogous to that described for Compound P10. Starting from 5-(4-ethylpiperazin-1-yl)-2-nitroaniline (Compound P46, 0.390 g, 1.56 mmol) and 0.085 g of 10% palladium on active carbon in the solution in 10 ml of ethanol, 0.100 g of a dark-brown solid with title product were obtained, and used without purification for subsequent reaction.

Compound P48: 5-[(3R,5S)-3,5-dimethylpiperazin-1-yl]-2-nitroaniline

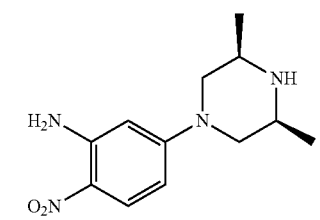 [SMILES: C[C@@H]1CN(c2ccc([N+](=O)[O-])c(N)c2)C[C@H](C)N1]

The compound was obtained by the method analogous to that described for Compound P42. Starting from 5-chloro-2-nitroaniline (0.800 g, 4.64 mmol), potassium carbonate (0.705 g, 5.10 mmol) and cis-2,6-dimethylpiperazine (1.620 g, 13.9 mmol) in 5 ml of DMF, 1.144 g of the title product in the form of a yellow solid were obtained (yield 98.6%).

MS-ESI: (m/z) calculated for $C_{12}H_{19}N_4O_2$ [M+H]$^+$: 251.15, found 251.1.

Compound P49: 4-[(3R,5S)-3,5-Dimethylpiperazin-1-yl]benzene-1,2-diamine

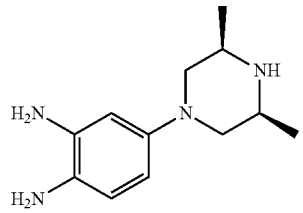 [SMILES: C[C@@H]1CN(c2ccc(N)c(N)c2)C[C@H](C)N1]

The compound was obtained by the method analogous to that described for Compound P10. Starting from 5-[(3R,5S)-3,5-dimethylpiperazin-1-yl]-2-nitroaniline (Compound P48, 0.200 g, 0.799 mmol) and 0.045 g of 10% palladium on active carbon in the solution in 10 ml of ethanol and 5 ml of ethyl acetate, 0.193 g of a dark-brown solid with title product were obtained, and used without purification for subsequent reaction.

Compound P50: 5-{4-[2-(Diethylamino)ethyl]piperazin-1-yl}-2-nitroaniline

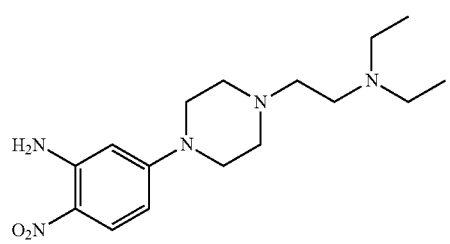 [SMILES: CCN(CC)CCN1CCN(c2ccc([N+](=O)[O-])c(N)c2)CC1]

The compound was obtained by the method analogous to that described for Compound P42. Starting from 5-chloro-2-nitroaniline (0.387 g, 2.20 mmol), potassium carbonate (0.304 g, 2.20 mmol) and 1-(2-diethylaminoethyl)piperazine (0.500 g, 2.64 mmol) in 2 ml of DMF, 0.199 g of the title product in the form of a yellow solid were obtained (yield 28.1%).

MS-ESI: calculated for $C_{16}H_{28}N_5O_2$ [M−H]$^-$: 322.22, found 322.2.

$^1$H NMR (500 MHz, DMSO) δ 7.80 (d, J=9.8 Hz, 1H), 7.27 (s, 2H), 6.38 (dd, J=9.8, 2.5 Hz, 1H), 6.21 (d, J=2.4 Hz, 1H), 3.33-3.24 (m, 4H), 2.58-2.52 (m, 6H), 2.50-2.47 (m, 4H), 2.43-2.37 (m, 2H), 0.96 (t, J=7.1 Hz, 6H). ppm.

Compound P51: 4-{4-[2-(Diethylamino)ethyl]piperazin-1-yl}benzene-1,2-diamine

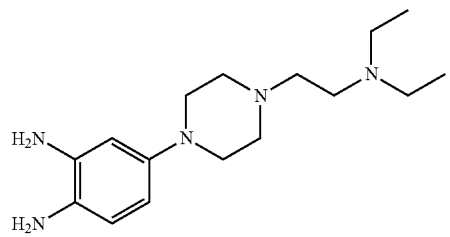

The compound was obtained by the method analogous to that described for Compound P10. Starting from 5-{4-[2-(diethylamino)ethyl]piperazin-1-yl}-2-nitroaniline (Compound P50, 0.199 g, 6.19 mmol) and 0.040 g of 10% palladium on active carbon in the solution in 15 ml of ethanol, 0.180 g of a dark-brown solid with title product were obtained, and used without purification for subsequent reaction.

Compound P52: 2-[4-(3-Amino-4-nitrophenyl)piperazin-1-yl]-1-(morpholin-4-yl)-ethanone

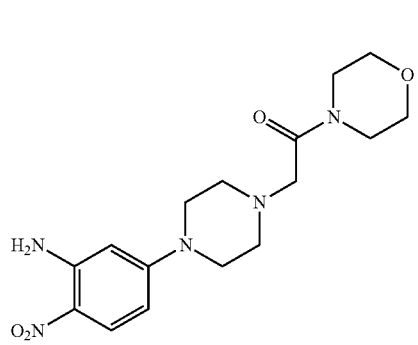 [SMILES: Nc1cc(N2CCN(CC(=O)N3CCOCC3)CC2)ccc1[N+](=O)[O-]]

The compound was obtained by the method analogous to that described for Compound P42. Starting from 3-chloro-2-nitroaniline (0.288 g, 1.64 mmol), potassium carbonate (0.249 g, 1.80 mmol) and 1-(morpholin-4-yl)-2-(piperazin-1-yl)ethanone (1.008 g, 4.91 mmol), 0.386 g of the title product in the form of a yellow solid were obtained (yield 70.4%).

MS-ESI: (m/z) calculated for $C_{16}H_{26}N_5O_3$ [M+H]$^+$: 350.18, found 350.2.

$^1$H NMR (500 MHz, DMSO-d6) δ 7.81 (d, J=9.7 Hz, 1H), 7.24 (s, 2H), 6.38 (dd, J=9.7, 2.3 Hz, 1H), 6.22 (d, J=2.1 Hz, 1H), 3.61-3.51 (m, 8H), 3.44 (s, 2H), 3.32 (s, 2H), 3.21 (s, 2H), 2.50 (s, 4H) ppm.

Compound P53: 2-[4-(3,4-Diaminophenyl)piperazin-1-yl]-1-(morpholin-4-yl)-ethanone

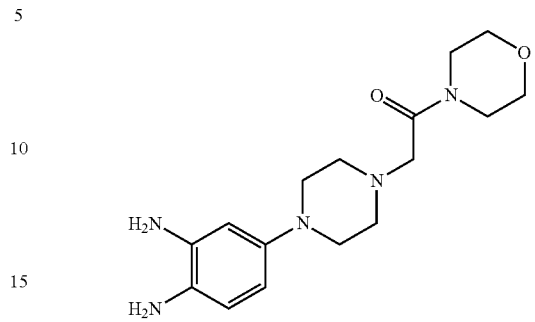

The compound was obtained by the method analogous to that described for Compound P10. Starting from 2-[4-(3-amino-4-nitrophenyl)piperazin-1-yl]-1-(morpholin-4-yl)ethanone (Compound P52, 0.250 g, 0.745 mmol) and 0.062 g of 10% palladium on active carbon in the solution in 10 ml of ethanol, 0.150 g of the title product in the form of a dark-brown solid were obtained, and used without purification for subsequent reactions.

Compound P54: 3-(Morpholin-4-yl)-2-nitroaniline

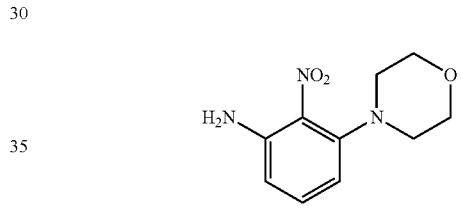

The compound was obtained by the method analogous to that described for Compound P42. Starting from 3-chloro-2-nitroaniline (1.50 g, 8.52 mmol), potassium carbonate (1.30 g, 9.37 mmol) and morpholine (10.4 g, 119 mmol), 1.778 g of the title product in the form of a red solid were obtained (yield 93.5%).

MS-ESI: (m/z) calculated for $C_{10}H_{13}N_3O_3Na$ [M+Na]$^+$: 246.08, found 246.0.

Compound P55: 3-(Morpholin-4-yl)benzene-1,2-diamine

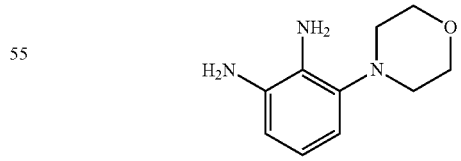

The compound was obtained by the method analogous to that described for Compound P10. Starting from 3-(morpholin-4-yl)-2-nitroaniline (Compound P54, 0.421 g, 1.89 mmol) and 0.090 g of 10% palladium on active carbon in the solution in 5 ml of ethanol and 5 ml of ethyl acetate, 0.100 g of a dark-brown solid with the title product were obtained, and used without purification for subsequent reaction.

Compound P56: 3-[(3R,5S)-3,5-Dimethylpiperazin-1-yl]-2-nitroaniline

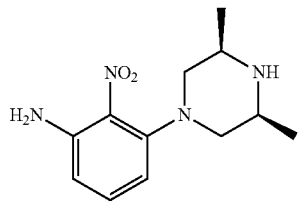 [SMILES: C[C@@H]1CN(c2cccc(N)c2[N+](=O)[O-])C[C@H](C)N1]

The compound was obtained by the method analogous to that described for Compound P42. Starting from 3-chloro-2-nitroaniline (1.50 g, 8.52 mmol), potassium carbonate (1.30 g, 9.37 mmol) and cis-2,6-dimethylpiperazine (2.98 g, 25.6 mmol), 1.007 g of the title product in the form of a dark-brown solid were obtained (yield 47.2%).

MS-ESI: calculated for $C_{12}H_{19}N_4O_2$ [M+H]$^+$: 251.15, found 251.1.

$^1$H NMR (500 MHz, DMSO-d6) δ 7.09 (t, J=8.1 Hz, 1H), 6.53-6.45 (m, 1H), 6.32 (dd, J=8.0, 0.9 Hz, 1H), 5.84 (s, 1H), 2.91-2.84 (m, 1H), 2.82-2.71 (m, 1H), 2.50 (dt, J=3.6, 1.8 Hz, 1H), 2.21 (t, J=10.7 Hz, 1H), 0.92 (d, J=6.3 Hz, 3H) ppm.

Compound P57: 3-[(3R,5S)-3,5-Dimethylpiperazin-1-yl]benzene-1,2-diamine

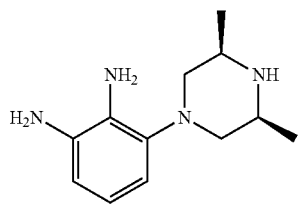 [SMILES: C[C@@H]1CN(c2cccc(N)c2N)C[C@H](C)N1]

The compound was obtained by the method analogous to that described for Compound P10. Starting from 3-[(3R,5S)-3,5-dimethylpiperazin-1-yl]-2-nitroaniline (Compound P56, 0.212 g, 0.842 mmol), 0.043 g of 10% palladium on active carbon in the solution in 10 ml of ethanol, 0.199 g of a solid title product were obtained, and used without purification for subsequent reactions.

Compound P58: 2-Nitro-3-[4-(propan-2-yl)piperazin-1-yl]aniline

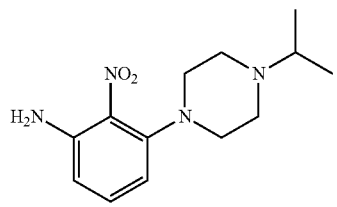

The compound was obtained by the method analogous to that described for Compound P42. Starting from 3-chloro-2-nitroaniline (0.459 g, 2.61 mmol), potassium carbonate (0.368 g, 2.66 mmol) and 1-isopropylpiperazine (1.00 g, 0.741 mmol), 0.602 g of the title product in the form of a red solid were obtained (yield 91.9%).

MS-ESI: (m/z) calculated for $C_{13}H_{21}N_4O_2$ [M+H]$^+$: 265.16, found 265.1.

$^1$H NMR (500 MHz, DMSO-d6) δ 7.10 (dd, J=8.1 Hz, 1H), 6.52 (dd, J=8.3, 1.0 Hz, 1H), 6.35 (dd, J=8.0, 1.0 Hz, 1H), 5.83 (s, 2H), 2.85 (dd, J=17.4, 12.8 Hz, 4H), 2.68-2.60 (m, 1H), 2.47 (dd, 4H), 0.97 (d, J=6.5 Hz, 6H).

Compound P59: 3-[4-(Propan-2-yl)piperazin-1-yl]benzene-1,2-diamine

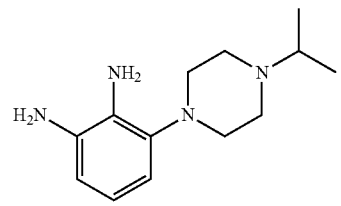 [SMILES: CC(C)N1CCN(c2cccc(N)c2[N+](=O)[O-])CC1]

The compound was obtained by the method analogous to that described for Compound P10. Starting from 2-nitro-3-[4-(propan-2-yl)piperazin-1-yl]aniline (Compound P58, 0.602 g, 2.57 mmol) and 0.090 g of 10% palladium on active carbon in the solution in 5 ml of ethanol and 5 ml of ethyl acetate, 0.166 g of a dark-brown solid with the title product were obtained, and used without purification for subsequent reaction.

Compound P60: 3-(1,4'-Bipiperidin-1'-yl)-2-nitroaniline

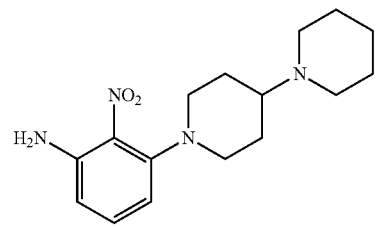 [SMILES: Nc1cccc(N2CCC(N3CCCCC3)CC2)c1[N+](=O)[O-]]

The compound was obtained by the method analogous to that described for Compound P42. Starting from 3-chloro-2-nitroaniline (1.50 g, 8.52 mmol), potassium carbonate (4.41 g, 31.9 mmol) and 1,4'-bipiperidine (4.50 g, 26.2 mmol), 1.007 g of the title product in the form of a dark-brown solid were obtained (yield 47.2%).

MS-ESI: calculated for $C_{12}H_{25}N_4O_2$ [M+H]$^+$: 305.20, found 305.2.

Compound P61: 3-(1,4'-Bipiperidin-1'-yl)benzene-1,2-diamine

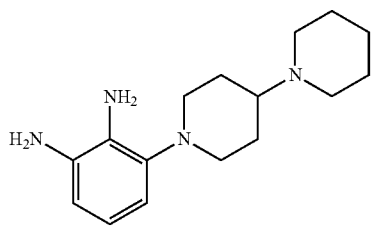

The compound was obtained by the method analogous to that described for Compound P10. Starting from 3-(1,4'-bipiperidin-1'-yl)-2-nitroaniline (Compound P60, 0.220 g, 0.723 mmol), and using 0.044 g of 10% palladium on active carbon in the solution in 10 ml of ethanol, 0.117 g of a solid title product were obtained, and used without purification for subsequent reactions.

Compound P62: 3-{4-[2-(Morpholin-4-yl)ethyl]piperazin-1-yl}-2-nitroaniline

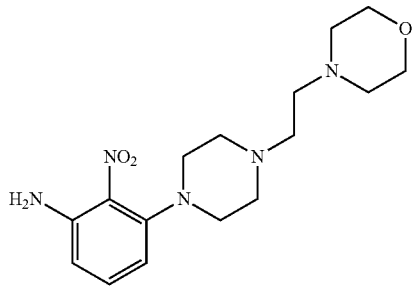 [SMILES: Nc1cccc(N2CCN(CCN3CCOCC3)CC2)c1[N+](=O)[O-]]

The compound was obtained by the method analogous to that described for Compound P42. Starting from 3-chloro-2-nitroaniline (0.342 g, 1.98 mmol), potassium carbonate (0.312 g, 2.26 mmol) and 4-[2-(piperazin-1-yl)ethyl]-morpholine (0.502 g, 2.26 mmol), 0.350 g of the title product in the form of an orange solid were obtained (yield 50.5%).

MS-ESI: (m/z) calculated for $C_{16}H_{24}N_5O_4$ $[M+H]^+$: 350.18, found 350.2.

$^1$H NMR (500 MHz, DMSO) δ 7.10 (dd, 12H), 6.52 (d, 1H), 6.35 (d, 1H), 5.84 (s, 2H), 3.55 (dd, 4H), 2.85 (dd, 4H), 2.46-2.33 (m, 12H) ppm.

Compound P63: 3-{4-[2-(Morpholin-4-yl)ethyl]piperazin-1-yl}benzene-1,2-diamine

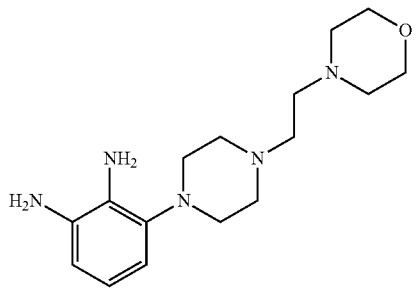 [SMILES: Nc1cccc(N2CCN(CCN3CCOCC3)CC2)c1N]

The compound was obtained by the method analogous to that described for Compound P10. Starting from 3-{4-[2-(morpholin-4-yl)ethyl]piperazin-1-yl}-2-nitroaniline (Compound P62, 0.200 g, 0.745 mmol) and 0.062 g of 10% palladium on active carbon in the solution in 10 ml of ethanol, 0.150 g of the title product were obtained in the form of a dark-brown solid, which was used without purification for subsequent reactions.

MS-ESI: (m/z) calculated for $C_{16}H_{26}N_5O_2$ $[M+H]^+$: 320.20, found 320.2.

Compound P64: 5-{1-[2-(Morpholin-4-yl)ethyl]-1H-pyrazol-4-yl}-2-nitroaniline

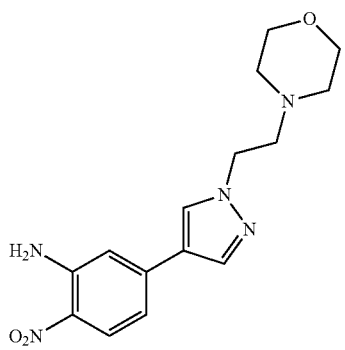 [SMILES: Nc1cc(-c2cnn(CCN3CCOCC3)c2)ccc1[N+](=O)[O-]]

5-Chloro-2-nitroaniline (0.128 g, 0.744 mmol), pinacol ester of 1-(2-morpholinoethyl)-1H-pyrazole-4-boronic acid (0.343 g, 1.12 mmol) and tetrakis(triphenyl-phosphine)palladium(0) (0.086 g, 0.074 mmol) were placed in the Schlenk-type flask under argon flow and then the system was degassed. After 20 minutes under argon flow to the flask 10.5 ml of degassed 2-methoxyethyl methyl ether and 0.744 ml of degassed 2M $Na_2CO_3$ solution were added dropwise. The reaction was carried out under reflux. The progress of the reaction was monitored by TLC analysis (system: heptane/ethyl acetate, 5/4). Ether was evaporated and ethyl acetate added. The mixture was filtered through celite layer. The filtrate was added with water and extracted with ethyl acetate (3×50 ml). Combined organic phases were washed with brine and dried over anhydrous $Na_2SO_4$. A brown oil was obtained after filtration and concentration, and was purified by chromatography on silicagel (system: dichlorometan/methanol, 9/1). 0.152 g of a crystallizing oil were obtained (yield 64.3%).

MS-ESI: (m/z) calculated for $C_{15}H_{20}N_5O_3$ $[M+H]^+$: 318.16, found 318.2.

$^1$H NMR (300 MHz, DMSO-d6) δ 8.26 (s, 1H), 7.96 (d, 1H), 7.87 (s, 1H), 7.44 (bs, 2H), 7.14 (d, 1H), 6.86 (dd, J=9.0, 0.9 Hz, 1H), 4.27 (t, 2H), 3.56-3.53 (m, 4H), 2.73 (t, 2H), 2.43-2.40 (m, 4H).

Compound P65: 4-{1-[2-(Morpholin-4-yl)ethyl]-1H-pyrazol-4-yl}benzene-1,2-diamine

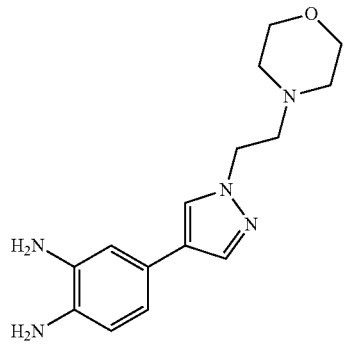 [SMILES: Nc1ccc(-c2cnn(CCN3CCOCC3)c2)cc1N]

The compound was obtained by the method analogous to that described for Compound P10. Starting from 5-{1-[2-(morpholin-4-yl)ethyl]-1H-pyrazol-4-yl}-2-nitroaniline (Compound P66, 0.136 g, 0.429 mmol) and 0.032 g of 10% palladium on active carbon in the solution in 10 ml of ethanol and 2 ml of ethyl acetate, 0.168 g of the title product were obtained, and used without purification for subsequent reactions.

Compound P66: 5-[5-(Morpholin-4-ylmethyl)thiophen-2-yl]-2-nitroaniline

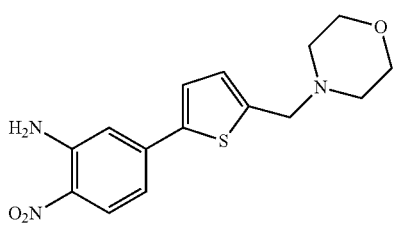 [SMILES: Nc1cc(-c2ccc(CN3CCOCC3)s2)ccc1[N+](=O)[O-]]

The compound was obtained by the method analogous to that described for Compound P64. Starting from 5-chloro-2-nitroaniline (0.186 g, 1.08 mmol), pinacol ester of 5-(4-morpholinylmethyl)thiophene-2-boronic acid (0.510 g, 1.62 mmol) and tetrakis(triphenylphosphine)palladium(0) (0.125 g, 0.074 mmol) in the solution in 15 ml of (2-methoxy)ethylmethyl ether with the addition of 1 ml of 2M Na$_2$CO$_3$ solution, 0.210 g of the title product in the form of a dark-orange solid were obtained (yield 61.0%).

MS-ESI: (m/z) calculated for C$_{15}$H$_{16}$N$_3$O$_3$S [M–H]$^-$: 318.09, found 318.1.

$^1$H NMR (500 MHz, DMSO-d6) δ 7.98 (d, J=9.0 Hz, 1H), 7.47 (bs, 2H), 7.46 (d, J=3.7 Hz, 1H), 7.24 (d, J=2.0 Hz, 1H), 7.03 (d, J=3.7 Hz, 1H), 6.95 (dd, J=9.0, 2.0 Hz, 1H), 3.70 (s, 1H), 3.61-3.57 (m, 4H), 2.46-2.41 (m, 4H).

Compound P67: 4-[5-(Morpholin-4-ylmethyl)thiophen-2-yl]benzene-1,2-diamine

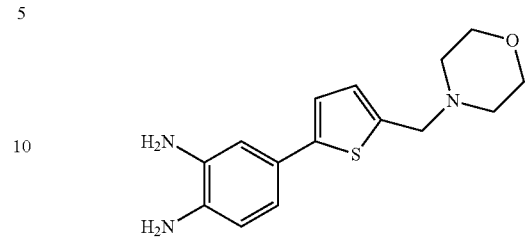

The compound was obtained by the method analogous to that described for Compound P10. Starting from 5-[5-(morpholin-4-ylmethyl)thiophen-2-yl]-2-nitroaniline (Compound P66, 0.210 g, 0.658 mmol) and 0.050 g of 10% palladium on active carbon in the solution in 10 ml of ethanol and 4 ml of ethyl acetate, 0.190 g of the title product were obtained in the form of a brown solid, which was used without purification for subsequent reactions.

Compound P68: 3'-(Morpholin-4-ylmethyl)-4-nitrobiphenyl-3-amine

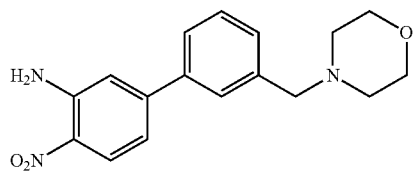 [SMILES: Nc1cc(-c2cccc(CN3CCOCC3)c2)ccc1[N+](=O)[O-]]

The compound was obtained by the method analogous to that described for Compound P64. Starting from 5-chloro-2-nitroaniline (0.190 g, 1.10 mmol), pinacol ester of 3-(4-methylmorpholino)benzenoboronic acid (0.511 g, 1.65 mmol) and tetrakis(triphenylphosphine)palladium(0) (0.127 g, 0.110 mmol) in the solution in 15 ml of (2-methoxy)ethylmethyl ether with the addition of 1.1 ml of 2M Na$_2$CO$_3$ solution, 0.277 g of the title product in the form of a yellow oil were obtained (yield 80.3%).

MS-ESI: (m/z) calculated for C$_{17}$H$_{18}$N$_3$O$_3$ [M–H]$^-$: 312.13 found 312.1.

$^1$H NMR (500 MHz, DMSO-d6) δ 8.05 (d, J=9.0 Hz, 1H), 7.65-7.52 (m, 3H), 7.48-7.45 (m, 3H), 7.39 (d, J=7.5 Hz, 1H), 7.31 (d, J=1.9 Hz, 1H), 6.93 (dd, J=9.0, 1.9 Hz, 1H), 3.59 (s, 4H), 3.54 (s, 2H), 2.45-2.29 (m, 4H).

Compound P69: 3'-(Morpholin-4-ylmethyl)biphenyl-3,4-diamine

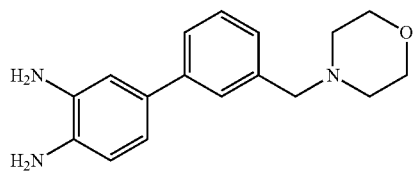

The compound was obtained by the method analogous to that described for Compound P10. Starting from 3'-(morpholin-4-ylmethyl)-4-nitrobiphenyl-3-amine (Compound P68, 0.185 g, 0.590 mmol) and 0.044 g of 10% palladium on active carbon in the solution in 7.5 ml of ethanol, 0.167 g of the title product were obtained in the form of a brown solid, which was used without purification for subsequent reactions.

Compound P70: (3'-Amino-4-nitrobiphenyl-4-yl) (morpholin-4-yl)methanone

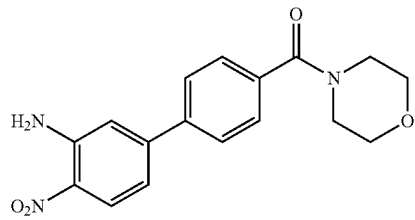 [SMILES: Nc1cc(-c2ccc(C(=O)N3CCOCC3)cc2)ccc1[N+](=O)[O-]]

The compound was obtained by the method analogous to that described for Compound P64. Starting from 5-chloro-2-nitroaniline (0.490 g, 2.84 mmol), 4-(morpholinocarbonyl)phenylboronic acid (1.020 g, 4.26 mmol) and tetrakis-(triphenylphosphine)palladium(0) (0.328 g, 0.284 mmol) in the solution in 40 ml of (2-methoxy)ethylmethyl ether with the addition of 2.8 ml of 2M $Na_2CO_3$ solution, 0.812 g of the title product in the form of a yellow oil were obtained (yield 87.4%).

MS-ESI: (m/z) calculated for $C_{17}H_{16}N_3O_4$ $[M-H]^-$: 326.11, found 326.1.

$^1$H NMR (500 MHz, DMSO-d6) δ 8.06 (d, J=9.0 Hz, 1H), 7.72 (d, J=8.4 Hz, 2H), 7.55 (d, J=8.4 Hz, 2H), 7.50 (bs, 2H), 7.33 (d, J=1.9 Hz, 1H), 6.96 (dd, J=9.0, 2.0 Hz, 1H), 3.77-3.34 (m, J=115.9 Hz, 8H).

Compound P71: (3',4'-Diaminobiphenyl-4-yl)(morpholin-4-yl)methanone

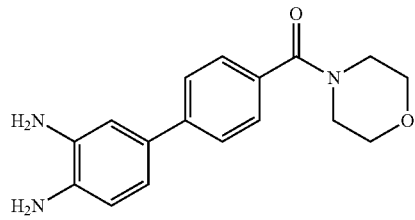

The compound was obtained by the method analogous to that described for Compound P10. Starting from (3'-amino-4'-nitrobiphenyl-4-yl)(morpholin-4-yl)-methanone (Compound P70), 0.200 g, 0.611 mmol) and 0.091 g of 10% palladium on active carbon in the solution in 10 ml of ethanol and 4 ml of ethyl acetate, 0.182 g of the title product were obtained in the form of a brown solid, which was used without purification for subsequent reactions.

Compound P72: 4'-(Morpholin-4-ylmethyl)-4-nitrobiphenyl-3-amine

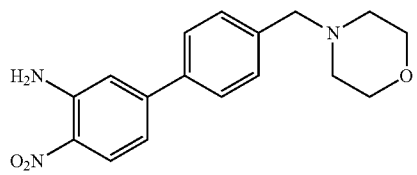

The compound was obtained by the method analogous to that described for Compound P64. Starting from 5-chloro-2-nitroaniline (0.164 g, 0.952 mmol), pinacol ester of 4-(4-morpholinomethyl)phenylboronic acid chlorohydrate (0.500 g, 1.43 mmol) and tetrakis(triphenylphosphine)palladium(0) (0.110 g, 0.095 mmol) in the solution in 15 ml of (2-methoxy)ethylmethyl ether with the addition of 2.37 ml of 2M $Na_2CO_3$ solution, 0.233 g of the title product in the form of an orange solid were obtained (yield 78.1%).

MS-ESI: (m/z) calculated for $C_{17}H_{18}N_3O_3$ $[M-H]^-$: 312.13, found 312.1.

$^1$H NMR (500 MHz, DMSO) δ 8.04 (d, J=9.0 Hz, 1H), 7.64-7.59 (m, 2H), 7.47 (bs, 2H), 7.44 (d, J=8.2 Hz, 2H), 7.29 (d, J=1.9 Hz, 1H), 6.93 (dd, J=9.0, 2.0 Hz, 1H), 3.64-3.56 (m, 4H), 3.51 (s, 2H), 2.41-2.35 (m, 4H).

Compound P73: 4'-(Morpholin-4-ylmethyl)biphenyl-3,4-diamine

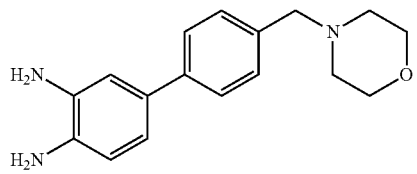 [SMILES: Nc1cc(-c2ccc(CN3CCOCC3)cc2)ccc1[N+](=O)[O-]]

The compound was obtained by the method analogous to that described for Compound P10. Starting from 4'-(morpholin-4-ylmethyl)-4-nitrobiphenyl-3-amine (Compound P72), 0.233 g, 0.744 mmol) and 0.056 g of 10% palladium on active carbon in the solution in 10 ml of ethanol and 4 ml of ethyl acetate, 0.210 g of a solid title product were obtained, and used without purification for subsequent reactions.

Compound P74: 4'-(Morpholin-4-yl)-4-nitrobiphenyl-3-amine

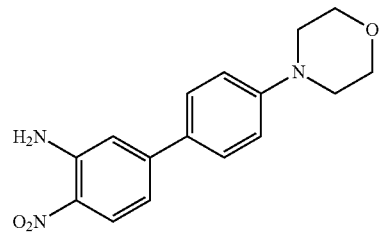

The compound was obtained by the method analogous to that described for Compound P64. Starting from 5-chloro-2-nitroaniline (0.200 g, 1.16 mmol), pinacol ester of 4-morpholinophenylboronic acid (0.513 g, 1.74 mmol) oraz tetrakis-(triphenylphosphine)palladium(0) (0.328 g, 0.284 mmol) in the solution in 16 ml of (2-methoxy)ethylmethyl ether with the addition of 1.6 ml of 2M $Na_2CO_3$ solution, 0.232 g of the title product in the form of a brown solid were obtained (yield 66.9%).

MS-ESI: (m/z) calculated for $C_{16}H_{16}N_3O_3$ $[M-H]^-$: 298.12, found 298.1.

$^1$H NMR (500 MHz, DMSO-d6) δ 7.99 (d, J=9.0 Hz, 1H), 7.57 (d, J=8.9 Hz, 2H), 7.42 (bs, 2H), 7.25 (d, J=2.0 Hz, 1H), 7.05 (d, J=8.9 Hz, 2H), 6.92 (dd, J=9.1, 2.0 Hz, 1H), 3.79-3.72 (m, 4H), 3.23-3.17 (m, 4H).

Compound P75:
4'-(Morpholin-4-yl)biphenyl-3,4-diamine

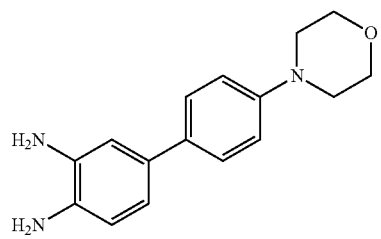 [SMILES: Nc1cc(-c2ccc(N3CCOCC3)cc2)ccc1[N+](=O)[O-]]

The compound was obtained by the method analogous to that described for Compound P10. Starting from 4'-(morpholin-4-yl)-4-nitrobiphenyl-3-amine (Compound P74, 0.232 g, 0.775 mmol) and 0.058 g of 10% palladium on active carbon in the solution in 10 ml of ethanol and 2 ml of ethyl acetate, 0.210 g of the title product were obtained in the form of a brown solid, which was used without purification for subsequent reactions.

Compound P76:
5-[6-(Morpholin-4-yl)pyridin-3-yl]-2-nitroaniline

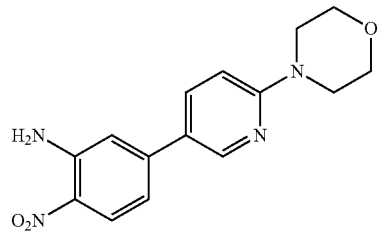 [SMILES: Nc1cc(-c2ccc(N3CCOCC3)nc2)ccc1[N+](=O)[O-]]

The compound was obtained by the method analogous to that described for Compound P64. Starting from 5-chloro-2-nitroaniline (0,200 g, 1.16 mmol), pinacol ester of 2-(morpholino)pyridin-5-ylboronic acid (0.525 g, 1.74 mmol) and tetrakis-(triphenylphosphine)palladium(0) (0.134 g, 0.116 mmol) in the solution in 16 ml of (2-methoxy)ethylmethyl ether with the addition of 1.2 ml of 2M $Na_2CO_3$ solution, 0.118 g of the title product in the form of an orange solid were obtained (yield 33.9%).

MS-ESI: calculated for $C_{15}H_{15}N_4O_3$ $[M-H]^-$: 299.11, found 299.1.

$^1$H NMR (500 MHz, DMSO-d6) δ 8.48 (d, J=2.5 Hz, 1H), 8.01 (d, J=3.5 Hz, 1H), 7.86 (dd, J=9.0, 2.6 Hz, 1H), 7.43 (bs, 2H), 7.24 (d, J=1.9 Hz, 1H), 6.98-6.92 (m, J=9.2 Hz, 2H), 3.75-3.68 (m, 4H), 3.57-3.51 (m, 4H).

Compound P77: 4-[6-(Morpholin-4-yl)pyridin-3-yl]benzene-1,2-diamine

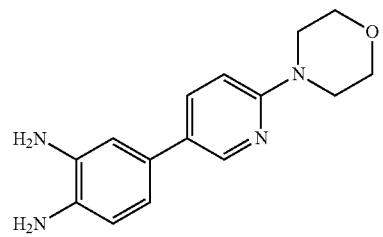

The compound was obtained by the method analogous to that described for Compound P10. Starting from 5-[6-(morpholin-4-yl)pyridin-3-yl]-2-nitroaniline (Compound P76, 0.115 g, 0.383 mmol) and 0.029 g of 10% palladium on active carbon in the solution in 13 ml of ethanol and 8 ml of ethyl acetate, 0.104 g of a mixture containing the title product were obtained in the form of a yellow solid, which was used without purification for subsequent reactions.

EXAMPLES

Compounds of the Invention

Example 1: 4-((2-(5(3)-(3,5-Dimethoxyphenethyl)-1H-pyrazol-3(5)-yl)-1H-benzo[d]-imidazol-5(6)-yl)methyl)morpholine

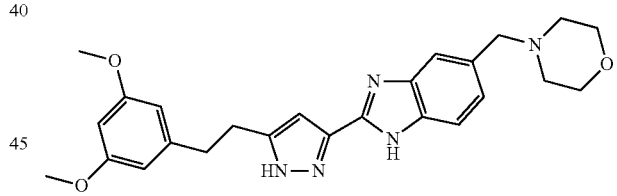

To the flask containing the solution of 5(3)-[2-(3,5-dimethoxyphenyl)ethyl]-1H-pyrazole-3(5)-carboxylic acid (Compound P5, 0.159 g, 0.58 mmol) in 2 ml of DMF under argon atmosphere, EDCl (0.121 g, 0.63 mmol), hydroxybenzotriazole (0.086 g, 0.63 mmol) and triethylamine (100 μl, 0.69 mmol) were added. After 30 minutes 4-(3,4-diaminobenzyl)morpholine (Compound P10, 0.131 g, 0.63 mmol) was added. The reaction was carried out at ambient temperature for 20 h. The solvent was evaporated under reduced pressure, and to the remaining brown oil 7.1 ml of acetic acid were added. Cyclization reaction was carried out at boiling temperature for 2 hours. The progress of the reaction was monitored by TLC (system: aceton/toluen, 4/1). After completion of the reaction acetic acid was evaporated. The residue was dissolved in chloroform and washed with saturated sodium hydrogencarbonate solution. Aqueous phase was extracted twice with chloroform. Combined organic layers were dried over anhydrous sodium sulphate. Product was purified by chromatography on silicagel column (system; chloroform/methanol. 99/1). After column chromatography the compound was crystallized from toluene. 0.145 g of the title compound in the form of creamy crystals were obtained (yield 56.3%).

MS-ESI: (m/z) calculated for $C_{25}H_{30}N_5O_3$ [M+H]$^+$: 448.23, found 448.2, for $C_{25}H_{29}N_5O_3Na$ [M+Na]$^+$: 470.23, found 470.2, dla $C_{25}H_{28}N_5O_3$ [M−H]$^−$: 446.22, found 446.2.

$^1$H NMR (500 MHz, CDCl$_3$): δ 7.40 (bs, 2H), 7.15 (m, 1H), 6.70 (bs, 1H), 6.22 (m, 3H), 3.64 (m, 10H), 3.50 (s, 2H), 2.77 (m, 4H), 2.39 (m, 4H) ppm.

$^{13}$C NMR (125 MHz, CDCl$_3$): δ 160.7, 142.9, 132.5, 124.0, 106.2, 103.3, 97.9, 66.9, 63.6, 55.1, 53.6, 35.2 ppm.

Example 2: (2-(5(3)-(3,5-Dimethoxyphenethyl)-1H-pyrazol-3(5)-yl)-1H-benzo[d]imidazol-5(6)-yl)(morpholino)methanone

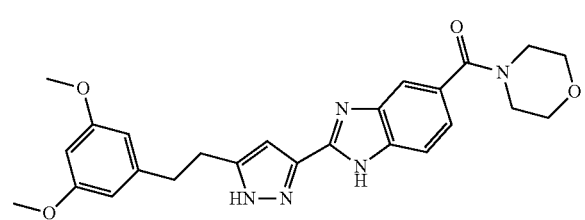 [SMILES: COc1cc(CCc2cc(-c3nc4cc(C(=O)N5CCOCC5)ccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.100 g, 0.362 mmol), EDCl (0.077 g, 0.402 mmol), hydroxybenzotriazole (0.054 g, 0.402 mmol), (3,4-diaminophenyl)(morpholin-4-yl)-methanone (Compound P11, 0.089 g, 0.402 mmol), 5 ml DMF and using 8 ml of acetic acid, 0.071 g of the title product in the form of a creamy solid were obtained (yield 42.5%).

MS-ESI: (m/z) calculated for $C_{25}H_{26}N_5O_4$ [M−H]$^−$: 460.20, found 460.2.

Example 3: 2-(5(3)-(3,5-Dimethoxyphenethyl)-1H-pyrazol-3(5)-yl)-N-(tetrahydro-2H-pyran-4-yl)-1H-benzo[d]imidazole-5(6)-carboxyamide

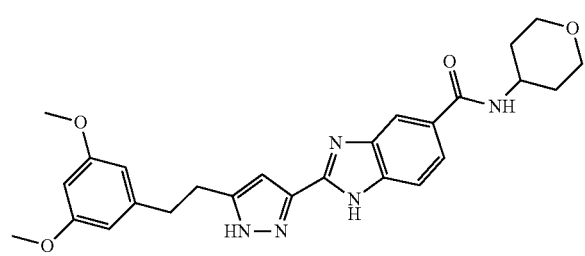 [SMILES: COc1cc(CCc2cc(-c3nc4cc(C(=O)NC5CCOCC5)ccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.100 g, 0.362 mmol), EDCl (0.077 g, 0.402 mmol), hydroxybenzotriazole (0.054 g, 0.402 mmol), 3,4-diamino-N-(tetrahydro-2H-pyran-4-yl)-benzamide (Compound P13, 0.094 g, 0.402 mmol) in 2 ml of DMF and using 5 ml of acetic acid, 0.085 g of the title product in the form of a yellow solid were obtained (yield 49.4%).

MS-ESI: (m/z) calculated for $C_{26}H_{28}N_5O_4$ [M−H]$^−$: 474.21, found 474.2.

$^1$H NMR (500 MHz, DMSO-d6) δ 13.07 (d, J=10.1 Hz, 1H), 12.87 (d, J=27.1 Hz, 1H), 8.28 (d, J=7.7 Hz, 0.5H), 8.21 (d, J=7.7 Hz, 0.5H), 8.15 (s, 0.5H), 7.94 (s, 0.5H), 7.69 (dd, J=24.0, 8.4 Hz, 1H), 7.59 (d, J=8.4 Hz, 0.5H), 7.43 (d, J=8.4 Hz, 0.5H), 6.65 (s, 1H), 6.40 (t, J=7.0 Hz, 2H), 6.31 (s, 1H), 4.07-3.97 (m, 1H), 3.87 (d, J=9.6 Hz, 2H), 3.69 (s, 6H), 3.37 (dd, J=11.7, 10.1 Hz, 2H), 3.01-2.94 (m, 2H), 2.91 (t, J=7.2 Hz, 2H), 2.49 (tt, J=3.6, 1.8 Hz, 4H) ppm.

$^{13}$C NMR (126 MHz, DMSO-d6) δ 166.56, 160.83, 149.90, 149.35, 146.18, 144.70, 143.69, 143.57, 136.90, 134.47, 129.27, 128.56, 122.43, 121.22, 118.32, 118.08, 111.53, 111.02, 106.83, 103.23, 103.17, 98.30, 66.70, 55.47, 46.26, 46.19, 35.11, 32.98, 26.76, 26.71 ppm.

Example 4: 2-(5(3)-(3,5-Dimethoxyphenethyl)-1H-pyrazol-3(5)-yl)-N-(3-morpholinopropyl)-1H-benzo[d]imidazole-5(6)-carboxyamide

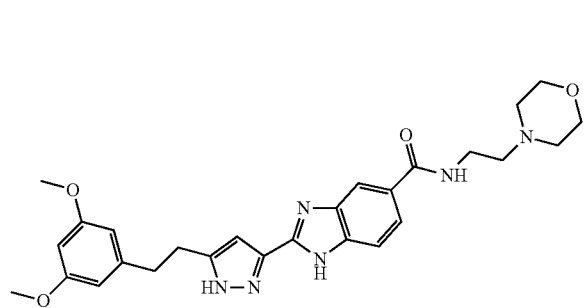 [SMILES: COc1cc(CCc2cc(-c3nc4cc(C(=O)NCCN5CCOCC5)ccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.150 g, 0.543 mmol), EDCl (0.116 g, 0.603 mmol), hydroxybenzotriazole (0.081 g, 0.603 mmol), 3,4-diamino-N-[2-(morpholin-4-yl)ethyl]-benzamide (Compound P15, 0.159 g, 0.603 mmol) in 2 ml of DMF and using 5 ml of acetic acid, 0.052 g of the title product in the form of a creamy solid were obtained (yield 19.0%).

MS-ESI: (m/z) calculated for $C_{27}H_{31}N_6O_4$ [M−H]$^−$: 503.24, found 503.2.

$^1$H NMR (500 MHz, CDCl$_3$) δ 7.99 (s, 1H), 7.63-7.29 (m, 2H), 6.70 (s, 1H), 6.36-6.05 (m, 3H), 3.92-3.22 (m, 12H), 3.11-2.73 (m, 4H), 2.49 (m, 6H) ppm.

$^{13}$C NMR (125 MHz, CDCl$_3$) δ 168.36, 160.73, 142.88, 128.82, 106.36, 103.58, 97.93, 66.30, 55.12, 53.18, 45.78, 35.97, 35.25, 29.66 ppm.

Example 5: 2-(5(3)-(3,5-Dimethoxyphenethyl)-1H-pyrazol-3(5)-yl)-5(6)-((4-ethylpiperazin-1-yl)methyl)-1H-benzo[d]imidazole

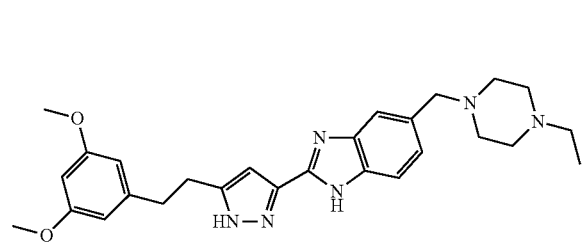 [SMILES: CCN1CCN(Cc2ccc3[nH]c(-c4cc(CCc5cc(OC)cc(OC)c5)[nH]n4)nc3c2)CC1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.224 g, 0.811 mmol), EDCl (0.173 g, 0.900 mmol), hydroxybenzotriazole (0.122 g, 0.900 mmol), 3,4-diamino-N-[2-(morpholin-4-yl)ethyl]-benzamide (Compound P18, 0.190 g, 0.811 mmol) in 6 ml of DMF and using 5 ml of acetic acid, 0.044 g of the title product in the form of white crystals were obtained (yield 11.4%).

MS-ESI: (m/z) calculated for $C_{27}H_{33}N_6O_2$ [M−H]⁻: 473.27, found 473.2.

¹H NMR (500 MHz, CDCl₃): δ 7.42 (s, 2H), 7.09 (s, 1H), 6.81 (s, 1H), 6.29 (d, J=14.4 Hz, 3H), 3.69 (s, 6H), 3.57 (s, 2H), 2.95 (d, J=43.7 Hz, 6H), 2.46 (dd, J=33.2, 25.8 Hz, 10H), 1.06 (t, J=7.0 Hz, 3H) ppm.

Example 6: (2-(5(3)-(3,5-Dimethoxyphenethyl)-1H-pyrazol-3(5)-yl)-1H-benzo[d]-imidazol-5(6)-yl)(4-ethylpiperazin-1-yl)methanone

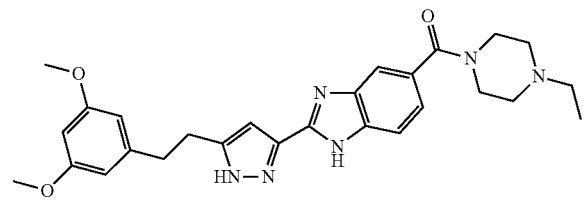 [SMILES: CCN1CCN(C(=O)c2ccc3[nH]c(-c4cc(CCc5cc(OC)cc(OC)c5)[nH]n4)nc3c2)CC1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.206 g, 0.744 mmol), EDCl (0.132 g, 0.688 mmol), hydroxybenzotriazole (0.093 g, 0.688 mmol), 4-(3,4-diaminobenzyl)morpholine (Compound P19, 0.154 g, 0.620 mmol) in 4 ml of DMF and using 6 ml of acetic acid, 0.075 g of the title product in the form of a white solid were obtained (yield 24.8%).

MS-ESI: (m/z) calculated for $C_{27}H_{33}N_6O_3$ [M+H]⁺: 489.26, found 489.2.

¹H NMR (500 MHz, CDCl₃) δ 7.65 (s, 2H), 7.17 (d, J=7.4 Hz, 1H), 6.81 (s, 1H), 6.37-6.20 (m, 3H), 3.80 (s, 2H), 3.70 (s, 6H), 3.51 (s, 2H), 3.04-2.79 (m, 4H), 2.57-2.30 (m, 6H), 1.07 (t, J=7.1 Hz, 3H) ppm.

Example 7: 2-(5(3)-(3,5-Dimethoxyphenethyl)-1H-pyrazol-3(5)-yl)-5(6)-((4-methyl-piperazin-1-yl)methyl)-1H-benzo[d]imidazole

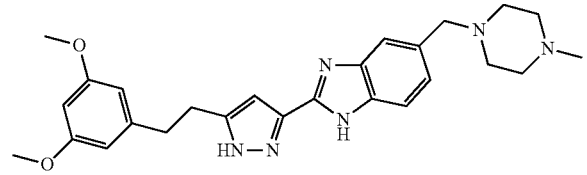

The compound was obtained by the method analogous to that described in Example 1. Starting from 5(3)-[2-(3,5-dimethoxyphenyl)ethyl]-1H-pyrazole-3(5)-carboxylic acid (Compound P5, 0.119 g, 0.431 mmol), EDCl (0.087 g, 0.454 mmol), hydroxybenzotriazole (0.031 g, 0.227 mmol), 4-[(4-methylpiperazin-1-yl)methyl]benzene-1,2-diamine (Compound P22, 0.100 g, 0.454 mmol) in 2 ml of DMF and using 5 ml of acetic acid, 0.030 g of the title product in the form of an amorphous yellow powder were obtained (yield 14.4%).

MS-ESI: (m/z) calculated for $C_{26}H_{31}N_6O_2$ [M−H]⁻: 459.25, found 459.2.

¹H NMR (500 MHz, CDCl₃): δ 7.40 (bs, 2H), 7.09 (m, 1H), 6.79 (bs, 1H), 6.26 (m, 3H), 3.66 (s, 6H), 3.53 (s, 2H), 2.93 (m, 2H), 2.87 (m, 2H), 2.45 (m, 8H), 2.22 (s, 3H) ppm.

¹³C NMR (175 MHz, CDCl₃): δ 160.7, 146.7, 142.9, 132.0, 124.2, 106.3, 103.3, 98.0, 63.0, 55.1, 54.8, 52.4, 45.8, 35.4 ppm.

Example 8: (2-(5(3)-(3,5-Dimethoxyphenethyl)-1H-pyrazol-3(5)-yl)-1H-benzo[d]-imidazol-5(6)-yl)(4-methylpiperazin-1-yl)methanone

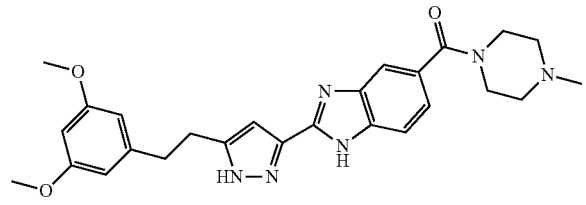

The compound was obtained by the method analogous to that described in Example 1. Starting from 5(3)-[2-(3,5-dimethoxyphenyl)ethyl]-1H-pyrazole-3(5)-carboxylic acid (Compound P5, 0.100 g, 0.362 mmol), EDCl (0.077 g, 0.402 mmol), hydroxybenzotriazole (0.054 g, 0.402 mmol), (3,4-diaminophenyl)(4-methylpiperazin-1-yl)-methanone (Compound P23, 0.094 g, 0.402 mmol) in 2 ml of DMF and using 5 ml of acetic acid, 0.090 g of the title product in the form of a creamy solid were obtained (yield 52.4%).

MS-ESI: (m/z) calculated for $C_{26}H_{29}N_6O_3$ [M−H]⁻: 473.23, found 473.2.

Example 9: 2-(5(3)-(3,5-Dimethoxyphenethyl)-1H-pyrazol-3(5)-yl)-5(6)-(((3R,5S)-3,5-dimethylpiperazin-1-yl)methyl)-1H-benzo[d]imidazole

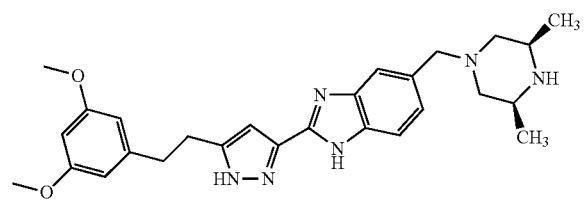

The compound was obtained by the method analogous to that described in Example 1. Starting from 5(3)-[2-(3,5-dimethoxyphenyl)ethyl]-1H-pyrazole-3(5)-carboxylic acid (Compound P5, 0.170 g, 0.615 mmol), EDCl (0.130 g, 0.677 mmol), hydroxybenzotriazole (0.091 g, 0.677 mmol), 4-{[(3R,5S)-3,5-dimethylpiperazin-1-yl]-methyl}benzene-1,2-diamine (Compound P26, 0.159 g, 0.677 mmol) in 5 ml of DMF and then 6 ml of acetic acid, 0.135 g of the title product in the form of a light-brown solid were obtained (yield 46.2%).

¹H NMR (500 MHz, DMSO-d6) δ 13.25-13.05 (bs, 1H), 7.84 (d, J=8.3 Hz, 1H), 7.54 (d, 8.3, 1H), 7.52-7.38 (m, 1H), 7.34 (dd, J=7.5 Hz, J=7.2 Hz, 1H), 7.28 (dd, J=7.6 Hz, J=7.2 Hz, 1H), 7.11 (J=8.02 Hz, 1H), 6.64 (bs, 1H), 6.47-6.37 (m,

2H), 6.33 (s, 1H), 3.71 (s, 6H), 3.62 (s, 2H), 3.23-3.17 (m, 2H), 3.02-2.82 (m, 6H), 2.07 (t, J=11.4 Hz, 2H), 1.21 (s, 3H), 1.19 (s, 3H) ppm.

Example 10: (2-(5(3)-(3,5-Dimethoxyphenethyl)-1H-pyrazol-3(5)-yl)-1H-benzo[d]-imidazol-5-yl)((3R,5S)-3,5-dimethylpiperazin-1-yl)methanone

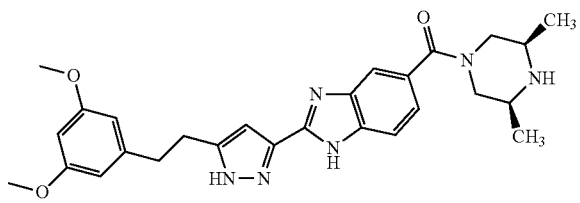

The compound was obtained by the method analogous to that described in Example 1. Starting from 5(3)-[2-(3,5-dimethoxyphenyl)ethyl]-1H-pyrazole-3(5)-carboxylic acid (Compound P5, 0.308 g, 1.12 mmol), EDCl (0.198 g, 1.03 mmol), hydroxybenzotriazole (0.140 g, 1.03 mmol), (3,4-diaminophenyl)[(3R,5S)-3,5-dimethylpiperazin-1-yl]methanone (Compound P27, 0.231 g, 0.930 mmol) in 6 ml of DMF and using 8 ml of acetic acid, 0.120 g of the title product in the form of a creamy solid were obtained (yield 26.4%).

MS-ESI: (m/z) calculated for $C_{27}H_{31}N_6O_3$ [M−H]$^-$: 487.25, found 487.2.

Example 11: 2-(5(3)-(3,5-Dimethoxyphenethyl)-1H-pyrazol-3(5)-yl)-5(6)-(piperidin-1-ylmethyl)-1H-benzo[d]imidazole

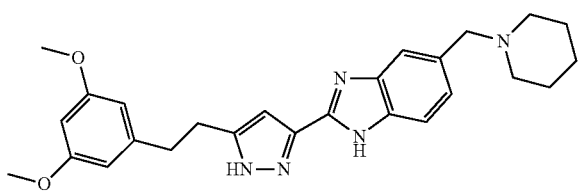 [SMILES: COc1cc(CCc2cc(-c3nc4cc(CN5CCCCC5)ccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.213 g, 0.771 mmol), EDCl (0.163 g, 0.848 mmol), hydroxybenzotriazole (0.115 g, 0.848 mmol), 4-(piperidin-1-ylmethyl)benzene-1,2-diamine (Compound P30, 0.190 g, 0.925 mmol) in 4 ml of DMF and using 5 ml of acetic acid, 0.045 g of the title product in the form of an amorphous beige powder were obtained (yield 13.1%).

MS-ESI: (m/z) calculated for $C_{26}H_{32}N_5O_2$ [M+H]$^+$: 446.26, found 446.2, dla $C_{26}H_{31}N_5O_2Na$ [M+Na]$^+$: 468.25, found 468.2, dla $C_{26}H_{30}N_5O_2$ [M−H]$^-$: 444.24, found 444.2.

$^1$H NMR (500 MHz, CDCl$_3$): δ 7.46 (m, 2H), 7.10 (m, 1H), 6.72 (m, 3H), 3.65 (s, 6H), 3.54 (s, 2H), 2.81 (m, 4H), 2.41 (m, 4H), 1.53 (m, 4H), 1.38 (m, 2H) ppm.

Example 12: 2-(5(3)-(3,5-Dimethoxyphenethyl)-1H-pyrazol-3(5)-yl)-5(6)-((4-(4-methyl-piperazin-1-yl)piperidin-1-yl)methyl)-1H-benzo[d]imidazole

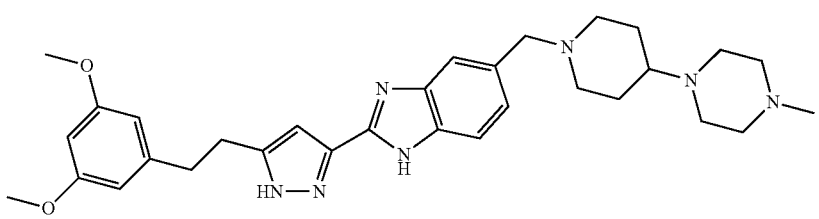

The compound was obtained by the method analogous to that described in Example 1. Starting from 5(3)-[2-(3,5-dimethoxyphenyl)ethyl]-1H-pyrazole-3(5)-carboxylic acid (Compound P5, 0.341 g, 1.24 mmol), EDCl (0.261 g, 1.36 mmol), hydroxybenzotriazole (0.184 g, 1.36 mmol), 4-((4-(4-methylpiperazin-1-yl)piperidin-1-yl)-methyl)benzene-1,2-diamine (Compound P33, 0.450 g, 1.48 mmol) in 2 ml of DMF and using 4 ml of acetic acid, 0.210 g of the title product in the form of an amorphous yellow powder were obtained (yield 31.3%).

MS-ESI: (m/z) calculated for $C_{31}H_{42}N_7O_2$ [M+H]$^+$: 544.34, found 544.2, dla $C_{31}H_{40}N_7O_2$ [M−H]$^-$: 542.32, found 542.2.

$^1$H NMR (500 MHz, CDCl$_3$): δ 7.43 (bs, 2H), 7.25 (m, 1H), 7.18-7.08 (m, 2H), 6.78 (bs, 1H), 6.24 (m, 3H), 3.66 (s, 6H), 3.48 (bs, 2H), 3.04-2.70 (m, 6H), 2.66-2.31 (m, 9H), 2.88-2.18 (m, 5H), 1.97-1.83 (m, 2H), 1.78-1.61 (m, 2H), 1.57-1.42 (m, 2H) ppm.

$^{13}$C NMR (125 MHz, CDCl$_3$): δ 160.7, 142.9, 128.9, 128.2, 125.2, 124.2, 106.4, 103.3, 98.1, 63.2, 61.7, 55.3, 55.1, 52.9, 48.8, 45.8, 44.86, 35.4, 27.9 ppm.

Example 13: 5(6)-([1,4'-Bipiperidin]-1'-ylmethyl)-2-(5(3)-(3,5-dimethoxyphenethyl)-1H-pyrazol-3(5)-yl)-1H-benzo[d]imidazole

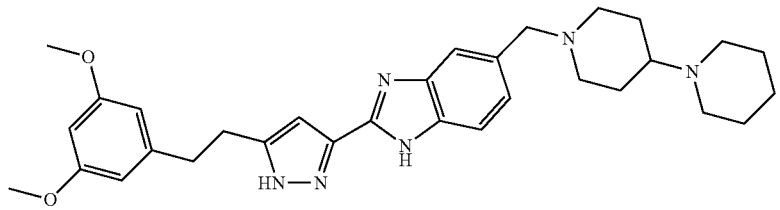 [SMILES: COc1cc(CCc2cc(-c3nc4cc(CN5CCC(N6CCCCC6)CC5)ccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.149 g, 0.541 mmol), EDCl (0.096 g, 0.500 mmol), hydroxybenzotriazole (0.068 g, 0.500 mmol), 4-(1,4'-bipiperidin-1'-ylmethyl)benzene-1,2-diamine (Compound P35, 0.130 g, 0.451 mmol) in 4 ml of DMF and using 5 ml of acetic acid, 0.069 g of the title product in the form of an orange meringue were obtained (yield 43.2%).

MS-ESI: (m/z) calculated for $C_{31}H_{39}N_6O_2$ [M−H]⁻: 527.31, found 527.2.

¹H NMR (500 MHz, CDCl₃): δ 7.40 (s, 6H), 7.08 (d, J=6.7 Hz, 3H), 6.78 (s, 3H), 6.26 (s, 10H), 3.67 (s, 24H), 3.49 (s, 6H), 2.90 (s, 23H), 2.51 (s, 15H), 2.30 (s, 4H), 1.88 (s, 7H), 1.70 (s, 8H), 1.58 (s, 24H), 1.40 (s, 8H) ppm.

Example 14: 4-(2-(4-((2-(5(3)-(3,5-Dimethoxyphenethyl)-1H-pyrazol-3(5)-yl)-1H-benzo[d]imidazol-5(6)-yl)methyl)piperazin-1-yl)ethyl)morpholine amine (Compound P39, 0.303 g, 0.950 mmol) in 10 ml of DMF and using 5 ml of acetic acid, 0.159 g of the title product in the form of a yellow solid were obtained (yield 29.9%).

MS-ESI: (m/z) calculated for $C_{31}H_{39}N_7O_3$ [M−H]⁻: 558.32, found 558.3.

¹H NMR (500 MHz, DMSO-d6) δ 12.95 (s, 1H), 12.54 (s, 1H), 8.31 (s, 1H), 7.90 (d, J=8.4 Hz, 1H), 7.61 (d, J=8.3 Hz, 1H), 7.44-7.39 (m, 1H), 7.32 (d, J=7.2 Hz, 1H), 7.09-6.93 (m, 2H), 6.61 (s, 1H), 6.52-6.28 (m, 3H), 3.79-3.65 (m, 6H), 3.58 (dd, J=11.1, 6.5 Hz, 14H), 2.94 (dd, J=15.9, 6.6 Hz, 4H), 2.77 (s, 3H), 2.68-2.60 (m, 2H), 2.58-2.53 (m, 2H), 2.46 (s, 2H) ppm.

¹³C NMR (125 MHz, DMSO-d6) δ 160.82, 143.28, 126.60, 124.38, 119.29, 110.40, 106.83, 98.29, 66.50, 55.61, 55.47, 55.03, 53.98

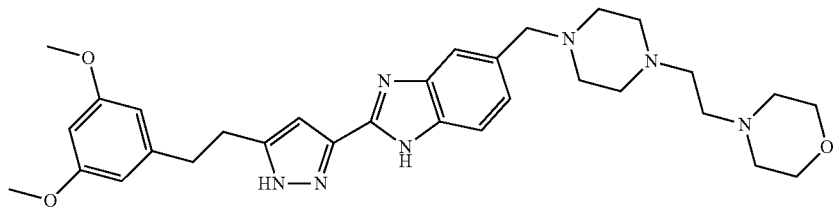 [SMILES: COc1cc(CCc2cc(-c3nc4cc(CN5CCN(CCN6CCOCC6)CC5)ccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.262 g, 0.950 mmol), EDCl (0.200 g, 1.040 mmol), hydroxybenzotriazole (0.141 g, 1.04 mmol), 4-((4-(2-morpholinoethyl)piperazin-1-yl)-methyl)benzene-1,2-di- Example 15: 2-(4-((2-(5(3)-(3,5-Dimethoxyphenethyl)-1H-pyrazol-3(5)-yl)-1H-benzo-[d]imidazol-5(6)-yl)methyl)piperazin-1-yl)-N,N-dimethylacetamide

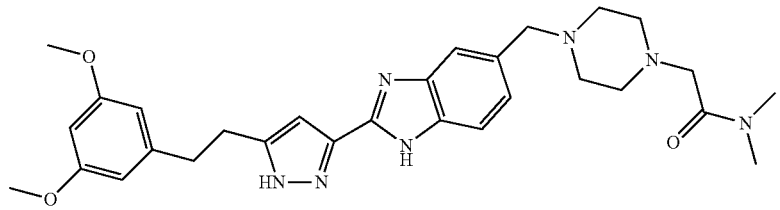

The compound was obtained by the method analogous to that described in Example 1. Starting from 5(3)-[2-(3,5- dimethoxyphenyl)ethyl]-1H-pyrazole-3(5)-carboxylic acid (Compound P5, 0.481 g, 1.74 mmol), EDCl (0.334 g, 1.74 mmol), hydroxybenzotriazole (0.196 g, 1.45 mmol), 2-(4-(3,4-diaminobenzyl)piperazin-1-yl)-N,N-dimethylacetamide (Compound P41, 0.423 g, 1.45 mmol) in 6 ml of DMF and then 5 ml of acetic acid, 0.038 g of the title product in the form of a creamy powder were obtained (yield 4.9%).

MS-ESI: (m/z) calculated for $C_{29}H_{37}N_7O_3$ [M−H]⁻: 530.28, found 530.2.

$^1$H NMR (500 MHz, CDCl$_3$) δ 6.93-6.83 (m, 1H), 6.52-6.40 (m, 2H), 6.36-6.28 (m, 1H), 3.72 (s, 6H), 3.64-3.50 (m, 2H), 3.33-3.17 (m, 2H), 3.17-3.02 (m, 3H), 3.02-2.72 (m, 7H), 2.71-2.12 (m, 8H) ppm.

Example 16: 4-(2-(5(3)-(3,5-Dimethoxyphenethyl)-1H-pyrazol-3(5)-yl)-1H-benzo[d]-imidazol-5(6)-yl)morpholine

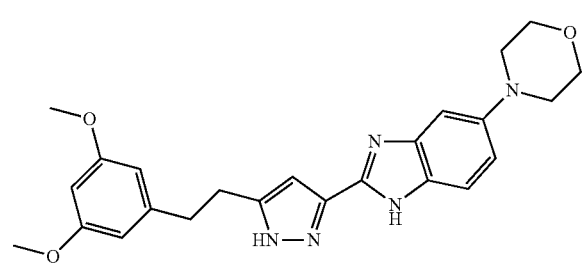 [SMILES: COc1cc(CCc2cc(-c3nc4cc(N5CCOCC5)ccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.150 g, 0.543 mmol), EDCl (0.115 g, 0.600 mmol), hydroxybenzotriazole (0.081 g, 0.600 mmol), 4-(morpholin-4-yl)benzene-1,2-diamine (Compound P43, 0.116 g, 0.600 mmol) in 10 ml of DMF and using 5 ml of acetic acid, 0,050 g of the title product in the form of an orange meringue were obtained (yield 21.2%).

MS-ESI: (m/z) calculated for $C_{24}H_{28}N_5O_3$ [M+H]⁺: 434.22, found 434.2.

$^1$H NMR (500 MHz, CDCl$_3$) δ 7.46 (s, 1H), 7.01-6.87 (m, 2H), 6.75 (s, 1H), 6.23 (s, 3H), 3.78 (m, 4H), 3.66 (s, 6H), 3.02 (s, 4H), 2.77 (s, 4H) ppm.

$^{13}$C NMR (126 MHz, CDCl$_3$) δ 161.74, 160.79, 148.95, 142.77, 114.84, 106.37, 103.52, 97.97, 66.88, 55.17, 50.58, 35.24, 27.45 ppm.

Example 17: 2-(5(3)-(3,5-Dimethoxyphenethyl)-1H-pyrazol-3(5)-yl)-5(6)-(4-methyl-piperazin-1-yl)-1H-benzo[d]imidazole

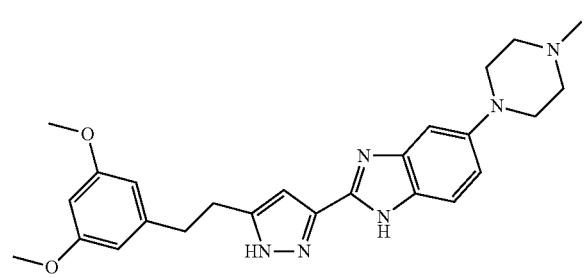

The compound was obtained by the method analogous to that described in Example 1. Starting from 5(3)-[2-(3,5-dimethoxyphenyl)ethyl]-1H-pyrazole-3(5)-carboxylic acid (Compound P5, 0.150 g, 0.543 mmol), EDCl (0.116 g, 0.603 mmol), hydroxybenzotriazole (0.081 g, 0.603 mmol), 4-(4-methylpiperazin-1-yl)benzene-1,2-diamine (Compound P45, 0.124 g, 0.603 mmol) in 2 ml of DMF and using 5 ml of acetic acid, 0.100 g of the title product were obtained (yield 41.2%).

MS-ESI: (m/z) calculated for $C_{25}H_{31}N_6O_2$ [M+H]⁺: 447.25, found 447.3.

Example 18: 2-(5(3)-(3,5-Dimethoxyphenethyl)-1H-pyrazol-3(5)-yl)-5(6)-(4-ethylpiperazin-1-yl)-1H-benzo[d]imidazole

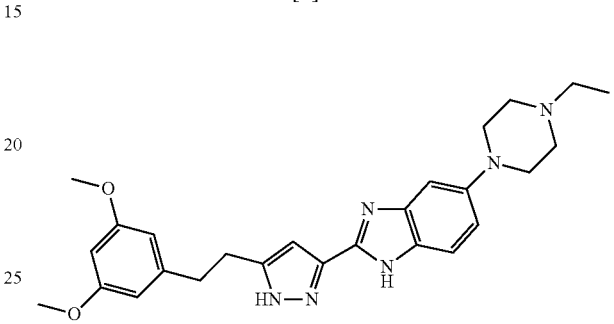

The compound was obtained by the method analogous to that described in Example 1. Starting from 5(3)-[2-(3,5-dimethoxyphenyl)ethyl]-1H-pyrazole-3(5)-carboxylic acid (Compound P5, 0.100 g, 0.362 mmol), EDCl (0.077 g, 0.402 mmol), hydroxybenzotriazole (0.054 g, 0.402 mmol), 4-[(4-ethylpiperazin-1-yl)methyl]benzene-1,2-diamine (Compound P47, 0.089 g, 0.402 mmol) in 1 ml of DMF and using 5 ml of acetic acid, 0.108 g of the title product were obtained (yield 64.8%).

MS-ESI: (m/z) calculated for $C_{26}H_{33}N_6O_2$ [M+H]⁺: 461.26, found 461.2.

Example 19: 2-(5(3)-(3,5-Dimethoxyphenethyl)-1H-pyrazol-3(5)-yl)-5(6)-((3R,5S)-3,5-dimethylpiperazin-1-yl)-1H-benzo[d]imidazole

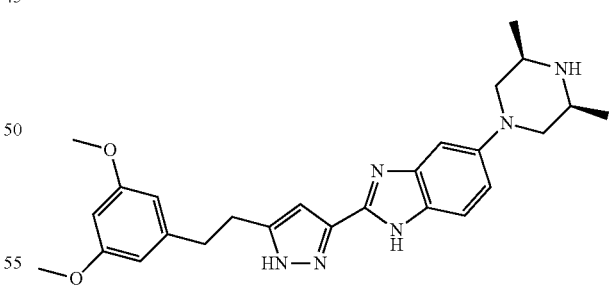

The compound was obtained by the method analogous to that described in Example 1. Starting from 5(3)-[2-(3,5-dimethoxyphenyl)ethyl]-1H-pyrazole-3(5)-carboxylic acid (Compound P5, 0.218 g, 0.789 mmol), EDCl (0.168 g, 0.876 mmol), hydroxybenzotriazole (0.118 g, 0.876 mmol), 4-[(3R,5S)-3,5-dimethylpiperazin-1-yl]-benzene-1,2-diamine (Compound P49, 0.193 g, 0.876 mmol) in 2 ml of DMF and using 5 ml of acetic acid, 0.145 g of the title product in the form of a white powder were obtained (yield 39.9%).

MS-ESI: (m/z) calculated for $C_{26}H_{31}N_6O_2$ [M+H]$^+$: 459.25, found 459.2.

Example 20: 2-(4-(2-(5(3)-(3,5-Dimethoxyphenethyl)-1H-pyrazol-3(5)-yl)-1H-benzo-[d]imidazol-5(6)-yl)piperazin-1-yl)-N,N-diethylethaneamine

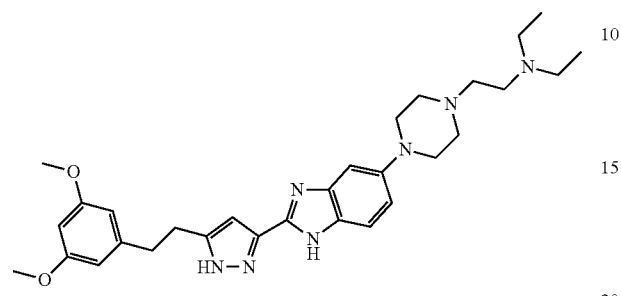

The compound was obtained by the method analogous to that described in Example 1. Starting from 5(3)-[2-(3,5-dimethoxyphenyl)ethyl]-1H-pyrazole-3(5)-carboxylic acid (Compound P5, 0.171 g, 0.618 mmol), EDCl (0.130 g, 0.679 mmol), hydroxybenzotriazole (0.092 g, 0.679 mmol), 4-{4-[2-(diethylamino)ethyl]piperazin-1-yl}-benzene-1,2-diamine (Compound P51, 0.180 g, 0.618 mmol) in 10 ml of DMF and using 5 ml of acetic acid, 0.150 g of the title product in the form of an orange oil were obtained (yield 45.6%).

MS-ESI: (m/z) calculated for $C_{30}H_{41}N_7O_2$ [M+H]$^+$: 532.34, found 532.3.

Example 21: 2-(4-(2-(5(3)-(3,5-Dimethoxyphenethyl)-1H-pyrazol-3(5)-yl)-1H-benzo-[d]imidazo-5(6)-yl)piperazin-1-yl)-1-morpholinoethanone

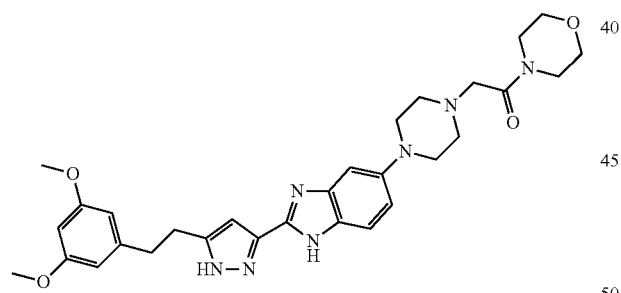

The compound was obtained by the method analogous to that described in Example 1. Starting from 5(3)-[2-(3,5-dimethoxyphenyl)ethyl]-H-pyrazole-3(5)-carboxylic acid (Compound P5, 0.157 g, 0.570 mmol), EDCl (0.120 g, 0.627 mmol), hydroxybenzotriazole (0.084 g, 0.627 mmol), 4-{4-[2-(morpholin-4-yl)ethyl]piperazin-1-yl}-benzene-1,2-diamine (Compound P53, 0.182 g, 0.579 mmol) in 10 ml of DMF and using 5 ml of acetic acid, 0.070 g of the title product in the form of a yellow solid were obtained (yield 21.9%).

MS-ESI: (m/z) calculated for $C_{30}H_{38}N_7O_4$ [M+H]$^+$: 560.29, found 560.3.

$^1$H NMR (500 MHz, CDCl$_3$) δ 7.44 (t, J=12.4 Hz, 1H), 6.98-6.83 (m, 2H), 6.78 (s, 1H), 6.28 (t, J=13.0 Hz, 4H), 3.72-3.57 (m, 16H), 3.21 (s, 2H), 3.17-3.03 (m, 4H), 2.86 (m, 2H), 2.63 (s, 4H) ppm.

$^{13}$C NMR (125 MHz, CDCl$_3$) δ 168.15, 160.82, 148.4, 143.01, 106.43, 98.09, 77.25, 77.00, 76.74, 66.89, 60.9, 55.23, 55.19, 53.25, 50.49, 46.09, 42.23, 35.46 ppm.

Example 22: 4-(2-(5(3)-(3,5-Dimethoxyphenethyl)-1H-pyrazol-3(5)-yl)-1H-benzo[d]-imidazol-4(7)-yl) morpholine

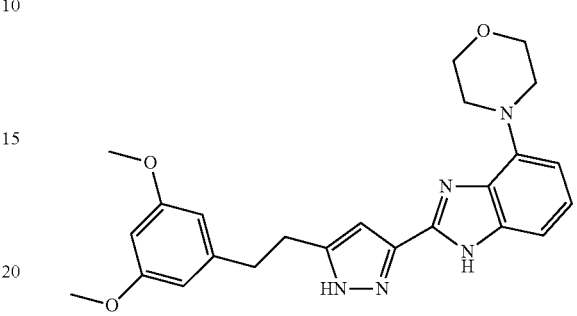

The compound was obtained by the method analogous to that described in Example 1. Starting from 5(3)-[2-(3,5-dimethoxyphenyl)ethyl]-1H-pyrazole-3(5)-carboxylic acid (Compound P5, 0.100 g, 0.362 mmol), EDCl (0.077 g, 0.402 mmol), hydroxybenzotriazole (0.054 g, 0.402 mmol), 3-(morpholin-4-yl)benzene-1,2-diamine (Compound P55, 0.078 g, 0.402 mmol) in 2 ml of DMF and using 5 ml of acetic acid 0.148 g of the title product in the form of a yellow solid were obtained (yield 94.3%).

MS-ESI: (m/z) calculated for $C_{24}H_{27}N_5O_3$ [M–H]$^-$: 432.20, found 432.1.

Example 23: 2-(5(3)-(3,5-Dimethoxyphenethyl)-1H-pyrazol-3(5)-yl)-4(7)-((3R,5S)-3,5-dimethylpiperazin-1-yl)-1H-benz[d]imidazole

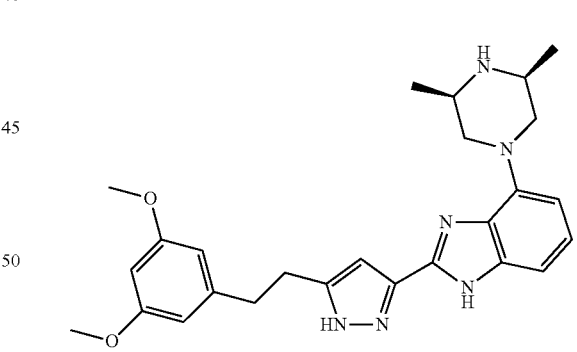

The compound was obtained by the method analogous to that described in Example 1. Starting from 5(3)-[2-(3,5-dimethoxyphenyl)ethyl]-1H-pyrazole-3(5)-carboxylic acid (Compound P5, 0.100 g, 0.362 mmol), EDCl (0.077 g, 0.402 mmol), hydroxybenzotriazole (0.054 g, 0.402 mmol), 3-[(3R,5S)-3,5-dimethylpiperazin-1-yl]-benzene-1,2-diamine (Compound P57, 0.078 g, 0.402 mmol) in 2 ml of DMF and using 5 ml of acetic acid, 0.148 g of the title product in the form of a yellow solid were obtained (yield 94.3%).

MS-ESI: (m/z) calculated for $C_{24}H_{27}N_5O_3$ [M–H]$^-$: 432.20, found 432.1.

¹H NMR (500 MHz, DMSO-d6) δ 7.87 (d, J=8.4 Hz, 0.5H), 7.61 (d, J=8.3 Hz, 0.5H), 7.39 (dd, J=11.3, 3.9 Hz, 0.5H), 7.33-7.27 (m, 0.5H), 7.08-7.02 (m, 1H), 6.64 (s, 1H), 6.58 (s, 1H), 6.44 (d, J=2.3 Hz, 2H), 6.33 (t, J=2.2 Hz, 1H), 4.54 (d, J=10.7 Hz, 4H), 3.71 (s, 6H), 3.48 (br, 2H), 3.01-2.90 (m, J=13.8, 6.5 Hz, 4H), 2.83 (dd, J=11.2 Hz, 2H), 1.34 (d, J=6.5 Hz, 6H) ppm.

¹³C NMR (126 MHz, DMSO-d6) δ 160.82, 143.72, 143.31, 141.12, 136.11, 135.24, 128.13, 126.20, 124.21, 123.39, 119.21, 110.59, 107.06, 106.84, 104.80, 102.97, 98.29, 55.48, 52.38, 51.18, 49.04, 35.27, 26.86, 21.53, 16.32.

Example 24: 2-(5(3)-(3,5-Dimethoxyphenethyl)-1H-pyrazol-3(5)-yl)-4(7)-(4-isopropylpiperazin-1-yl)-1H-benzo[d]imidazole

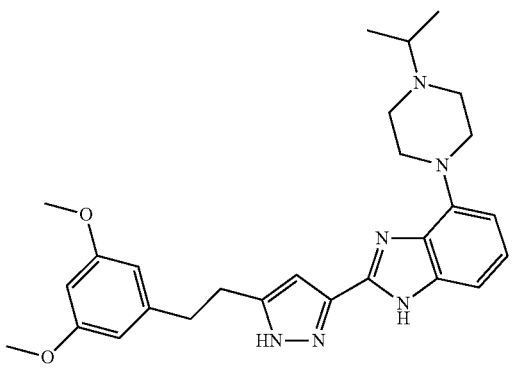 [SMILES: COc1cc(CCc2cc(-c3nc4c(N5CCN(C(C)C)CC5)cccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.178 g, 0.644 mmol), EDCl (0.136 g, 0.708 mmol), hydroxybenzotriazole (0.096 g, 0.708 mmol), 3-[4-(propan-2-yl)piperidin-1-yl]benzene-1,2-diamine (Compound P59, 0.166 g, 0.708 mmol) in 2 ml of DMF and using 5 ml of acetic acid, 0.124 g of the title product in the form of a yellow solid were obtained (yield 40.6%).

MS-ESI: (m/z) calculated for $C_{27}H_{33}N_6O_2$ [M–H]⁻: 473.27, found 473.3.

¹H NMR (500 MHz, CDCl₃) δ 7.77 (d, J=6.5 Hz, 0.5H), 7.63 (d, J=5.7 Hz, 0.5H), 7.24-7.21 (m, 1H), 7.00 (br, 2H), 6.81-6.78 (br, 2H), 6.54 (br, 2H), 6.24 (br, 1H), 3.67 (s, 6H), 3.53 (s, 4H), 2.82 (s, 1H), 1.12 (s, 1H) ppm.

Example 25: 4(7)-([1,4'-bipiperidin]-1'-yl)-2-(5(3)-(3,5-dimethoxyphenethyl)-1H-pyrazol-3(5)-yl)-1H-benzo[d]imidazole

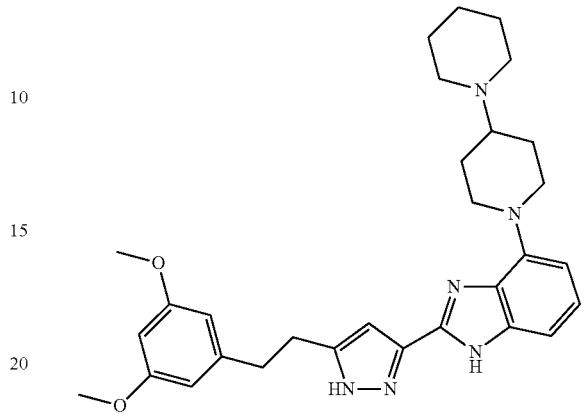

The compound was obtained by the method analogous to that described in Example 1. Starting from 5(3)-[2-(3,5-dimethoxyphenyl)ethyl]-1H-pyrazole-3(5)-carboxylic acid (Compound P5, 0.080 g, 0.289 mmol), EDCl (0.061 g, 0.321 mmol), hydroxybenzotriazole (0.043 g, 0.321 mmol), 3-(1,4'-bipiperidin-1'-yl)benzene-1,2-diamine (Compound P61, 0.088 g, 0.321 mmol) in 2 ml of DMF and using 5 ml of acetic acid, 0.062 g of the title product in the form of a yellow solid were obtained (yield 41.8%).

MS-ESI: (m/z) calculated for $C_{30}H_{38}N_6O_2$ [M–H]⁻: 513.29, found 513.3.

¹H NMR (500 MHz, CDCl₃) δ 7.21 (dd, J=12.2, 8.2 Hz, 1H), 7.06 (d, J=11.6 Hz, 2H), 6.84 (s, 1H), 6.64 (d, J=14.9 Hz, 1H), 6.24 (s, 4H), 3.70 (d, J=26.5 Hz, 9H), 2.90 (t, J=45.3 Hz, 7H), 2.60 (s, 9H), 1.85 (s, 2H), 1.74 (s, 1H), 1.72-1.50 (m, 8H), 1.41 (s, 3H) ppm.

Example 26: 4-(2-(4-(2-(5(3)-(3,5-Dimethoxyphenethyl)-1H-pyrazol-3(5)-yl)-1H-benzo[d]imidazol-4(7)-yl)piperazin-1-yl)ethyl)morpholine

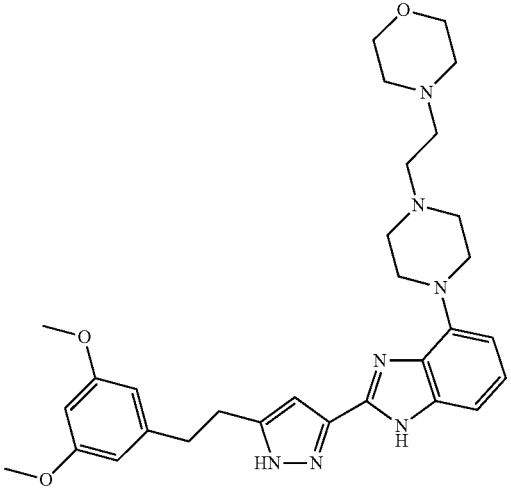 [SMILES: COc1cc(CCc2cc(-c3nc4c(N5CCN(CCN6CCOCC6)CC5)cccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.100 g, 0.362 mmol), EDCl (0.077 g, 0.402 mmol), hydroxybenzotriazole (0.054 g, 0.402 mmol), 3-{4-[2-(morpholin-4-yl)ethyl]piperazin-1-yl}-benzene-1,2-diamine (Compound P63, 0.123 g, 0.402 mmol) in 2 ml of DMF and using 5 ml of acetic acid, 0.054 g of the title product in the form of a yellow solid were obtained (yield 27.3%).

MS-ESI: (m/z) calculated for $C_{30}H_{39}N_7O_3$ [M−H]⁻: 544.30, found 544.3.

¹H NMR (500 MHz, DMSO-d6) δ 12.95 (s, 1H), 12.54 (s, 1H), 8.31 (s, 1H), 7.90 (d, J=8.4 Hz, 1H), 7.61 (d, J=8.3 Hz, 1H), 7.44-7.39 (m, 1H), 7.32 (d, J=7.2 Hz, 1H), 7.09-6.93 (m, 2H), 6.61 (s, 1H), 6.52-6.28 (m, 3H), 3.79-3.65 (m, 6H), 3.58 (dd, J=11.1, 6.5 Hz, 14H), 2.94 (dd, J=15.9, 6.6 Hz, 4H), 2.77 (s, 3H), 2.68-2.60 (m, 2H), 2.58-2.53 (m, 2H), 2.46 (s, 2H) ppm.

¹³C NMR (125 MHz, DMSO-d6) δ 160.82, 143.28, 126.60, 124.38, 119.29, 110.40, 106.83, 98.29, 66.50, 55.61, 55.47, 55.03, 53.98, 53.43 ppm.

Example 27: 4-(2-(3-(2-(5(3)-(3,5-Dimethoxyphenethyl)-1H-pyrazol-3(5)-yl)-1H-benzo[d]imidazo-5(6)-yl)-1H-pyrazol-1-yl)ethyl)morpholine

Example 28: 4-((5(3)-(2-(5(3)-(3,5-Dimethoxyphenethyl)-1H-pyrazol-3(5)-yl)-1H-benzo[d]imidazol-5(6)-yl)thiophen-2-yl)methyl)morpholine

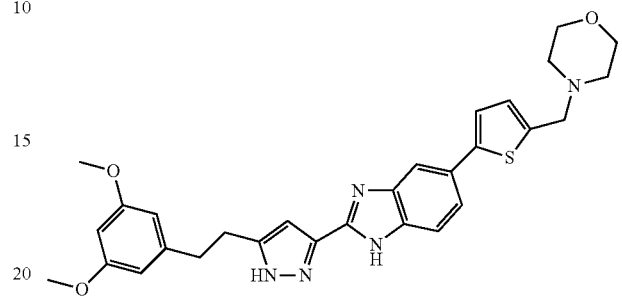

The compound was obtained by the method analogous to that described in Example 1. Starting from 5(3)-[2-(3,5-dimethoxyphenyl)ethyl]-1H-pyrazole-3(5)-carboxylic acid (Compound P5, 0.163 g, 0.591 mmol), EDCl (0.126 g, 0.657 mmol), hydroxybenzotriazole (0.089 g, 0.657 mmol), 4-[5-(morpholin-4-ylmethyl)thiophen-2-yl]-benzene-1,2-diamine (Compound P67, 0.190 g, 0.657 mmol) in 7 ml of DMF and using 5 ml of acetic acid, 0.016 g of the title product in the form of a creamy solid were obtained (yield 5.1%)

MS-ESI: (m/z) calculated for $C_{29}H_{30}N_5O_3S$ [M−H]⁻: 528.20, found 528.2.

¹H NMR (500 MHz, DMSO) δ 13.06 (bs, 1H), 12.71 (bs, 1H), 7.80 (bs, 1H), 7.59 (bs, 1H), 7.44 (d, J=6.4 Hz, 1H), 7.28 (d, J=3.5 Hz, 1H), 6.95 (d, J=4.0, 2.1 Hz, 1H), 6.65 (bs, 1H), 6.43 (d, J=2.2 Hz, 2H), 6.36-6.30 (m, 1H), 3.71 (s, 6H), 3.69-3.66 (m, 2H), 3.62-3.57 (m, 4H), 3.01-2.90 (m, 4H), 2.46-2.41 (m, 4H) ppm.

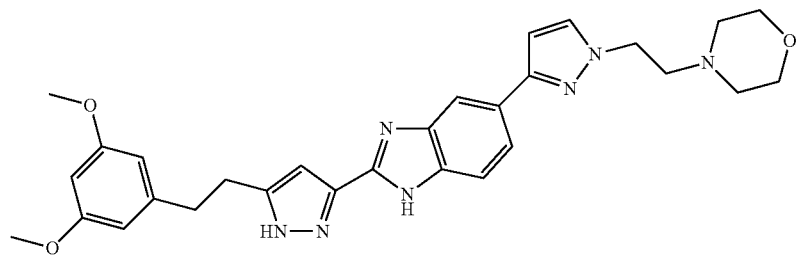 [SMILES: COc1cc(CCc2cc(-c3nc4cc(-c5ccn(CCN6CCOCC6)n5)ccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.147 g, 0.531 mmol), EDCl (0.113 g, 0.589 mmol), hydroxybenzotriazole (0.080 g, 0.589 mmol), 4-[5-(morpholin-4-ylmethyl)thiophen-2-yl]-benzene-1,2-diamine (Compound P65, 0.168 g, 0.584 mmol) in 6 ml of DMF and using 5 ml of acetic acid, 0.072 g of the title product in the form of a creamy solid were obtained (yield 29.5%)

MS-ESI: (m/z) calculated for $C_{29}H_{32}N_7O_3$ [M−H]⁻: 526.25, found 526.2.

¹H NMR (500 MHz, DMSO-d6) δ 13.00 (bs, 1H), 12.59 (d, J=8.5 Hz, 1H), 8.15 (d, J=8.2 Hz, 1H), 7.84 (d, J=13.2 Hz, 1H), 7.76, 7.53 (2×s, 1H), 7.55 (d, J=8.0 Hz, 1H), 7.36 (d, J=8.8 Hz, 1H), 6.64-6.60 (m, 1H), 6.43 (m, 2H), 6.35-6.31 (m, 1H), 4.29-4.19 (m, 2H), 3.71 (s, 6H), 3.61-3.53 (m, 4H), 3.03-2.89 (m, 4H), 2.78-2.71 (m, 2H), 2.46-2.39 (m, 4H) ppm.

Example 29: 4-(3-(2-(5(3)-(3,5-Dimethoxyphenethyl)-1H-pyrazol-3(5)-yl)-1H-benzo-[d]imidazol-5(6)-yl)benzyl)morpholine

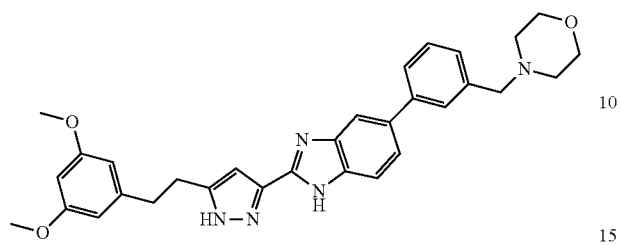

The compound was obtained by the method analogous to that described in Example 1. Starting from 5(3)-[2-(3,5-dimethoxyphenyl)ethyl]-1H-pyrazole-3(5)-carboxylic acid (Compound P5, 0.147 g, 0.531 mmol), EDCl (0.113 g, 0.589 mmol), hydroxybenzotriazole (0.080 g, 0.589 mmol), 3'-(morpholin-4-ylmethyl)biphenyl-3,4-diamine (Compound P69, 0.167 g, 0.589 mmol) in 6 ml of DMF and using 5 ml of acetic acid, 0.059 g of the title product in the form of a creamy solid were obtained (yield 21.4%)

MS-ESI: (m/z) calculated for $C_{31}H_{32}N_5O_3$ [M–H]$^-$: 522.25, found 522.2.

$^1$H NMR (500 MHz, DMSO-d6) δ 13.05 (bs, 1H), 12.71 (bs, 1H), 7.96, 7.69 (2×d, J=7.7 Hz, 1H), 7.61 (bs, 1H), 7.59-7.55 (m, 1H), 7.54-7.49 (m, 1H), 7.48-7.38 (m, 2H), 7.28 (d, J=7.3 Hz, 1H), 6.66 (s, 1H), 6.43 (d, 2H), 6.35-6.31 (m, 1H), 3.71 (s, 6H), 3.62-3.58 (m, 4H), 3.58 (s, 2H), 3.02-2.97 (m, 2H), 2.96-2.91 (m, 2H), 2.46-2.39 (m, 4H) ppm.

Example 30: (4-(2-(5(3)3-(3,5-Dimethoxyphenethyl)-1H-pyrazol-3(5)-yl)-1H-benzo-[d]imidazol-5(6)-yl)phenyl)(morpholino)methanone

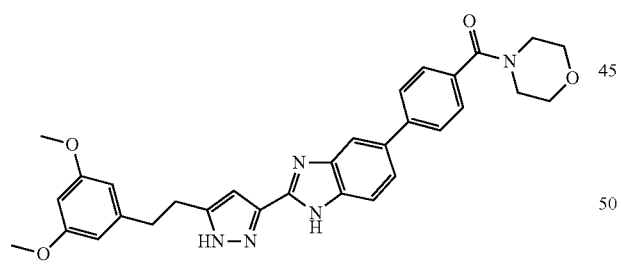

The compound was obtained by the method analogous to that described in Example 1. Starting from 5(3)-[2-(3,5-dimethoxyphenyl)ethyl]-1H-pyrazole-3(5)-carboxylic acid (Compound P5, 0.217 g, 0.871 mmol), EDCl (0.167 g, 0.871 mmol), hydroxybenzotriazole (0.118 g, 0.871 mmol), (3',4-diaminobiphenyl-4-yl)(morpholin-4-yl)-methanone (Compound P71, 0.260 g, 0.871 mmol) in 9 ml of DMF and using 5 ml of acetic acid, 0.069 g of the title product were obtained (yield 16.4%).

MS-ESI: (m/z) calculated for $C_{31}H_{30}N_5O_4$ [M–H]$^-$: 536.23, found 536.2.

$^1$H NMR (500 MHz, DMSO-d6) δ 13.06 (bs, 1H), 12.77 (d, J=20.1 Hz, 1H), 7.92-7.72 (m, 3H), 7.71-7.65 (m, 1H), 7.51 (m, 3H), 6.67 (s, 1H), 6.44 (s, 2H), 6.35-6.31 (m, 1H), 3.71 (s, 6H), 3.68-3.48 (m, 8H), 3.02-2.97 (m, 2H), 2.96-2.90 (m, 2H) ppm.

Example 31: (4-(2-(5(3)-(3,5-Dimethoxyphenethyl)-1H-pyrazol-3(5)-yl)-1H-benzo[d]-imidazol-5(6)-yl)phenyl)(morpholino)methanone

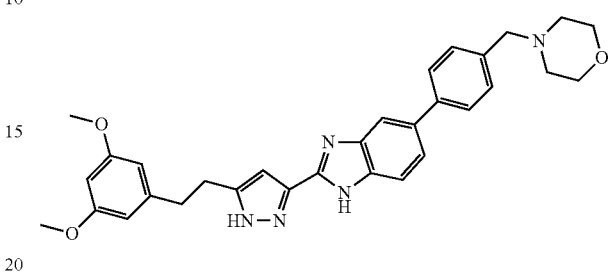

The compound was obtained by the method analogous to that described in Example 1. Starting from 5(3)-[2-(3,5-dimethoxyphenyl)ethyl]-1H-pyrazole-3(5)-carboxylic acid (Compound P5, 0.185 g, 0.671 mmol), EDCl (0.143 g, 0.745 mmol), hydroxybenzotriazole (0.101 g, 0.745 mmol), 4'-(morpholin-4-ylmethyl)biphenyl-3,4-diamine (Compound P73, 0.211 g, 0.745 mmol) in 8 ml of DMF and using 5 ml of acetic acid, 0.154 g of the title product in the form of a white powder were obtained (yield 43.7%).

MS-ESI: (m/z) calculated for $C_{31}H_{32}N_5O_4$ [M–H]$^-$: 536.23, found 536.2.

$^1$H NMR (500 MHz, DMSO-d6) δ 13.04 (bs, 1H), 12.72 (bs, 1H), 7.83 (bs, 1H), 7.64 (d, J=7.4 Hz, 2H), 7.61 (d, 1H), 7.49-7.43 (m, 1H), 7.39 (d, J=8.0 Hz, 2H), 6.66 (s, 1H), 6.43 (d, J=2.2 Hz, 2H), 6.35-6.30 (m, 1H), 3.71 (s, 6H), 3.61-3.56 (m, 4H), 3.50 (s, 2H), 3.02-2.88 (m, 4H), 2.42-2.33 (m, 4H) ppm.

Example 32: 4-(4-(2-(3-(3,5-Dimethoxyphenethyl)-1H-pyrazol-3(5)-yl)-1H-benzo[d]-imidazol-5(6)-yl)phenyl)morpholine

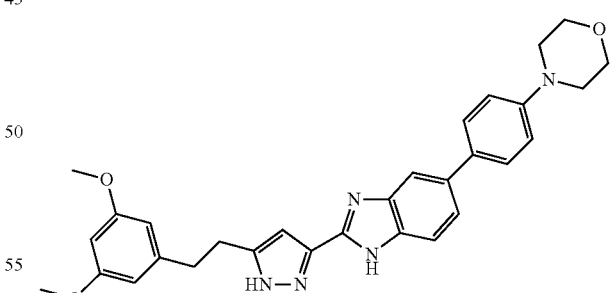

The compound was obtained by the method analogous to that described in Example 1. Starting from 5(3)-[2-(3,5-dimethoxyphenyl)ethyl]-1H-pyrazole-3(5)-carboxylic acid (Compound P5, 0.193 g, 0.776 mmol), EDCl (0.149 g, 0.776 mmol), hydroxybenzotriazole (0.105 g, 0.776 mmol), 4-(morpholin-4-ylmethyl)biphenyl-3,4-diamine (Compound P75, 0.209 g, 0.776 mmol) in 8 ml of DMF and using 5 ml of acetic acid, 0.069 g of the title product were obtained (yield 17.1%).

MS-ESI: (m/z) calculated for $C_{30}H_{30}N_5O_3$ [M–H]$^-$: 508.2, found 508.2.

$^1$H NMR (500 MHz, DMSO-d6) δ 13.03 (s, 1H), 12.65 (bs, 1H), 7.56 (d, J=8.2 Hz, 3H), 7.45-7.37 (m, J=10.6 Hz, 1H), 7.03 (d, J=8.8 Hz, 2H), 6.65 (s, 1H), 6.44 (d, J=2.2 Hz, 2H), 6.36-6.30 (m, J=2.1 Hz, 1H), 3.80-3.75 (m, 4H), 3.72 (s, 6H), 3.18-3.12 (m, J=9.6 Hz, 4H), 3.03-2.97 (m, 2H), 2.96-2.91 (m, 2H).

Example 33: 4-(5(3)-(2-(3-(3,5-Dimethoxyphenethyl)-1H-pyrazol-3(5)-yl)-1H-benzo-[d]imidazol-5 (6)-yl)pyridin-2-yl)morpholine

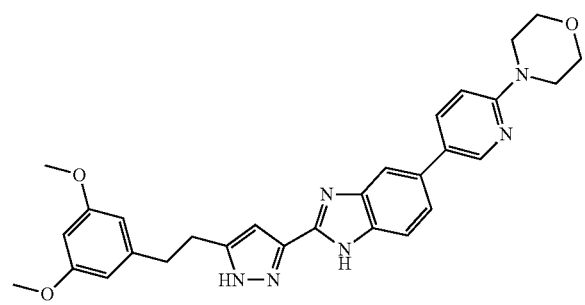 [SMILES: COc1cc(CCc2cc(-c3nc4cc(-c5ccc(N6CCOCC6)nc5)ccc4[nH]3)n[nH]2)cc(OC)c1]

The compound was obtained by the method analogous to that described in Example 1. Starting from 5(3)-[2-(3,5-dimethoxyphenyl)ethyl]-1H-pyrazole-3(5)-carboxylic acid (Compound P5, 0.097 g, 0.350 mmol), EDCl (0.074 g, 0.388 mmol), hydroxybenzotriazole (0.052 g, 0.388 mmol), 4-[6-(morpholin-4-yl)pyridin-3-yl]benzene-1,2-diamine (Compound P77, 0.104 g, 0.385 mmol) in 10 ml of DMF and using 4 ml of acetic acid, 0.146 g of the title product were obtained (yield 81.8%).

MS-ESI: (m/z) calculated for $C_{29}H_{29}N_6O_3$ [M–H]$^-$: 509.23, found 509.2.

$^1$H NMR (500 MHz, DMSO-d6) δ 13.03 (ds, 1H), 12.71-12.64 (m, 1H), 8.51-8.43 (m, 1H), 7.92-7.84 (m, 1H), 7.92-7.79 (m, 2H), 7.66-7.37 (m, 3H), 6.93 (d, J=8.8 Hz, 1H), 6.64 (ds, 1H), 6.43 (d, J=2.2 Hz, 2H), 6.34-6.32 (m, 1H), 3.74-3.70 (m, J=2.6 Hz, 4H), 3.71 (s, 6H), 3.51-3.46 (m, 4H), 3.01-2.96 (m, 2H), 2.95-2.90 (m, 2H).

Biological Activity of the Compounds of the Invention
Inhibition of FGFR1, FGFR2, FGFR3 and KDR Kinases In Vitro The effect of the compounds of the invention was analyzed using the inhibition of FGFR1, FGFR2, FGFR3 and KDR kinases assay described below.

The compounds were dissolved in 100% DMSO, and obtained solutions were serially diluted in reaction buffer (50 mM Tris pH 7.5, 10 mM MgCl2, 0.25 mM EGTA, 0.1 mM Na3VO4, 0.01% Triton X-100, 2.5 mM DTT). Recombinant FGFR1, FGFR2, FGFR3 or KDR kinase (Carna Biosciences) was diluted to final concentration of 0.1 ng/μL in the dilution buffer (50 mM Tris-HCl pH 7.5, 150 mM NaCl, 10% glycerol, 0.05% Triton X-100, 1 mM DTT). 5 μL of prepared solutions of the compounds along with 5 μL of selected kinase solution were added to each well of a 96-well plate. The plate was incubated for 10 minutes at 25° C. in plate shaker thermostat with orbital shaking at 400 rpm. To negative control wells all reagents were added except compounds and kinase, while to positive control wells—all reagents except tested compounds. The reaction was initiated by adding 15 μL of solution consisting of 5× concentrated reaction buffer (50 mM Tris pH 7.5, 10 mM MgCl2, 0.25 mM EGTA, 0.1 mM Na3VO4, 0.01% Triton X-100, 2.5 mM DTT), water, 50 μM ATP, 16.67 μM IGF-1Rtide peptide (Milipore). Than the plate was incubated for 1 hour at 25° C. in plate shaker thermostat with orbital shaking at 400 rpm. Detection of ADP obtained in enzymatic reaction was performed with ADP-Glo Kinase Assay (Promega). 25 μL of ADP-Glo Reagent was added to each well of 96-well plate and the plate was incubated for 40 minutes at 25° C. in plate shaker thermostat with orbital shaking at 400 rpm. Then 50 μL of Kinase Detection Reagent was added to each well of 96-well plate and the plate was incubated for 30 minutes at 25° C. in plate shaker thermostat with orbital shaking at 400 rpm. Finally, the intensity of luminescence was measured using Victor Light luminometer (Perkin Elmer, Inc.). The IC50 value was determined based on the intensity of luminescence in wells containing different concentrations of compounds and control wells. IC50 values were computed by fitting each point to the curve in non-linear regression model in Graph Pad software (ver. 5.03). Each compound was analyzed at least 6 times (in 6 wells) on 2 96-well plates with at least 3 wells of control.

The mean results of FGFR1, FGFR2, FGFR3 and KDR inhibition of selected compounds of the invention is presented in the following Table 1.

TABLE 1

| Example | FGFR1 IC$_{50}$ [nM] | FGFR2 IC$_{50}$ [nM] | FGFR3 IC$_{50}$ [nM] | KDR IC$_{50}$ [nM] |
| --- | --- | --- | --- | --- |
| Example 18 | 4.72 | 2.05 | 8.65 | 81.57 |
| Example 2 | 7.80 | 2.19 | 25.30 | 114.40 |
| Example 8 | 9.65 | 2.13 | 22.25 | 79.28 |
| Example 14 | 16.00 | 1.63 | 33.09 | 124.90 |
| Example 21 | 3.52 | 0.95 | 10.47 | 44.00 |
| Example 27 | 6.54 | 1.26 | 17.75 | 88.14 |
| Example 4 | 11.32 | 2.18 | 29.78 | 82.94 |
| Example 3 | 11.30 | 1.07 | 40.50 | 70.37 |

The results showed that the representative compounds of the invention were highly selective for FGFR kinases inhibition, especially FGFR1, in comparison to Vascular Endothelial Growth Factor Receptor VEGFR (KDR) inhibition.

Analysis of the Influence of the Compounds on the Cell Proliferation In Vitro

The biological activity of the compounds of the invention was analyzed on appropriate in vitro models. The cell lines were chosen to optimally reflect the neoplastic disorder on which the compounds could be effective as the medicament. The cell lines FGFR-dependent were chosen for ex. SNU-16 gastric cancer cell line with FGFR2 amplification, UM-UC-14 renal pelvis cell line with FGFR3 mutation [S249], AN3CA endometrial cancer cell line with FGFR2 mutation N549K and Ba/F3 TEL-FGFR1 murine pro-B cells expressing human FGFR1. Analysis of the influence of compounds on cell proliferation was determined using ATPlite test (Promega). This test is based on the quantitative ATP detection in cells, which demonstrates the cell metabolism and viability.

The cells were seeded on the 96-well plate in culture medium without the inhibitor. After 24 hours, the cells were treated with increasing concentration of a compound. Subsequently, the ATPlite test was performed according to the manufacturer's protocol after 72 hours of incubation with a compound. Finally, the intensity of luminescence in every well was measured using Victor Light luminometer (Perkin Elmer, Inc.). The value of luminescence is proportion dependent on ATP quantity in the well in ATPlite test. The IC$_{50}$ value was determined based on the intensity of luminescence in wells containing different concentrations of compounds and control wells. IC$_{50}$ values were computed by fitting each point to the curve in non-linear regression model in Graph Pad software (ver. 5.03).

The results of the proliferation of SNU-15, UM-UC-14, AN3CA and Ba/F3 TEL-FGFR1 cell lines inhibition of selected compounds of the invention is presented in the following Table 2.

TABLE 2

| Example | SNU-16 IC$_{50}$ [nM] | UM-UC-14 IC$_{50}$ [nM] | AN3CA IC$_{50}$ [nM] | Ba/F3 TEL-FGFR1 IC$_{50}$ [nM] |
|---|---|---|---|---|
| Example 18 | 212 | 216 | 863 | 207 |
| Example 2 | 131 | 281 | 1982 | 1031 |
| Example 8 | 196 | 646 | 1268 | 4256 |
| Example 14 | 330 | 324 | 658 | 411 |
| Example 21 | 59 | 197 | 818 | 1100 |
| Example 27 | 272 | 758 | 1945 | 955 |
| Example 4 | 903 | 4262 | 2814 | >2500 |
| Example 3 | 981 | 1572 | 2333 | 2407 |

Western Blot Analysis of FGFR2 Protein Phosphorylation

The level of phosphorylation of FGFR2 kinase in the cell depends on its activity inhibition of FGFR2 kinase by an inhibitor (analyzed compound) causes the decrease of FGFR2 phosphorylation, what is observed in Western blot assay as a decline of a band immunodetected with anti-pFGFR (Tyr653/654) antibody. The inhibition of FGFR2 kinase should not interfere with total amount of FGFR protein-based on the immunodetection of FGFR2.

The phosphorylation of FGFR2 protein was evaluated in SNU-16 gastric cancer cell line model harboring FGFR2 amplification. This cell line is the accepted model to study the biological activity of FGFR2 kinase inhibitors (K. Kunii et al., Cancer Res 2008; 68:2340-2348).

The cells were seeded into 6-well plates with the density of 0.5×10$^6$/mL in the medium without the inhibitor. After 24 hours, cells were treated with the compound in the final concentration of 4 and 40 nM, for 1 hour. Then cells were lysed with RIPA buffer (Sigma-Aldrich), containing proteases inhibitors (Halt Protease Inhibitor Cocktail, Thermo) and phosphatase inhibitors (PhosSTOP, Roche). The protein concentration in cell lysates were measured with BCA assay (Pierce) according to manufacturer's instruction. Cell lysates were separated with SDS-PAGE through 2 hours at 100 V in Mini Protean III system (BioRad). Electrophoretically-fractionated proteins were subsequently electrotransferred onto the nitrocellulose membrane through 1 hour at 100 V in Mini Protean III system. Western blot analysis of selected proteins was performed according to antibodies manufacturers' instructions. In this analysis following primary antibodies were used: anti-pFGFR (Tyr653/654), anti-FGFR2 (Cell Signaling Technology). To detect primary antibodies immobilized onto the membrane, the secondary horseradish peroxidase-conjugated antibodies were used (Sigma-Aldrich). Immobilized proteins were visualized with LumiLight substrate (Roche) and subsequently exposed to Light Film BioMax (Kodak) which was developed.

The results of the test of FGFR2 phosphorylation in SNU-16 cells treated with selected compounds of invention at 4 and 40 nM for 1 hour are presented in FIG. 1, wherein the following abbreviations are used: C—control; 21—compound of Example 21; 20—compound of Example 20; 19—compound of Example 19.

The invention claimed is:
1. A compound represented by the general Formula (I)

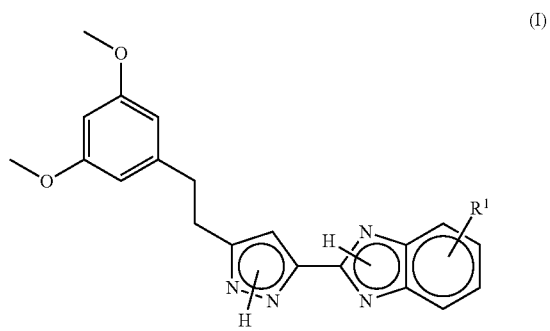

wherein
hydrogen atoms shown as attached to pyrazole and benzimidazole rings are attached to one of the nitrogen atoms of the pyrazole or benzimidazole ring, respectively;
R$^1$ represents —X-Q-P, wherein
X is absent or represents —CH$_2$—, —C(O)—, or —C(O)NH—(CH$_2$)$_k$—, wherein k is 0, 1 or 2;
Q is selected from the group consisting of Q1, Q2, Q3, Q4 and Q5, wherein
Q1 is

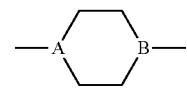

wherein A represents —CH— or nitrogen atom, and B represents —CH—, oxygen atom O or nitrogen atom, and when Q1 represents piperazinylene, it can be optionally additionally substituted with two methyl groups at the positions 3,5;
Q2 is

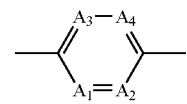

wherein one of A1, A2, A3, and A4 represents nitrogen atom, and the others represent C;
Q3 is

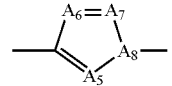

wherein one of A5, A6, A7 and A8 represents nitrogen atom, and the others represent C;
Q4 is

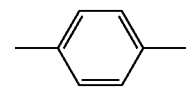

and Q5 is S

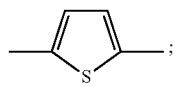

P is absent or represents straight- or branched-chain C1-C3 alkyl, —(CH$_2$)$_l$—NR$^2$R$^3$, or —(CH$_2$)$_m$—C(O)—NR$^2$R$^3$, wherein l and m independently of each other represent 0, 1 or 2, with the proviso that when B in Q1 represents oxygen atom, then P is absent; and R$^2$ and R$^3$ independently represent C1 or C2 alkyl, or R$^2$ and R$^3$ together with nitrogen atom to which they are both attached form a 6-membered saturated heterocyclic ring wherein one of carbon atoms of said heterocyclic ring can be optionally replaced with —O—, —NH— or —N(C1-C2)alkyl-;
and acid addition salts thereof.

2. The compound according to claim 1, wherein R$^1$ is attached at the position 4(7) of the benzimidazole ring.

3. The compound according to claim 1, wherein R$^1$ is attached at the position 5(6) of the benzimidazole ring.

4. The compound according to claim 3, wherein X is absent.

5. The compound according to claim 3, wherein X represents —C(O)—.

6. The compound according to claim 3, wherein X represents —CH$_2$—.

7. The compound according to claim 3, wherein P represents straight- or branched-chain C1-C3 alkyl.

8. The compound according to claim 3, wherein P is absent.

9. The compound according to claim 3, wherein Q represents Q1.

10. The compound according to claim 1 selected from the group consisting of the following:

4-((2-(5(3)-(3,5-dimethoxyphenethyl)-1H-pyrazol-3(5)-yl)-1H-benzo[d]imidazol-5(6)-yl)methyl)morpholine;
(2-(5(3)-(3,5-Dimethoxyphenethyl)-1H-pyrazol-3(5)-yl)-1H-benzo[d]imidazol-5(6)-yl) (morpholine)methanone;
2-(5(3)-(3,5-Dimethoxyphenethyl)-1H-pyrazol-3(5)-yl)-N-(tetrahydro-2H-pyran-4-ylo)-1H-benzo[d]imidazole-5(6)-carboxyamide;
2-(5(3)-(3,5-Dimethoxyphenethyl)-1H-pyrazol-3(5)-yl)-N-(3-morpholinepropyl)-1H-benzo[d]imidazole-5(6)-carboxyamide;
2-(5(3)-(3,5-Dimethoxyphenethyl)-1H-pyrazol-3(5)-yl)-5(6)-((4-ethylpiperazin-1-yl)methyl)-1H-benzo[d]imidazole;
(2-(5(3)-(3,5-Dimethoxyphenethyl)-1H-pyrazol-3(5)-yl)-1H-benzo[d]imidazol-5(6)-yl) (4-ethylpiperazin-1-yl)methanone;
2-(5(3)-(3,5-Dimethoxyphenethyl)-1H-pyrazol-3(5)-yl)-5(6)-((4-methylpiperazin-1-yl)methyl)-1H-benzo[d]imidazole;
(2-(5(3)-(3,5-Dimethoxyphenethyl)-1H-pyrazol-3(5)-yl)-1H-benzo[d]imidazol-5(6)-yl) (4-methylpiperazin-1-yl)methanone;
2-(5(3)-(3,5-Dimethoxyphenethyl)-1H-pyrazol-3(5)-yl)-5(6)-(((3R,5S)-3,5-dimethylpiperazin-1-yl)methyl)-1H-benzo[d]imidazole;
(2-(5(3)-(3,5-Dimethoxyphenethyl)-1H-pyrazol-3(5)-yl)-1H-benzo[d]imidazol-5-yl) ((3R,5S)-3,5-dimethylpiperazin-1-yl)methanone;
2-(5(3)-(3,5-Dimethoxyphenethyl)-1H-pyrazol-3(5)-yl)-5(6)-(piperidin-1-ylmethyl)-1H-benzo[d]imidazole;
2-(5(3)-(3,5-Dimethoxyphenethyl)-1H-pyrazol-3(5)-yl)-5(6)-((4-(4-methyl-piperazin-1-yl)piperidin-1-yl)methyl)-1H-benzo[d]imidazole;
5(6)-([1,4'-Bipiperidin]-1'-ylmethyl)-2-(5(3)-(3,5-dimethoxyphenethyl)-1H-pyrazol-3(5)-yl)-1H-benzo[d]imidazole;
4-(2-(4-((2-(5(3)-(3,5-Dimethoxyphenethyl)-1H-pyrazol-3(5)-yl)-1H-benzo[d]imidazol-5(6)-yl)methyl)piperazin-1-yl)ethyl)morpholine
2-(4-((2-(5(3)-(3,5-Dimethoxyphenethyl)-1H-pyrazol-3(5)-yl)-1H-benzo[d]imidazol-5(6)-yl)methyl)piperazin-1-yl)-N,N-dimethylacetamide;
4-2-(5(3)-(3,5-Dimethoxyphenethyl)-1H-pyrazol-3(5)-yl)-1H-benzo[d]imidazol-5(6)-yl)morpholine;
2-(5(3)-(3,5-Dimethoxyphenethyl)-1H-pyrazol-3(5)-yl)-5(6)-(4-methylpiperazin-1-yl)-1H-benzo[d]imidazole;
2-(5(3)-(3,5-Dimethoxyphenethyl)-1H-pyrazol-3(5)-yl)-5(6)-(4-ethylpiperazin-1-ylo)-1H-benzo[d]imidazole;
2-(5(3)-(3,5-Dimethoxyphenethyl)-1H-pyrazol-3(5)-yl)-5(6)-((3R,5S)-3,5-dimethylpiperazin-1-yl)-1H-benzo[d]imidazole
2-(4-(2-(5(3)-(3,5-Dimethoxyphenethyl)-1H-pyrazol-3(5)-yl)-1H-benzo[d]imidazol-5(6)-yl)piperazin-1-yl)-N,N-diethylethanamine;
2-(4-(2-(5(3)-(3,5-Dimethoxyphenethyl)-1H-pyrazol-3(5)-yl)-1H-benzo[d]imidazol-5(6)-yl)piperazin-1-yl)-1-(morpholine)ethanone;
4-(2-(5(3)-(3,5-Dimethoxyphenethyl)-1H-pyrazol-3(5)-yl)-1H-benzo[d]imidazol-4(7)-yl)morpholine;
2-(5(3)-(3,5-Dimethoxyphenethyl)-1H-pyrazol-3(5)-yl)-4(7)-((3R,5S)-3,5-dimethylpiperazin-1-yl)-1H-benz[d]imidazole;
2-(5(3)-(3,5-Dimethoxyphenethyl)-1H-pyrazol-3(5)-yl)-4(7)-(4-isopropylpiperazin-1-yl)-1H-benzo[d]imidazole;
4(7)-([1,4'-bipiperidin]-1'-ylo)-2-(5(3)-(3,5-dimethoxyphenethyl)-1H-pyrazol-3(5)-yl)-1H-benzo[d]imidazole;
4-(2-(4-(2-(5(3)-(3,5-Dimethoxyphenethyl)-1H-pyrazol-3(5)-yl)-1H-benzo[d]imidazol-4(7)-yl)piperazin-1-yl)ethyl)morpholine;
4-(2-(2-(5(3)-(3,5-Dimethoxyphenethyl)-1H-pyrazol-3(5)-yl)-1H-benzo[d]imidazol-5(6)-yl)-1H-pyrazol-1-yl)ethyl)morpholine;
4-((5(3)-(2-(5(3)-(3,5-Dimethoxyphenethyl)-1H-pyrazol-3(5)-yl)-1H-benzo[d]imidazol-5(6)-yl)thiophen-2-yl)methyl)morpholine;
4-(3-(2-(5(3)-(3,5-Dimethoxyphenethyl)-1H-pyrazol-3(5)-yl)-1H-benzo[d]imidazol-5(6)-yl)benzyl)morpholine;
(4-(2-(5(3)3-(3,5-Dimethoxyphenethyl)-1H-pyrazol-3(5)-yl)-1H-benzo[d]imidazol-5(6)-yl)phenyl) (morpholine)methanone;
(4-(2-(5(3)-(3,5-Dimethoxyphenethyl)-1H-pyrazol-3(5)-yl)-1H-benzo[d]imidazol-5(6)-yl)phenyl) (morpholine)methanone;
4-(4-(2-(3-(3,5-Dimethoxyphenethyl)-1H-pyrazol-3(5)-yl)-1H-benzo[d]imidazol-5(6)-ylo)phenyl)morpholine, and
4-(5(3)-(2-(3-(3,5-Dimethoxyphenethyl)-1H-pyrazol-3(5)-yl)-1H-benzo[d]imidazol-5(6)-yl)pyridin-2-yl)morpholine;
and their acid addition salts.

11. A pharmaceutical composition comprising as an active ingredient a compound of the general Formula (I) as defined in claim 1, and pharmaceutically acceptable excipients.

12. A method of treatment of cancer in a mammal subject, comprising administration of a therapeutically effective amount of the compound of the general Formula (I) as defined in claim 1 or the composition as defined in claim 11, wherein the cancer is mediated by FGFR.

13. The compound according to claim 3 wherein
X is absent or represents —CH$_2$— or —C(O)—;
P is absent or represents straight- or branched-chain C1-C3 alkyl; and
Q is Q1.

14. The compound according to claim 13 wherein X is absent.

15. The compound according to claim 14 wherein A represents nitrogen atom, B represents nitrogen atom and Q1 can be optionally additionally substituted with two methyl groups at the positions 3,5.

16. The compound according to claim 15 wherein P represents methyl.

17. The compound according to claim 15 wherein P represents ethyl.

18. The compound according to claim 14 wherein A represents nitrogen atom, B represents nitrogen atom, and Q1 is substituted with two methyl groups at the positions 3,5, and P is absent.

19. The compound according to claim 14 wherein A represents nitrogen atom, B represents oxygen atom, and P is absent.

20. The compound according to claim 13 wherein X represents —CH$_2$—.

21. The compound according to claim 20 wherein A represents nitrogen atom, B represents nitrogen atom, and P is absent or P represents methyl or ethyl.

22. The compound according to claim 20 wherein A represents nitrogen atom, B represents oxygen atom, and P is absent or represents methyl or ethyl.

23. The compound according to claim 20 wherein A represents nitrogen atom, B represents nitrogen atom, and Q1 is substituted with two methyl groups at the positions 3,5, and P is absent.

24. The compound according to claim 20 wherein A represents nitrogen atom, B represents —CH—, and P is absent.

25. The compound according to claim 13 wherein X represents —C(O)—.

26. The compound according to claim 25 wherein A represents nitrogen atom, B represents nitrogen atom, and P represents methyl or ethyl.

27. The compound according to claim 25 wherein A represents nitrogen atom, B represents oxygen atom, and P is absent.

28. The compound according to claim 25 wherein A represents nitrogen atom, B represents nitrogen atom, and Q1 is substituted with two methyl groups at the positions 3,5, and P is absent.

29. The compound according to claim 13 selected from the group consisting of the following:
4-((2-(5(3)-(3,5-dimethoxyphenethyl)-1H-pyrazol-3(5)-yl)-H-benzo[d]imidazol-5(6)-yl)methyl)morpholine;
(2-(5(3)-(3,5-Dimethoxyphenethyl)-1H-pyrazol-3(5)-yl)-1H-benzo[d]imidazol-5(6)-yl) (morpholine)methanone;
2-(5(3)-(3,5-Dimethoxyphenethyl)-1H-pyrazol-3(5)-yl)-5(6)-((4-ethylpiperazin-1-yl)methyl)-1H-benzo[d]imidazole;
(2-(5(3)-(3,5-Dimethoxyphenethyl)-1H-pyrazol-3(5)-yl)-1H-benzo[d]imidazol-5(6)-yl) (4-ethylpiperazin-1-yl) methanone;
2-(5(3)-(3,5-Dimethoxyphenethyl)-1H-pyrazol-3(5)-yl)-5(6)-((4-methylpiperazin-1-yl)methyl)-1H-benzo[d] imidazole;
(2-(4(3)-(3,5-Dimethoxyphenethyl)-1H-pyrazol-3(5)-yl)-1H-benzo[d]imidazol-5(6)-yl) (4-methylpiperazin-1-yl)methanone;
2-(5(3)-(3,5-Dimethoxyphenethyl)-1H-pyrazol-3(5)-yl)-5(6)-(((3R,5S)-3,5-dimethylpiperazin-1-yl)methyl)-1H-benzo[d]imidazole;
(2-(5(3)-(3,5-Dimethoxyphenethyl)-1H-pyrazol-3(5)-yl)-1H-benzo[d]imidazol-5-yl) ((3R,5S)-3,5-dimethylpiperazin-1-yl)methanone;
2-(5(3)-(3,5-Dimethoxyphenethyl)-1H-pyrazol-3(5)-yl)-5(6)-(piperidin-1-ylmethyl)-1H-benzo[d]imidazole;
4-(2-(5(3)-(3,5-Dimethoxyphenethyl)-1H-pyrazol-3(5)-yl)-1H-benzo[d]imidazol-5(6)-yl)morpholine;
2-(5(3)-(3,5-Dimethoxyphenethyl)-1H-pyrazol-3(5)-yl)-5(6)-(4-methylpiperazin-1-yl)-1H-benzo[d]imidazole;
2-(5(3)-(3,5-Dimethoxyphenethyl)-1H-pyrazol-3(5)-yl)-5(6)-(4-ethylpiperazin-1-ylo)-1H-benzo[d]imidazole;
2-(5(3)-(3,5-Dimethoxyphenethyl)-1H-pyrazol-3(5)-yl)-5(6)-((3R,5S)-3,5-dimethylpiperazin-1-yl)-1H-benzo[d]imidazole
and their acid addition salts.

30. The compound according to claim 13 selected from 2-(5(3)-(3,5-dimethoxyphenethyl)-1H-pyrazol-3(5)-yl)-5(6)-(4-methylpiperazin-1-yl)-1H-benzo[d]imidazole and its acid addition salts.

31. The compound according to claim 1, wherein Q3 is Q31,
wherein Q31 is

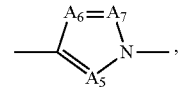

wherein one of A5, A6 and A7 represents nitrogen atom, and the others represent C.

32. The method of claim 12, wherein the subject is human.

* * * * *